US011744798B2

(12) United States Patent
Nuopponen et al.

(10) Patent No.: US 11,744,798 B2
(45) Date of Patent: *Sep. 5, 2023

(54) INJECTABLE PHARMACEUTICAL FORMULATION

(71) Applicant: UPM-Kymmene Corporation, Helsinki (FI)

(72) Inventors: Markus Nuopponen, Helsinki (FI); Lauri Paasonen, Järvenpää (FI); Anne Meriluoto, Helsinki (FI); Jukka Rissanen, Kuusisto (FI); Harri Jukarainen, Kuusisto (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/015,415

(22) Filed: Sep. 9, 2020

(65) Prior Publication Data

US 2021/0085602 A1    Mar. 25, 2021

(30) Foreign Application Priority Data

Sep. 13, 2019 (EP) .................................... 19397528

(51) Int. Cl.

| | |
|---|---|
| *A61K 9/06* | (2006.01) |
| *A61P 25/04* | (2006.01) |
| *A61K 9/00* | (2006.01) |
| *A61K 31/403* | (2006.01) |
| *A61K 31/4152* | (2006.01) |
| *A61K 31/485* | (2006.01) |
| *A61K 31/541* | (2006.01) |
| *A61K 47/20* | (2006.01) |
| *A61K 47/22* | (2006.01) |
| *A61K 47/38* | (2006.01) |

(52) U.S. Cl.
CPC .............. *A61K 9/06* (2013.01); *A61K 9/0019* (2013.01); *A61K 31/403* (2013.01); *A61K 31/4152* (2013.01); *A61K 31/485* (2013.01); *A61K 31/541* (2013.01); *A61K 47/20* (2013.01); *A61K 47/22* (2013.01); *A61K 47/38* (2013.01); *A61P 25/04* (2018.01)

(58) Field of Classification Search
CPC .............................. A61K 9/0019; A61K 47/38
See application file for complete search history.

(56) References Cited

U.S. PATENT DOCUMENTS

| | | | |
|---|---|---|---|
| 6,361,797 B1 * | 3/2002 | Kuzma | A61K 9/0092 424/486 |
| 2012/0135081 A1 * | 5/2012 | Laaksonen | A61K 47/6923 977/773 |
| 2013/0330379 A1 | 12/2013 | Ylipertula et al. | |
| 2015/0367024 A1 * | 12/2015 | Laukkanen | A61L 15/60 424/444 |
| 2019/0083626 A1 * | 3/2019 | Goldberg | A61K 38/1793 |
| 2021/0077403 A1 | 3/2021 | Nuopponen et al. | |

FOREIGN PATENT DOCUMENTS

| | | | | |
|---|---|---|---|---|
| CN | 103520739 A | 1/2014 | | |
| WO | 2013072563 A1 | 5/2013 | | |
| WO | WO-2013072563 A1 * | 5/2013 | ........... | A61K 31/137 |

OTHER PUBLICATIONS

Paukkonen, International Journal of Pharmaceutics, 532, 2017 (Year: 2017).*
Graves, AAPS PharmSciTech, 8, 3, 2007 (Year: 2007).*
Paukkonen, H. et al. "Nanofibrillar cellulose hydrogels and reconstructed hydrogels as matrices for controlled drug release", International Journal of Pharmaceutics, vol. 532, 2017; pp. 269-280.
Jackson, J. K., et al., "The use of nanocrystalline cellulose for the binding and controlled release of drugs", International Journal of Nanomedicine, vol. 6, 2011; pp. 321-330.
Valo, H. et al., "Immobilization of protein-coated drug nanoparticles in nanofibrillar cellulose matrices—Enhanced stability and release", Journal of Controlled Release, vol. 156, 2011; pp. 390-397.

* cited by examiner

*Primary Examiner* — Robert A Wax
*Assistant Examiner* — William Craigo
(74) *Attorney, Agent, or Firm* — CANTOR COLBURN LLP

(57) ABSTRACT

An injectable pharmaceutical formulation includes nanofibrillar cellulose hydrogel wherein the content of nanofibrillar cellulose in the pharmaceutical formulation is the range of 1-8% (w/w), and pharmaceutical compound. The injectable pharmaceutical formulation can provide a sustained release of a pharmaceutical compound in a subject. Use of nanofibrillar cellulose for preparing the injectable pharmaceutical formulation is also disclosed.

23 Claims, 31 Drawing Sheets

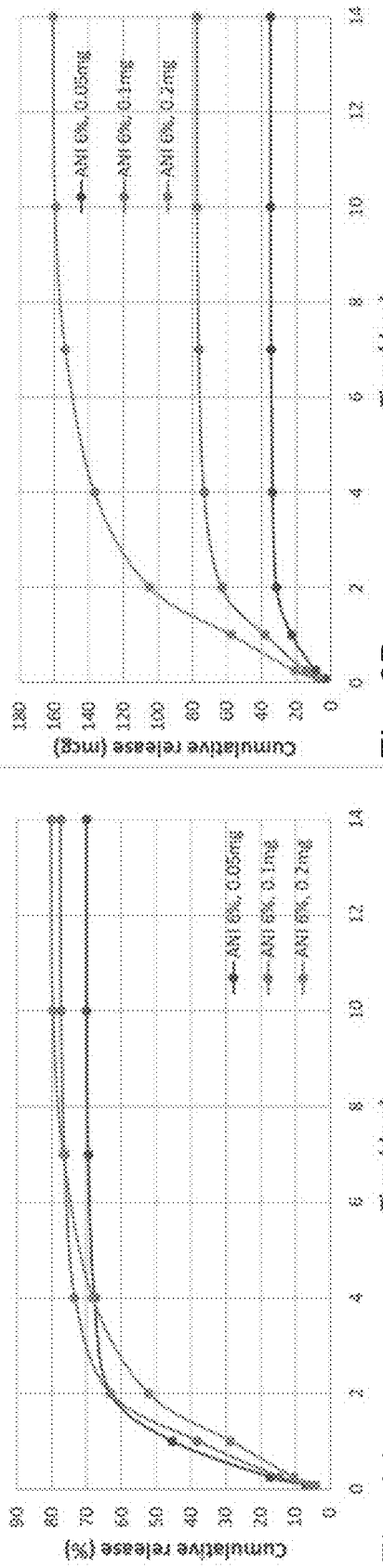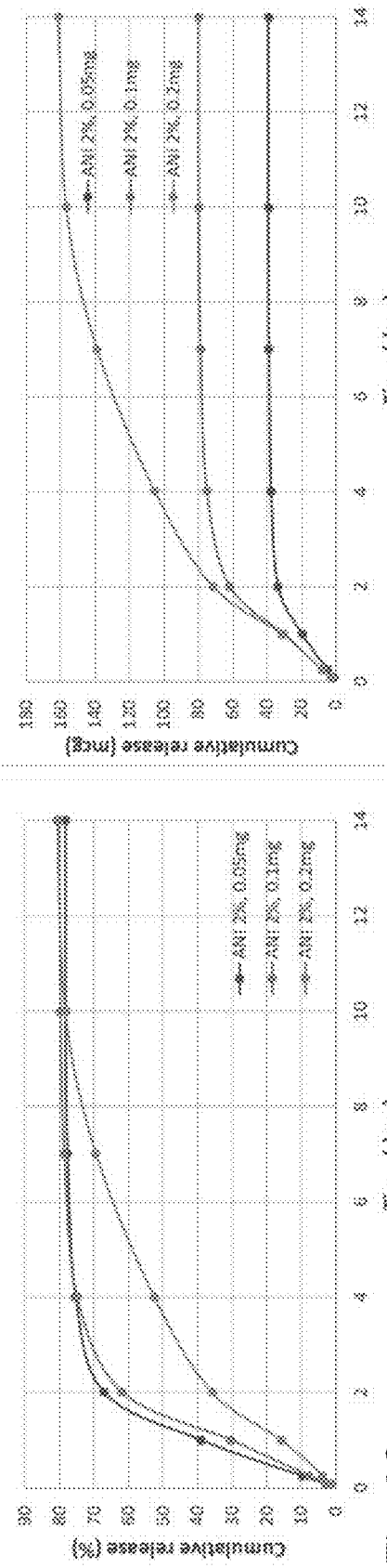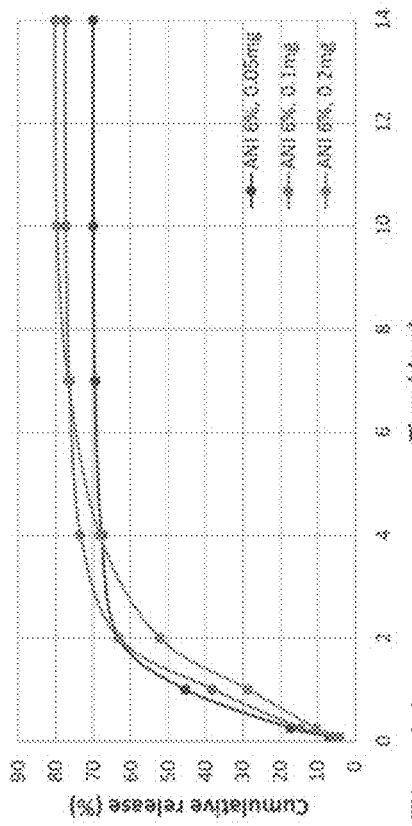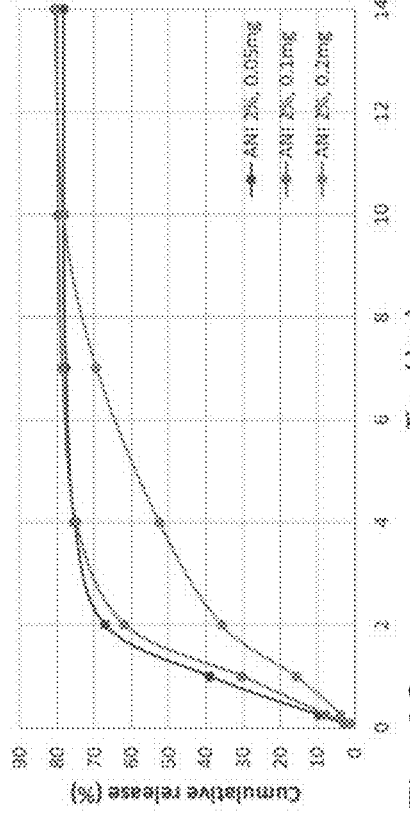

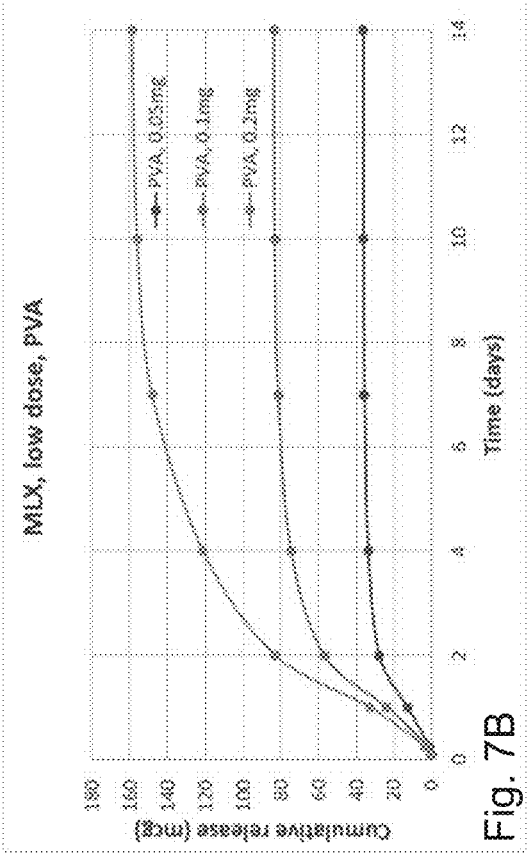
Fig. 7A
Fig. 7B
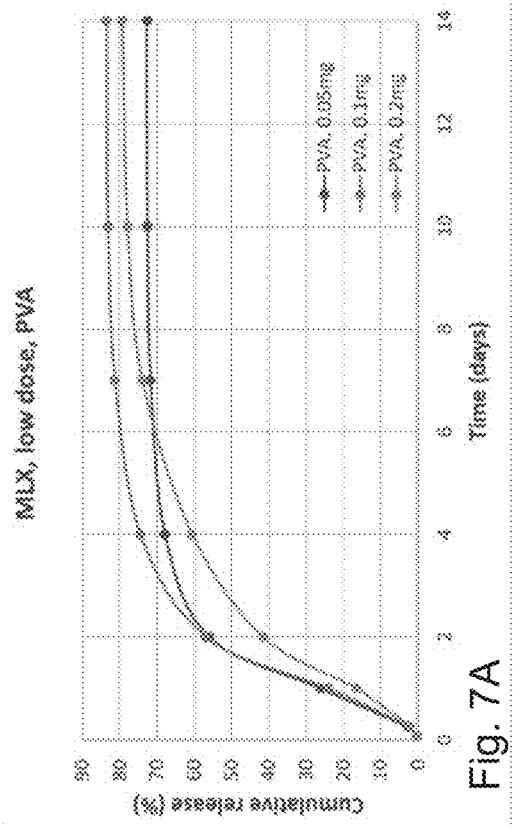
Fig. 7C
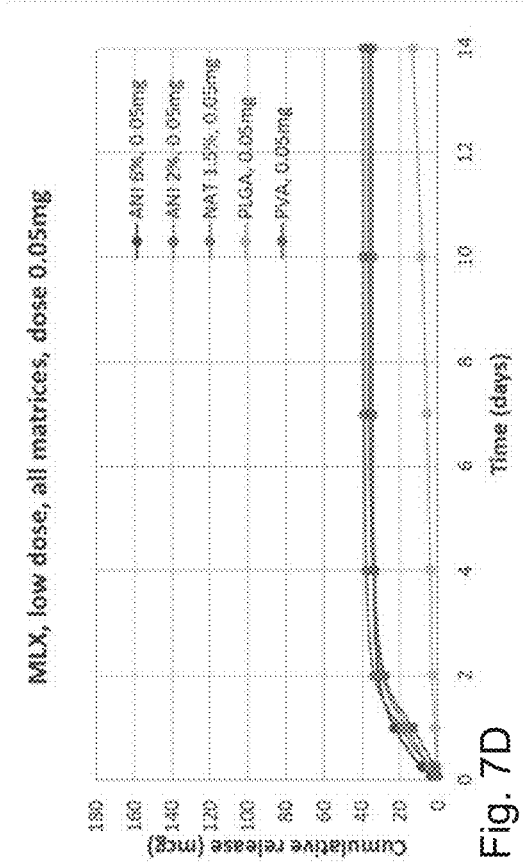
Fig. 7D
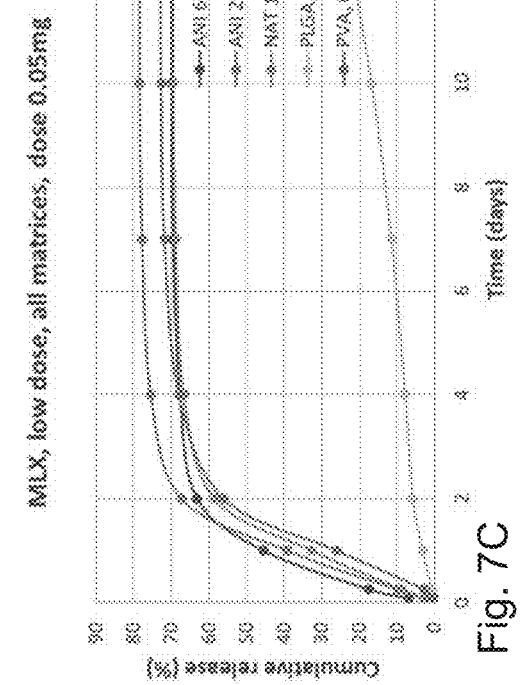

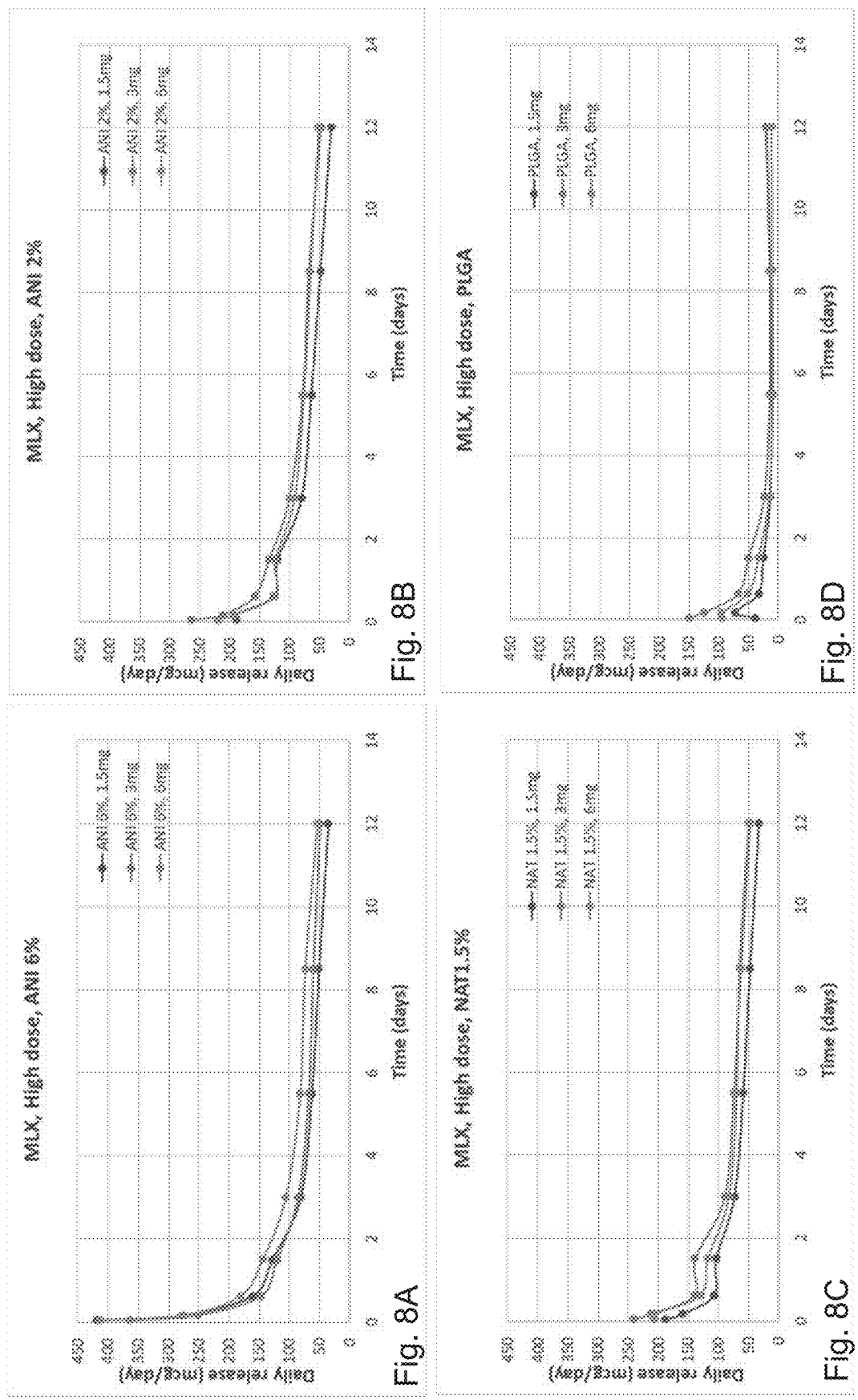

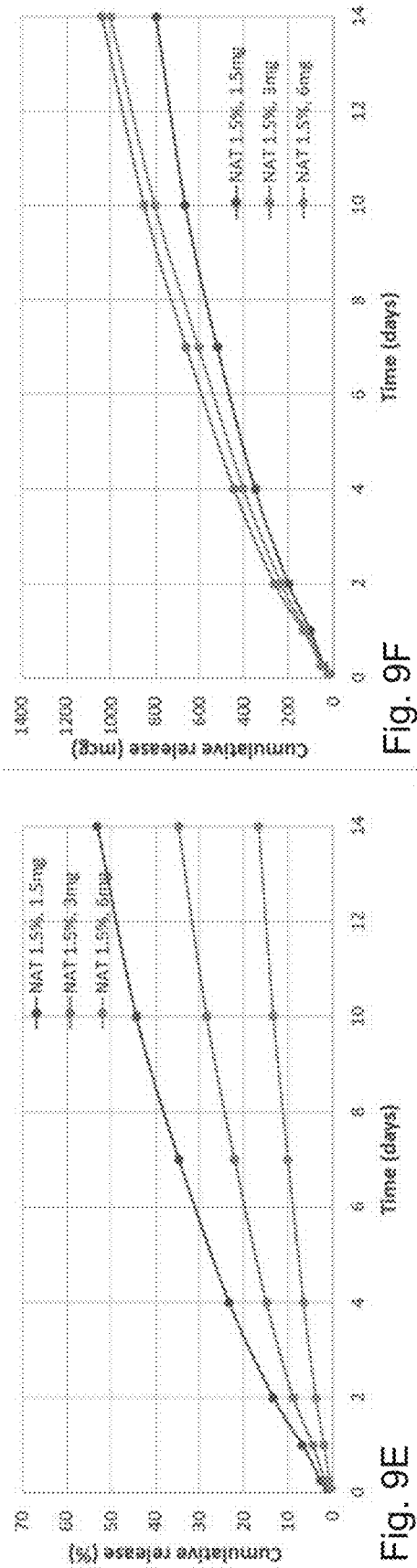
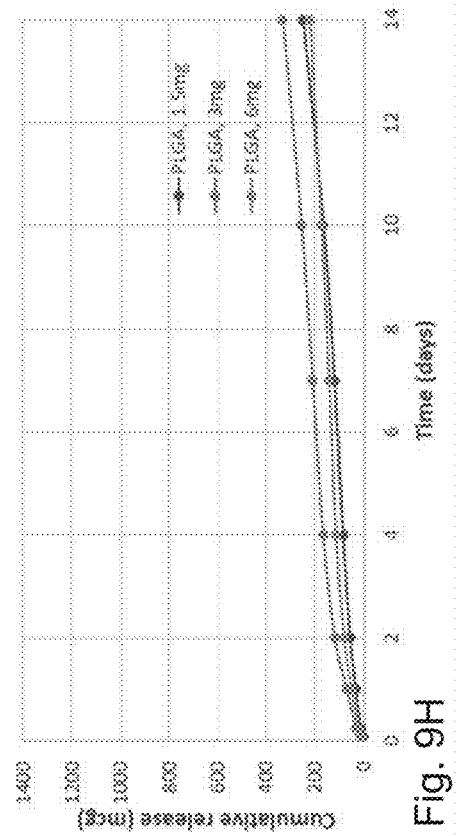
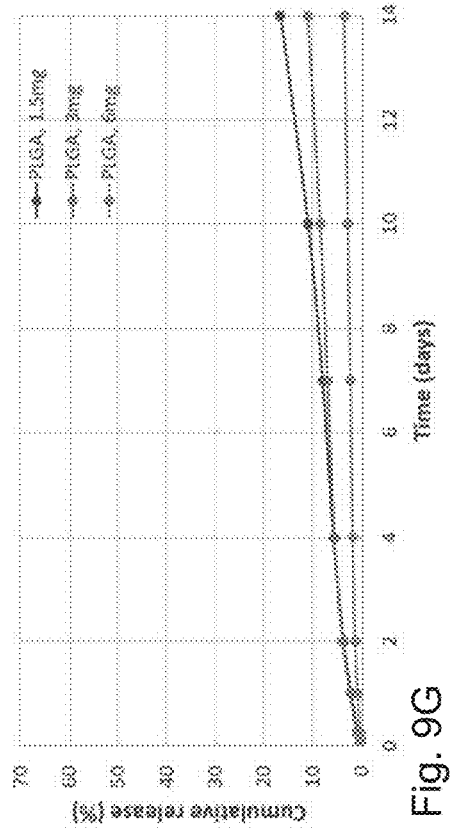
Fig. 9E  Fig. 9F  Fig. 9G  Fig. 9H

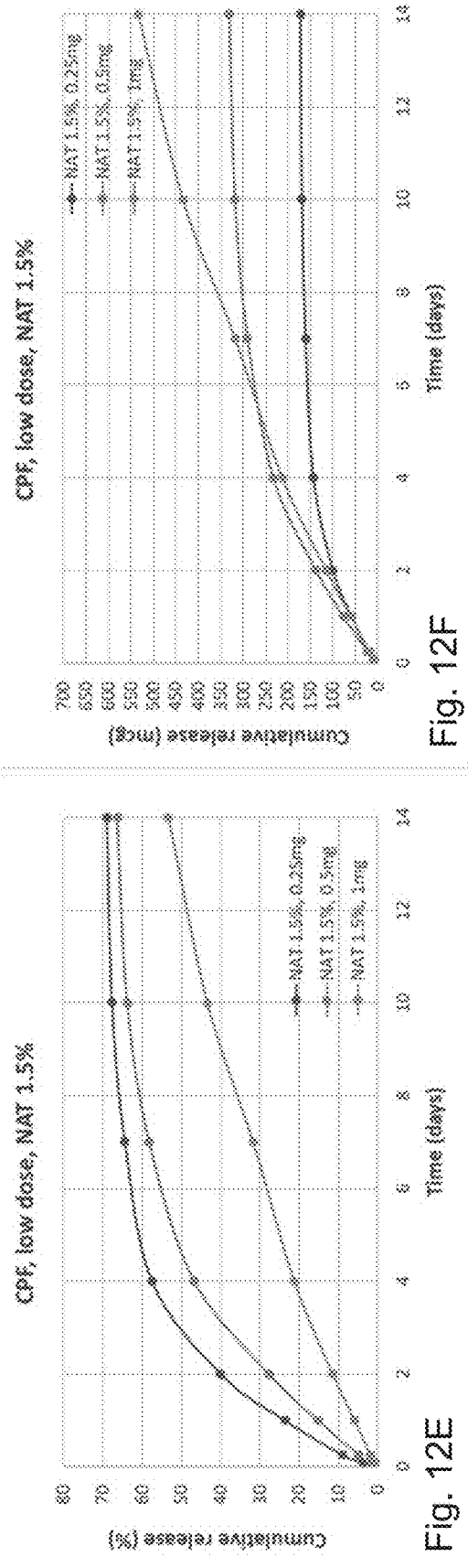
Fig. 12E
Fig. 12F
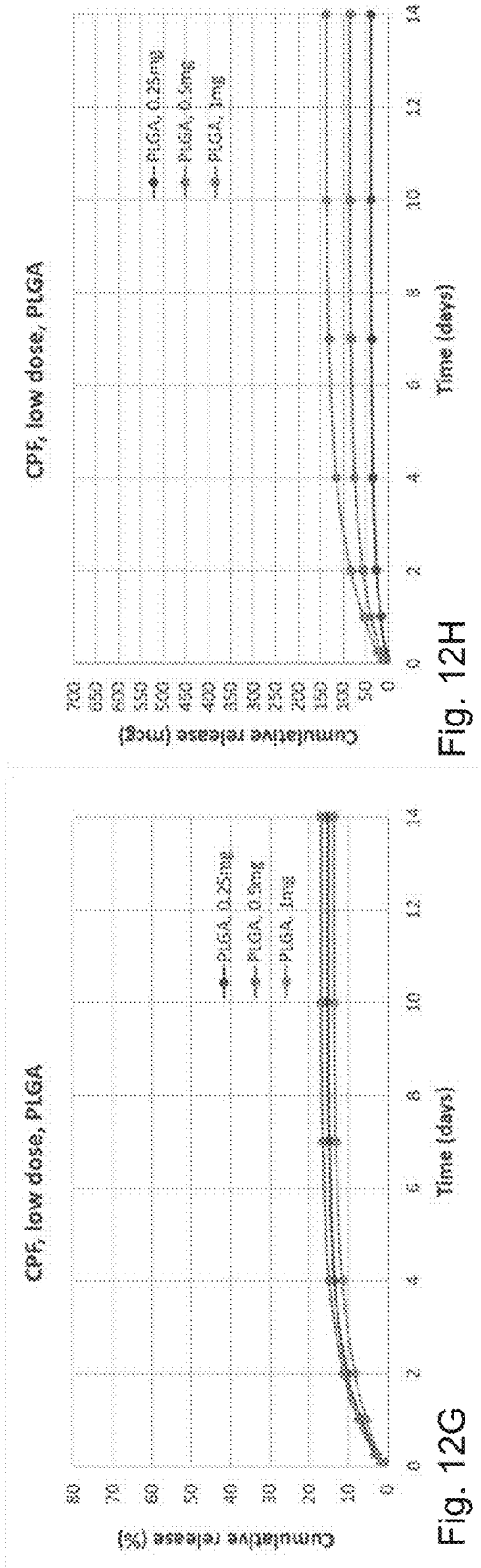
Fig. 12G
Fig. 12H

INJECTABLE PHARMACEUTICAL FORMULATION

CROSS REFERENCE TO RELATED APPLICATION

This application claims priority to and benefit of European Patent Application No. 19397528.1, filed Sep. 13, 2019, the contents of which is incorporated by reference herein in its entirety.

TECHNICAL FIELD

The present application relates to injectable and implantable pharmaceutical formulations, and to the injectable pharmaceutical formulation for use for injecting a pharmaceutical compound to a subject and for use for providing a sustained release of a pharmaceutical compound in a subject.

BACKGROUND

In certain cases it is necessary to administer a pharmaceutical compound to a subject, such as a patient, as a modified-release dosage, which is used to deliver the compound with a delay after its administration, for a prolonged period of time, and/or to a specific target in a body. Sustained-release dosage forms are dosage forms designed to release a pharmaceutical compound at a predetermined and/or controlled rate to maintain a constant or otherwise desired concentration of the compound. A variety of drug formulations can be used, such as injectable formulations. However, many carriers used in such formulations are problematic, for example the carrier material may have a great impact to the release profile of the pharmaceutical.

There is a need in market for injectable material which enables sustained release for a prolonged time. Formulation stability, bioavailability, release kinetics and injectability are challenges that must be overcome for maximal effectiveness.

SUMMARY

It was found out that by using nanofibrillar cellulose as a carrier or matrix material it is possible to obtain modified-release materials and dosages, such as injectables, implants and the like, which may be used to deliver pharmaceuticals to a subject in controlled release manner.

The present application provides an injectable pharmaceutical formulation comprising
nanofibrillar cellulose hydrogel having a content of nanofibrillar cellulose in the range of 1-8% (w/w), wherein the nanofibrillar cellulose has an average fibril diameter of 200 nm or less, such as in the range of 1-200 nm, and a pharmaceutical compound,
the formulation having a storage modulus of 350 Pa or more, and a yield stress/fracture strength of 25 Pa or more, determined by stress controlled rotational rheometer with gradually increasing shear stress in a range of 0.001-100 Pa at a frequency 10 rad/s, strain 2%, at 25° C.

The present application provides a syringe containing the injectable pharmaceutical formulation.

The present application provides an implant containing the injectable pharmaceutical formulation.

The present application provides use of nanofibrillar cellulose for preparing the injectable pharmaceutical formulation or the implant.

The main embodiments are characterized in the independent claims. Various embodiments are disclosed in the dependent claims. The embodiments and examples recited in the claims and the specification are mutually freely combinable unless otherwise explicitly stated.

The nanofibrillar cellulose, which is present as a hydrogel, provides a hydrophilic matrix, which is non-toxic, biocompatible and also biodegradable.

The matrix can be degraded enzymatically, for example by adding cellulase. On the other hand the hydrogel is stable at physiological conditions, and does not need to be cross-linked by using additional agents. The nanofibrillar cellulose as an insoluble carrier or matrix material is stable and does not degrade easily, for example during storage or after administration. The properties, such as permeability, of the nanofibrillar cellulose hydrogel may be controlled by adjusting the chemical and/or physical properties of the nanofibrillar cellulose.

Certain advantageous properties of the hydrogel comprising nanofibrillar cellulose include flexibility, elasticity and remouldability. As the hydrogel contains a lot of water, it also shows good permeability for molecules. The hydrogels of the embodiments also provide high water retention capacity and molecule diffusion property speed.

Nanofibrillar cellulose at a concentration containing relatively large portion of water was found out to be a suitable matrix for preparing formulations for injection. It was discovered that the concentration of the nanofibrillar cellulose has little effect to the release of the pharmaceutical from the matrix, and the diffusion of the pharmaceutical from a nanofibrillar cellulose matrix is mainly based on the properties of the pharmaceutical itself. Therefore it is possible to obtain a variety of different pharmaceutical formulations for different uses, and to control and adjust the amount and release of a drug from the composition. By using the stabile nanofibrillar cellulose matrix it is possible to provide constant conditions for administering drugs. This is especially advantageous when injectable or implantable formulations are desired.

It is therefore possible to obtain extended, sustained and/or prolonged treatment of animal or human subject with a drug of interest, such as an analgesic drug. In the tests it was noticed that a sustained release of 3-14 days was easily obtained with injectable formulations. It was also possible to obtain a high but controllable initial burst of drug release, such as a release of only 5-10% of the total dose within first 6 hours. The present compositions are suitable for prolonged analgesic treatment, i.e. pain management, especially for post-operative pain management, but also for chronic pain management.

The pharmaceutical formulations and compositions are suitable to be administered to animals, such as laboratory animals, for example rodents. The animal may or may not include human. The pharmaceutical formulation may be a pharmaceutical veterinary formulation.

Nanofibrillar cellulose hydrogels are injectable and implantable and thus capable of delivering substances to a desired subject or target. Nanofibrillar cellulose hydrogels are pseudoplastic or shear-thinning non-Newtonian fluids which makes them easily injectable, as the extruding shearing force during the injection is large enough to reduce viscosity of the viscous material present in a syringe, and after the injection the material will stabilize in the target after the shearing force is removed. Conventional i.e. Newtonian fluids do not exhibit this behaviour. This behaviour is especially advantageous when injecting into a muscle or under skin, and it is possible to obtain desired and stable shape and length of the injected material in the target. The behaviour also stabilizes the material during storage, including when the material is present in a syringe.

The NFC hydrogel can be used as a matrix for non-water soluble or limited water-soluble drug powders preventing agglomeration, aggregation, clotting or mounting by gravity, thus stabilizing the drug and enhancing bioavailability and dissolution rate. The hydrogel may be also applied in oral dosage forms (gel capsules) or injectable fluids. This phenomenon was noticed during experimental work. Because of the stability the injectable pharmaceuticals can be stored in the NFC hydrogels for long time even as the hydrogels contain a large portion of water. This facilitates the whole process of preparing, packing, providing, storing and using the formulations.

It was found out that the pharmaceutical formulation exhibiting the stability, bioavailability and sustained release properties was especially suitable for subcutaneous, intradermal or intramuscular administration. The injected material remained in the target without causing undesired reactions in the subject, and the pharmaceutical compound was efficiently released as desired and provided also the desired effect.

BRIEF DESCRIPTION OF THE FIGURES

FIG. 6A shows cumulative release of meloxicam in extensive dissolution study up to 14 days with Anionic 6% NFC matrix.

FIG. 6B shows cumulative release of meloxicam in extensive dissolution study up to 14 days with Anionic 6% NFC matrix.

FIG. 6C shows cumulative release of meloxicam in extensive dissolution study up to 14 days with Anionic 2% NFC matrix.

FIG. 6D shows cumulative release of meloxicam in extensive dissolution study up to 14 days with Anionic 2% NFC matrix.

FIG. 7A shows cumulative release of meloxicam in extensive dissolution study up to 14 days with PVA matrix.

FIG. 7B shows cumulative release of meloxicam in extensive dissolution study up to 14 days with PVA matrix.

FIG. 7C shows cumulative release of meloxicam in extensive dissolution study up to 14 days with all matrices at a dose of 0.05 mg.

FIG. 7D shows cumulative release of meloxicam in extensive dissolution study up to 14 days with all matrices at a dose of 0.05 mg.

FIG. 8A shows daily release of meloxicam in extensive dissolution study up to 14 days with Anionic 6% NFC matrix.

FIG. 8B shows daily release of meloxicam in extensive dissolution study up to 14 days with Anionic 2% NFC matrix.

FIG. 8C shows daily release of meloxicam in extensive dissolution study up to 14 days with Native 1.5% NFC matrix.

FIG. 8D shows daily release of meloxicam in extensive dissolution study up to 14 days with PLGA matrix.

FIG. 9E shows daily release of meloxicam in extensive dissolution study up to 14 days with Native 1.5% NFC matrix.

FIG. 9F shows daily release of meloxicam in extensive dissolution study up to 14 days with Native 1.5% NFC matrix.

FIG. 9G shows daily release of meloxicam in extensive dissolution study up to 14 days with PLGA matrix.

FIG. 9H shows daily release of meloxicam in extensive dissolution study up to 14 days with PLGA matrix.

FIG. 12E shows daily release of carprofen in extensive dissolution study up to 14 days with Native 1.5% NFC matrix.

FIG. 12F shows daily release of carprofen in extensive dissolution study up to 14 days with Native 1.5% NFC matrix.

FIG. 12G shows daily release of carprofen in extensive dissolution study up to 14 days with PLGA matrix.

FIG. 12H shows daily release of carprofen in extensive dissolution study up to 14 days with PLGA matrix.

DETAILED DESCRIPTION

Figure 1:
FIG. 1 shows dissolution set-up for API-NFC injection. A) Dissolution vial, stainless-steel spring, pouch, metal grid and injection needle with NFC-API suspension separately. B) Injection was made inside the sealed cellulose pouch (Ankom Technologies, F58, 5-8 μm porosity) with spring inside to keep the pouch slightly open. C) Cellulose pouch was placed inside loose metal grid and placed in dissolution vial with dissolution solution (0.9% NaCl). The vessel was placed in incubator with orbital shaking. D) cellulose pouch opened after dissolution. NFC-API-injection can be seen around the spring.

In this specification, percentage values, unless specifically indicated otherwise, are based on weight (w/w). If any numerical ranges are provided, the ranges include also the upper and lower values. The open term "comprise" also includes a closed term "consisting of" as one option.

The materials and products described herein may be medical and/or scientific materials and products, such as life science materials and products, and may be used in the methods and the applications involving living cells and/or bioactive material or substances, such as described herein. The materials or products may be or relate to cell culture, cell storage and/or cell study materials or products, and may be used in methods wherein cells are cultured, stored, maintained, transported, provided, modified, tested, and/or used for medical or scientific purposes, or in other related and applicable methods.

Correct dose of analgesic has a pivotal role in preclinical animal studies. The goal of proper postoperative pain management is to minimize pain and discomfort without producing unacceptable adverse effects. Assessing pain in rodents can be difficult as they typically minimize pain-associated behaviours unless the pain is incapacitating. Therefore, pain management in preclinical animal studies must include pharmaceutical intervention. The efficacy of the analgesic drug is not only dependent on the analgesic compound itself. Formulation stability, bioavailability, release kinetics and injectability are challenges that must be overcome for maximal effectiveness. Excipients and sustained release technologies offer solutions for these challenges. In preclinical settings, most it is desired to dose the compound as a conventional injection. The present application provides NFC gel based injections and implants for analgesic drug for example for preclinical research use. The pharmaceutical formulations disclosed herein may provide or comprise extended release dosage or composition.

Extended-release dosage may comprise a sustained-release (SR) or controlled-release (CR) dosage. SR maintains drug release over a sustained period but not at a constant rate. CR maintains drug release over a sustained period at a nearly constant rate.

The present application provides an injectable pharmaceutical formulation comprising
nanofibrillar cellulose hydrogel wherein the content of nanofibrillar cellulose in the pharmaceutical formulation is the range of 1-8% (w/w), and
pharmaceutical compound.

The present application also provides in injectable pharmaceutical product obtained with said method. A pharmaceutical product is an isolated product, which may be formulated and provided as a ready for use, such as in homogenous and sterile form packed or otherwise prepared to be used. Intermediate products of a process are excluded from the definition. The formulation of the product may be provided as one or more doses for injection, such as packed into a vial or a syringe. The terms "formulation", "composition" and "product" may be used interchangeably, when applicable.

A "formulation" as used herein refers to a form of a composition, which has been specifically formed for a specific purpose, which herein is injection. Formulation is a process wherein chemical substances, including the active pharmaceutical compound, are combined to produce a final medicinal product. A formulation may be provided in a dosage form. A formulation may be formed to obtain desired property or properties for a specific use, such as injectability and a desired sustained release of the pharmaceutical compound.

The formulation, the composition or the product is injectable i.e. it is provided for injection, especially with an injection needle, which means that it may be injected into a subject, i.e. it may be provided for subcutaneous, intradermal or intramuscular administration by injecting. Injectability is obtained by providing the material in a suitable form, which includes for example concentration, rheological properties, homogeneity, stability and bioavailability of the pharmaceutical compound, especially when administrated by injecting with a needle into a tissue, and the like properties.

The product may be in a form of hydrogel having a water content of at least 82% (w/w), or at least 85% (w/w), or preferably at least 90% (w/w) to obtain well injectable formulations, which is a very high water content, so the obtained composition or product is suitable for different types of administrations. The composition may be present as a flowing dispersion, but it may be also present as a hydrogel, such as a flowing hydrogel and/or injectable hydrogel. The hydrogel, which is shear-thinning material, may turn flowable and/or injectable when injected, i.e. when pressure is applied to the hydrogel by operating a syringe. In one example the dispersion of nanofibrillar cellulose comprises hydrogel. The formulation may be present as a hydrogel during storage, which provides stability and shelf file, for example as the material does not agglomerate or precipitate, but during use, i.e. the injection, the material thins thus allowing efficient injection via a needle precisely into a target, after which it returns back to the previous thicker form.

The water content may be adjusted according to the portions of nanofibrillar cellulose and pharmaceutical compound. The sum of the amounts add up to 100% (w/w). The water content may be in the range of 82-98.9% (w/w), such as 85-98.9% (w/w), 90-98.9% (w/w) of 92-98.9% (w/w). In examples the water content is in the range of 82-98% (w/w), 85-98% (w/w), 90-98% (w/w) or 92-98% (w/w).

For example injectable compositions may have a water content in the range of 92-98.9% (w/w) and/or content of nanofibrillar cellulose in the range of 1-8% (w/w), which provide suitable shear-thinning properties. To obtain the desired shear-thinning properties of the formulation, the formulation may contain nanofibrillar cellulose as the only polymeric material in the composition, and the composition may contain substantially only or consist of the pharmaceutical compound(s), the nanofibrillar cellulose and water. In some cases minor amounts of additives customary in the art, such as colouring agent(s), preservative agent(s) or the like agents, which preferably have no effect to the structure or rheological properties of the composition, may be included, preferably in an amount of 0.5% (w/w) or less, such as 0.2% (w/w) or less, or 0.1% (w/w) or less.

The content of the nanofibrillar cellulose in the pharmaceutical formulation may be in the range of 1-7% (w/w) or 1-6% (w/w), such as 1.5-6% (w/w), to ensure the injectability in most cases. The water content may be calculated or adjusted accordingly, for example by summing up the percentages of nanofibrillar cellulose and pharmaceutical component, and possibly other solvents and/or any additives, wherein the rest may be water.

One embodiment provides an injectable pharmaceutical formulation, preferably for subcutaneous, intradermal or intramuscular administration, comprising
nanofibrillar cellulose hydrogel having a water content in the range of 82-98.9% (w/w), such as 90-98.9% (w/w), preferably having a content of nanofibrillar cellulose in the range of 1-8% (w/w), and
a pharmaceutical compound, wherein the nanofibrillar cellulose has an average fibril diameter of 200 nm or less, such as in the range of 1-200 nm.

However, it is possible to include solvents for modifying the release profile of the pharmaceutical compound. Suitable solvents include organic solvents, such as dimethyl sulfoxide (DMSO) and/or N-methyl-2-pyrrolidone (NMP), which may be used to increase release of the pharmaceutical compound from the formulation.

In one embodiment the composition contains organic solvent, such as dimethyl sulfoxide and/or N-methyl-2-pyrrolidone, such as in an amount of 5-55% (w/w), for example 5-20% (w/w), 5-30% (w/w), 10-40% (w/w), 20-50% (w/w) or 30-50% (w/w). The composition may be prepared by adding such solvent and combining with nanofibrillar cellulose dispersion, and combining with the pharmaceutical compound either simultaneously or later. The pharmaceutical compound may be provided in the organic solvent.

In one embodiment the nanofibrillar cellulose is chemically unmodified nanofibrillar cellulose. In one embodiment the composition, especially when the nanofibrillar cellulose is chemically unmodified nanofibrillar cellulose, has a content of nanofibrillar cellulose in the range of 1-3% (w/w), such as 1-2% (w/w).

In one embodiment the nanofibrillar cellulose is anionically modified nanofibrillar cellulose. It was found out that compared to other types of nanofibrillar cellulose, anionically modified nanofibrillar cellulose provided better mechanical properties, such as three-dimensional gel forming properties, which are advantageous in injectable or implantable extended-release compositions. Anionically modified nanofibrillar cellulose also provided a higher initial burst of the pharmaceutical compound, which is desired in most therapies.

In one embodiment the composition, especially when the nanofibrillar cellulose is anionically modified nanofibrillar cellulose, has a content of nanofibrillar cellulose in the range of 4-8% (w/w), such as 4-7% (w/w) or 5-7% (w/w). In one embodiment the composition has a content of anionically modified nanofibrillar cellulose in the range of 1.5-6.5% (w/w). These consistencies of anionically modified NFC enable providing the desired initial burst of the pharmaceutical. In some cases lower consistencies may be desired to obtain desired injection properties for a variety of uses or for specific uses, such as 1.5-5% (w/w), 1.5-4% or 1.5-3.5% (w/w).

In one embodiment the nanofibrillar cellulose, when dispersed in water, provides a zero shear viscosity in the range of 1000-100000 Pa·s, such as in the range of 5000-50000 Pa·s, and a yield stress in the range of 1-50 Pa, such as in the range of 3-15 Pa, determined by rotational rheometer at a consistency of 0.5% (w/w) by weight in aqueous medium at 22° C.±1° C. and/or wherein the nanofibrillar cellulose has an average fibril diameter of 200 nm or less, such as in the range of 1-200 nm.

The amount of the pharmaceutical compound per dose and the size of the dose may vary. Examples of carprofen doses per day include a high dose range comprising about 5 mg carprofen per 1 ml injection and a low dose range comprising about 0.25 mg carprofen per 0.1 ml injection, which may be administered twice a day, or about 0.5 mg carprofen per 0.2 ml injection. Examples of meloxicam doses per day include a high dose range comprising about 2 mg meloxicam per 1 ml injection and a low dose range comprising about 0.2 mg meloxicam per 0.1 ml injection, which may be administered twice a day, or 0.4 mg meloxicam per 0.2 ml injection.

A daily total dose, such as for a depot, may be for example in the range of 0.05-10 mg per day depending on the compound, such as 0.05-5 mg, 0.05-2 mg, 0.05-1.5 mg, 0.1-5 mg, 0.1-2 mg, or 0.1-1.5 mg, which may be administered in one, two or more doses. A volume of a single dose may be in the range of 50 µl-2 ml, such as 100 µl-1 ml or 100-500 µl. A daily dose may be in the range of 0.5-5 mg/kg, such as 2-5 mg/kg, for rodents, such as rats and/or mice.

In one example the content of the pharmaceutical compound is in the range of 0.5-10 mg, such as is in the range of 0.1-10 mg, 0.2-10 mg, or 0.5-10 mg, for example is in the range of 3-10 mg or 1-7 mg, per 100 µl of the injectable pharmaceutical formulation. In one example the content of the pharmaceutical compound is in the range of 0.5-10 mg, such as is in the range of 0.1-10 mg, 0.2-10 mg, or 0.5-10 mg, for example is in the range of 3-10 mg or 1-7 mg, per 100 mg of the injectable pharmaceutical formulation. In one example the content of the pharmaceutical compound is in the range of 0.1-50 mg per 1 g of the injectable pharmaceutical formulation Lower amounts may be provided, such as in the range of 0.1-5 mg, 0.2-5 mg, 0.1-2 mg, 0.2-2 mg or 0.2-1 mg, which may be suitable for small animals, such as small rodents, for example for mice.

The content of the pharmaceutical compound may be in the range of 0.1-10% (w/w), 0.2-10% (w/w) or 0.5-10% (w/w) of the pharmaceutical formulation. In one example the content of the pharmaceutical compound is in the range of 3-10% (w/w) or 1-7% (w/w). Lower amounts may be provided, such as in the range of 0.1-5% (w/w), 0.2-5% (w/w), 0.1-2% (w/w), 0.2-2% (w/w) or 0.2-1% (w/w).

When the nanofibrillar cellulose was used as matrix for the pharmaceutical compound, it could stabilize the compound and prevent the precipitation of the compound, so that the compound remained in a dispersion. The dissolution rate of the compound was increased, which can enhance the delivery of the compound into a subject. In this way it was possible to improve the dissolution and bioavailability of poorly water-soluble pharmaceuticals in dosage forms such as injectables and implants, and simultaneously provide the extended release of the compound.

The pharmaceutical compound may be any suitable pharmaceutical compound. The pharmaceutical compound may or may not comprise one or more of anti-tumor, anti-cancer, anti-bacterial, such as antibiotic, anti-viral, anti-inflammatory, anti-allergic and analgesic compound(s) or agent(s). In one embodiment the pharmaceutical compound comprises or is an analgesic compound, i.e. a painkiller, such as an opioid or a nonsteroidal anti-inflammatory drug (NSAID). Examples of such compounds include meloxicam, carprofen, metamizole/dipyrone and buprenorphine. Analgesics are suitable because they benefit from the dissolution profile provided by the present formulations.

The present composition may be provided to enhance the solubility and bioavailability of the pharmaceutical compound, which is beneficial especially for pharmaceuticals having a limited solubility in water.

The pharmaceutical compound may be fully or partly water-soluble. It may have limited or low solubility in water and/or low bioavailability. The pharmaceutical compound may have a water-solubility of down to 0.001 mg/ml, or more than 0.001 mg/ml, at 25° C. The pharmaceutical compound may have a solubility in water of more than 0.01 mg/ml at 25° C., more than 0.1 mg/ml at 25° C., more than 0.2 mg/ml at 25° C., or more than 1 mg/ml at 25° C., such as more than 3 mg/ml at 25° C. Including a compound having a limited water solubility to nanofibrillar cellulose matrix may enhance the solubility and/or enable including more compound. The bioavailability of the compound is also increased. However, at the same time the nanofibrillar cellulose may be provided at high water content.

The pharmaceutical compound(s) with limited or low solubility in water, as disclosed in previous, may be present as aggregates and/or as particles having an average diameter of more than 50 nm, such as more than 70 nm, or more than 100 nm, even more than 200 nm or more than 500 nm. These particles or aggregates are stabilized by the nanofibrillar cellulose, and the bioavailability thereof is enhanced. The size and shape of the nanoparticles can be detected from the final product microscopically. The poorly water soluble compounds may be present in crystalline or mainly crystalline form.

They may not be present in amorphous state and/or in the form of nanoparticles formed in a nucleation process in a nanofibrillar cellulose dispersion.

Examples of pharmaceutical compounds with limited water-solubility include buprenorphine having a solubility of 0.0168 mg/ml (16.8 µg/ml), meloxicam having a solubility of 0.00715 mg/ml (7.15 µg/ml), and carprofen having a solubility of 0.00379 mg/ml (3.79 µg/ml), in water at 25° C.

One or more of the above, and/or other pharmaceutical compound(s) may be included in the pharmaceutical formulations described herein. The pharmaceutical formulation may be provided in a suitable solvent, which may be water or other than water, such as organic solvent, or aqueous solution, dispersion or emulsion containing solvent such as organic solvent. The solvent may be for example ethanol, such as anhydrous ethanol. Especially pharmaceutical compounds having a limited water-solubility may be provided in a solvent capable of solving the compound at least partly, which may be organic solvent or a mixture of water and organic solvent. Examples of organic solvents include methanol, ethanol, 1-propanol, 2-propanol, 1-butanol, 1-octanol, propylene glycol, toluene, acetone, 1,4.dioxane, ethyl acetate, isopropyl myristate, acetonitrile, chloroform, n-hexane, cyclohexane, dimethyl sulfoxide (DMSO), N-methyl-2-pyrrolidone (NMP), dimethyl formamide (DFM) and mixtures thereof.

The pharmaceutical compound, which may be in a suitable solvent, may be combined with the aqueous dispersion of nanofibrillar cellulose in mixing, such as by using a mixer, agitator, disperser, homogenizer, or the like device, which may be also used for treating the nanofibrillar cellulose.

The present composition may be used to provide a relatively short drug release, or on the other hand to provide a slow and even drug release, or a combination thereof. The homogeneity of the nanofibrillar cellulose, especially wood cellulose and/or completely homogenized and fibrillated material, enable obtaining such controlled slow and even release.

In one example it is better to have a large portion of the drug released during day 1, such as about 30%, for example 20% or more, or 25% or more. It may be desired to have quite minor release during days 4-7, cumulative release being for example over 55%, preferably over 70%.

Another example aims to slow down and to obtain an even drug release, such as for at least 3-14 days. The pharmaceutical formulation may be formulated or configured to provide a desired sustained release of the pharmaceutical compound in the target or in the subject.

In one embodiment the injectable pharmaceutical formulation is sustained release injectable pharmaceutical formulation, such as for providing a sustained release of the pharmaceutical compound in 3-14 days, for example wherein at least 18% (w/w) of the pharmaceutical compound is released in 3-14 days, such as at least 25% (w/w).

In one embodiment the injectable pharmaceutical formulation is sustained release injectable pharmaceutical formulation for providing a sustained release of 20-40% (w/w) of the pharmaceutical compound during the first day, such as during first 6-12 hours. In one example 5-20%, such as 5-15%, of the compound is released during first 6 hours. Preferably the subsequent release is relatively minor, such as wherein the subsequent cumulative release during days 4-7 is 55% or more, such as 70% or more.

The injectable composition may be provided for use for providing a sustained release of a pharmaceutical compound when injected to a subject. The composition may be provided for use for providing the sustained release disclosed in previous.

One example provides an injectable pharmaceutical formulation comprising
  anionically modified nanofibrillar cellulose hydrogel having a content of nanofibrillar cellulose in the range of 4-8% (w/w) or in the range of 1.5-6.5% (w/w), wherein the nanofibrillar cellulose has an average fibril diameter of 200 nm or less, such as in the range of 1-200 nm, and
  a pharmaceutical compound comprising an analgesic compound,
preferably the formulation having a storage modulus of 350 Pa or more, and a yield stress/fracture strength of 25 Pa or more, such as a storage modulus in the range of 350-5000 Pa and yield stress in the range of 25-300 Pa, determined by stress controlled rotational rheometer with gradually increasing shear stress in a range of 0.001-100 Pa at a frequency 10 rad/s, strain 2%, at 25° C. Such formulations can provide very high initial burst, which is desired for the rapid onset of analgesic treatment. Such as formulation may provide a sustained release of 20-40% (w/w) during the first day, such as during first 6-12 hours, for example a sustained release of 5-20%, such as 5-15% during first 6 hours.

The present application provides the injectable pharmaceutical packed in a syringe. The present application provides a syringe containing the injectable pharmaceutical formulation. The present application also provides in implant containing the pharmaceutical formulation.

The present application provides the injectable pharmaceutical formulation for use for injecting a pharmaceutical compound to a subject, such as an animal, preferably with a needle into a tissue of the subject. The animal may be for example a laboratory animal, such as a rodent, for example a mouse or a rat, a rabbit, a chicken, a pig, a sheep, a bovine or other suitable animal. The tissue may be for example muscle tissue, fat tissue or any suitable subcutaneous or intradermal tissue. "Into" as used herein refers to injecting though skin by using an injection needle or the like suitable penetrating means. Application by a syringe onto skin or other tissue may be excluded.

The present application provides the injectable pharmaceutical formulation for use for providing a sustained release of a pharmaceutical compound in a subject, such as an animal.

Nanofibrillar Cellulose

The starting material for forming the hydrogel is nanofibrillar cellulose, also called as nanocellulose, which refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water. Nanofibrillar cellulose production techniques may be based on disintegrating fibrous raw material, such as grinding of aqueous dispersion of pulp fibers to obtain nanofibrillated cellulose. After the grinding or homogenization process, the obtained nanofibrillar cellulose material is a dilute viscoelastic hydrogel.

The obtained material usually exists at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material. An example of commercially available nanofibrillar cellulose hydrogel is GrowDex® by UPM.

Because of its nanoscale structure nanofibrillar cellulose has unique properties which enable functionalities which cannot be provided by conventional non-nanofibrillar cellulose. It is possible to prepare materials and products which exhibit different properties than conventional products or products using conventional cellulosic materials. However, because of the nanoscale structure nanofibrillar cellulose is also a challenging material. For example dewatering or handling of nanofibrillar cellulose may be difficult.

The nanofibrillar cellulose may be prepared from cellulose raw material of plant origin, or it may also be derived from certain bacterial fermentation processes. The nanofibrillar cellulose is preferably made of plant material. The raw material may be based on any plant material that contains cellulose. In one example the fibrils are obtained from non-parenchymal plant material. In such case the fibrils may be obtained from secondary cell walls. One abundant source of such cellulose fibrils is wood fibres. The nanofibrillar cellulose may be manufactured by homogenizing wood-derived fibrous raw material, which may be chemical pulp. Cellulose fibers are disintegrated to produce fibrils which have an average diameter of only some nanometers, which may be 200 nm or less in most cases, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonas* or *Alcaligenes*, preferably of the genus *Acetobacter* and more preferably of the species *Acetobacter xylinumor* or *Acetobacter pasteurianus*.

It was found out that nanofibrillar cellulose obtained from wood cellulose is preferable for medical or scientific products described herein. Wood cellulose is available in large amounts, and the preparation methods developed for wood cellulose enable producing nanofibrillar materials suitable for the products. The nanofibrillar cellulose obtained by fibrillating plant fibers, especially wood fibers, differs structurally from nanofibrillar cellulose obtained from microbes, and it has different properties. For example compared to bacterial cellulose, nanofibrillated wood cellulose is homogenous and more porous and loose material, which is advantageous in medical applications. Bacterial cellulose is usually used as such without similar fibrillation as in plant cellulose, so the material is different also in this respect. Bacterial cellulose is dense material which easily forms small spheroids and therefore the structure of the material is discontinuous, and it is not desired to use such material in the medical applications, especially when homogeneity of the material is required.

Wood may be from softwood tree such as spruce, pine, fir, larch, douglas-fir or hemlock, or from hardwood tree such as birch, aspen, poplar, alder, *eucalyptus*, oak, beech or acacia, or from a mixture of softwoods and hardwoods. In one example the nanofibrillar cellulose is obtained from wood pulp. The nanofibrillar cellulose may be obtained from hardwood pulp. In one example the hardwood is birch. The nanofibrillar cellulose may be obtained from softwood pulp. In one example said wood pulp is chemical pulp. Chemical pulp may be desired for the products disclosed herein. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical and scientific materials. For example very homogenous nanofibrillar cellulose materials may be prepared without excess processing or need for specific equipment or laborious process steps.

Nanofibrillar cellulose, including the cellulose fibrils and/or fibril bundles, is characterized by a high aspect ratio (length/diameter). The average length of nanofibrillar cellulose (the median length of particles such as fibrils or fibril bundles) may exceed 1 µm, and in most cases it is 50 µm or less. If the elementary fibrils are not completely separated from each other, the entangled fibrils may have an average total length for example in the range of 1-100 µm, 1-50 µm, or 1-20 µm. However, if the nanofibrillar material is highly fibrillated, the elementary fibrils may be completely or almost completely separated and the average fibril length is shorter, such as in the range of 1-10 µm or 1-5 µm. This applies especially for native grades of fibrils which are not shortened or digested, for example chemically, enzymatically or mechanically. However, strongly derivatized nanofibrillar cellulose may have a shorter average fibril length, such as in the range of 0.3-50 µm, such as 0.3-20 µm, for example 0.5-10 µm or 1-10 µm. Especially shortened fibrils, such as enzymatically or chemically digested fibrils, or mechanically treated material, may have an average fibril length of less than 1 µm, such as 0.1-1 µm, 0.2-0.8 µm or 0.4-0.6 µm. The fibril length and/or diameter may be estimated microscopically, for example using CRYO-TEM, SEM or AFM images.

The average diameter (width) of nanofibrillar cellulose is less than 1 µm, or 500 nm or less, such as in the range of 1-500 nm, but preferably 200 nm or less, even 100 nm or less or 50 nm or less, such as in the range of 1-200 nm, 2-200 nm, 2-100 nm, or 2-50 nm, even 2-20 for highly fibrillated material. The diameters disclosed herein may refer to fibrils and/or fibril bundles. The smallest fibrils are in the scale of elementary fibrils, the average diameter being typically in the range of 2-12 nm. The dimensions and size distribution of the fibrils depend on the refining method and efficiency. In case of highly refined native nanofibrillar cellulose, the average fibril diameter, including fibril bundles, may be in the range of 2-200 nm or 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nano-structured materials include "Cellulose microcrystals" (sometimes called as CMC) having a diameter of 10-12 µm and length:diameter ratio (L/D)<2, and "Cellulose microfibrils" having a diameter of 10-100 nm and a length of 0.5-50 µm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and/or diameter (ii) chemical composition, and (iii)

rheological properties. These properties are not necessarily directly dependent on each other. To fully describe a grade, the properties may be used in parallel. Examples of different grades include native (chemically and/or enzymatically unmodified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibrils forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which may be considered as a special case of thixotropic behavior, which means that their viscosity depends on the speed or force by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor disperser, ultrasound sonicator, fluidizer such as microfluidizer, macrofluidizer or fluidizer-type homogenizer.

The disintegration treatment is performed at conditions wherein water is sufficiently present to prevent the formation of bonds between the fibers. A person skilled in the art can adjust the conditions for preparing nanofibrillar cellulose having desired rheological properties and fibrillation degree without undue experimenting, for example by selecting suitable disintegrating equipment, suitable starting material, suitable chemical, physical and/or enzymatic treatment, number of passes and/or energy used in the process as well as the concentration and chemical content of the obtained product.

In one example the disintegration is carried out by using a disperser having at least one rotor, blade or similar moving mechanical member, such as a rotor-rotor disperser, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor disperser the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor disperser is an Atrex device.

Another example of a device suitable for disintegrating is a pin mill, such as a multi-peripheral pin mill. One example of such device includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C. heated if necessary and mixed. A low rotational speed 10 rpm is used. In general Brookfield viscosity may be measured at 20° C.±1° C., at a consistency of 0.8% (w/w) and at 10 rpm.

The nanofibrillar cellulose, for example provided as a starting material in the method, may be characterized by the viscosity it provides in a water solution. The viscosity describes, for example, the fibrillation degree of the nanofibrillar cellulose. In one example the nanofibrillar cellulose when dispersed in water provides a Brookfield viscosity of at least 2000 mPa·s, such as at least 3000 mPa·s, measured at 20° C.±1° C., at a consistency of 0.8% (w/w) and at 10 rpm. In one example the nanofibrillar cellulose, when dispersed in water, provides a Brookfield viscosity of at least 10000 mPa·s measured at 20° 0±1° C., at a consistency of 0.8% (w/w) and at 10 rpm. In one example the nanofibrillar cellulose, when dispersed in water, provides a Brookfield viscosity of at least 15000 mPa·s measured at 20° C.±1° C., at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at 20° C.±1° C., at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average fibril diameter in the range of 1-200 nm, or 1-100 nm. In one example said nanofibrillar cellulose has an average fibril diameter in the range of 1-50 nm, such as 2-20 nm or 5-30 nm. In one example said nanofibrillar cellulose has an average fibril diameter in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

A rheometer viscosity of the nanofibrillar cellulose dispersion may be measured according to one example at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 $s^{-1}$ is exceeded. This method may be used for determining the zero-shear viscosity.

In another example rheological measurements of the hydrogel samples were carried out with a stress controlled rotational rheometer (AR-G2, TA instruments, UK) equipped with 20 mm plate geometry. After loading the samples to the rheometer, 1 mm gap, without dilution, they were allowed to settle for 5 min before the measurement was started. The stress sweep viscosity was measured with gradually increasing shear stress in a range of 0.001-100 Pa at the frequency 10 rad/s, strain 2%, at 25° C. Storage modulus, loss modulus and yield stress/fracture strength can be determined.

It was found out that there is a minimum viscosity level require for hydrogel to retain its shape after the injection. This can be characterized by a storage modulus of 350 Pa or more, and a yield stress/fracture strength of 25 Pa or more determined by stress controlled rotational rheometer with gradually increasing shear stress in a range of 0.001-100 Pa at a frequency 10 rad/s, strain 2%, at 25° C. A person skilled in the art can select suitable preparation method and parameters to obtain such features, even when using different types of starting materials, such as chemically modified or unmodified celluloses.

The nanofibrillar cellulose should have adequate degree of fibrillation so that the desired properties and effects are obtained. In one embodiment the nanofibrillar cellulose has an average diameter of a fibril in the range of 1-200 nm and/or, the nanofibrillar cellulose or the pharmaceutical formulation, when dispersed in water, provides a storage modulus of 350 Pa or more, such as in the range of 350-5000 Pa, or preferably 350-1000 Pa, and yield stress of 25 Pa or more, such as in the range of 25-300 Pa, preferably 25-75 Pa, determined by stress controlled rotational rheometer with gradually increasing shear stress in a range of 0.001-100 Pa at a frequency 10 rad/s, strain 2%, at 25° C.

In one example the nanofibrillar cellulose, for example provided as a starting material in the method, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium at 22° C.±1° C. Such nanofibrillar cellulose may also have an average fibril diameter of 200 nm or less, such as in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at measured at 20° C.±1° C. a consistency of 0.1% (w/w) in aqueous medium, and measured by nephelometry. To characterize the nanofibrillar cellulose these ranges may be combined with the viscosity ranges of the nanofibrillar cellulose, such as zero shear viscosity, storage modulus and/or yield stress.

Nanofibrillar cellulose may be or comprise non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at 20° C.±1° C., at a consistency of 0.8% (w/w) and at 10 rpm. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may comprise chemically modified nanofibrillar cellulose, such as anionically modified nanofibrillar cellulose or cationically modified nanofibrillar cellulose. In one example the nanofibrillar cellulose is anionically modified nanofibrillar cellulose. In one example the anionically modified nanofibrillar cellulose is oxidized nanofibrillar cellulose. In one example the anionically modified nanofibrillar cellulose is sulphonized nanofibrillar cellulose. In one example the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The modifications of nanofibrillar cellulose disclosed herein may also be applied to other fibrillar cellulose grades described herein. For example also highly refined cellulose or microfibrillar cellulose may be similarly chemically or enzymatically modified. However, there are differences for example in the final fibrillation degree of the materials.

In one example such chemically modified nanofibrillar cellulose, when dispersed in water, provides a Brookfield viscosity of at least 10000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 15000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 18000 mPa·s measured at 20° C.±1° C., at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at 20° C.±1° C., at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at 20° C.±1° C., at a consistency of 0.8% (w/w) and at 10 rpm.

In one example the nanofibrillar cellulose comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at 20° C.±1° C., at a consistency of 0.8% (w/w) and at 10 rpm.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion or gel. The auxiliary agents may be also added to the final product, for example by impregnating, spraying, dipping, soaking or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) agents and other agents affecting to the properties of the product or to the properties of the active agents, such as buffers, surfactants, plasticizers, emulsifiers or the like. In one example the dispersion contains one or more salts, which may be added to enhance the properties of the final product or to facilitate water removal from the product in the manufacturing process. Examples of salts include chloride salts, such as sodium chloride, calcium chloride and potassium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired salt content in the final product may be in the range of 0.5-1%, such as about 0.9%, of the volume of the wet product. The salts, buffers and the like agents may be provided to obtain physiological conditions.

Multivalent cations may be included to obtain non-covalent crosslinking of the nanofibrillar cellulose. One example provides a nanofibrillar cellulose product comprising nanofibrillar cellulose, especially comprising anionically modified nanofibrillar cellulose, and multivalent cations, such as multivalent metal cations, for example selected from cations of calcium, barium, magnesium, zinc, aluminum, gold, platinum and titanium, wherein the nanofibrillar cellulose is crosslinked by the multivalent cations. Especially barium and calcium may be useful in biomedical application, and especially barium may be used in labelling and can be used for detecting the injected hydrogel The amount of the multivalent cations may be in the range of 0.1-3% (w/w), for example 0.1-2% (w/w) calculated from the dry content of the hydrogel.

One example provides a method for preparing such a hydrogel, the method comprising providing pulp, disintegrating the pulp until nanofibrillar cellulose is obtained, forming the nanofibrillar cellulose into a hydrogel The nanofibrillar cellulose may be fibrillated into a desired fibrillation degree and adjusted into desired water content, or otherwise modified, so that it forms a gel having desired properties as described herein. In one example the nanofibrillar cellulose in the hydrogel is anionically modified nanofibrillar cellulose.

The hydrogel to be used as a medical or scientific hydrogel needs to be homogenous. Therefore the method for preparing the hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the applications is obtained. The hydrogel may be further sterilized, for example by using heat and/or radiation, and/or by adding sterilizing agents, such as antimicrobials.

Use of the Composition

The compositions or formulations comprising pharmaceutical compound(s) in a nanofibrillar cellulose hydrogel disclosed herein may be used in a variety of methods comprising delivering, injecting, implanting and/or otherwise administering the composition to a subject, such as human or animal subject. The subject may be a patient, especially a patient in need of therapy which involves the pharmaceutical compound(s) included in the composition. It may be necessary to recognize or detect a subject which needs treatment. There may be a specific target in a subject whereto the pharmaceutical is targeted, for example injected. The methods include providing the composition comprising pharmaceutical compound(s) in a nanofibrillar cellulose hydrogel in a suitable form, such as in injectable form or implantable form. Also oral dosage forms may be provided, for example encapsulated in biodegradable capsules, such as soft capsules. The treatment, which may be therapy, may comprise extended-release administration of one or more pharmaceutical compound(s) such sustained-release or controlled-release administration. Analogously the pharmaceutical formulation to be administered may be extended release composition or dosage form, such as sustained-release or controlled-release composition or dosage form. The treatment may comprise analgesic treatment, such as prolonged analgesic treatment, or treatment with one or more other suitable pharmaceutical compound(s), such as compound(s) with low solubility in water. The composition may be used in treatments, which may be therapeutic treatments or methods.

One embodiment provides the injectable formulation for use in a therapeutic method comprising administering the pharmaceutical compound(s) to a subject.

One embodiment provides the implantable formulation for use in a therapeutic method comprising administering the pharmaceutical compound(s) to a subject.

One example provides a method for treating a subject in need of therapy, the method comprising
  preferably recognizing a subject in need of therapy or treatment,
  providing the formulation comprising pharmaceutical compound(s) in a nanofibrillar cellulose hydrogel disclosed herein, and
  delivering or administering the formulation to the subject, for example by injecting or by implanting.

EXAMPLES

Correct dose of analgesic has a pivotal role in preclinical animal studies. The goal of proper postoperative pain management is to minimize pain and discomfort without producing unacceptable adverse effects. Assessing pain in rodents can be difficult as they typically minimize pain-associated behaviours unless the pain is incapacitating. Therefore, pain management in preclinical animal studies must include pharmaceutical intervention. For post-operative pain management for laboratory animals, typical duration of treatment is 2-4 days, whereas for veterinary use relieving chronic pain, the longer the drug release the better the effect for animal. The doses for chronic pain treatments are typically lower compared to post-operative treatment.

Drug and dosage recommendations vary globally and even from institution to institution. The two classes of analgesics typically used to treat postoperative pain in laboratory animals are opioids and NSAIDs (nonsteroidal anti-inflammatory drugs). All of these are suggested treatments for moderate to severe pain, but each of these have very different mechanisms of actions and extent of side effects.

Buprenorphine is the most commonly used opioid in laboratory animal care, whereas carprofen, ketoprofen and meloxicam are widely used anti-inflammatory drugs. The balance between appropriate analgesic and adverse effects is often narrow. Thus, it is extremely important to know what the correct daily dose in animals is and that the dosing method is accurate and stable. The duration of action in opioids and some NSAIDs is relatively short, 6-12 hours, requiring several doses per day. However, common practice in animal laboratories is that it will be given only once or twice a day, which leads to inadequate pain relief.

The efficacy of the analgesic drug is not only dependent on the analgesic compound itself. Formulation stability, bioavailability, release kinetics and injectability are challenges that must be overcome for maximal effectiveness.

Excipients and sustained release technologies offer solutions for these challenges. In preclinical settings, most common method to dose the compound is conventional injection. Few sustained release technologies have been applied. Of these, osmotic pumps, matrix pellets and polymers are most frequently used, but they all have weaknesses that prevent their larger use.

Results and Findings

In this study NFC is provided as an injectable sustained release excipient for analgesic drugs Meloxicam and Carprofen for preclinical research use. Targeted in vivo doses were calculated from typical daily doses administered by injection. Formulations were targeted to rat and mouse, the most commonly used laboratory animals in preclinical research.

Dose response was observed in all low dose formulations. In contrast, dose response was mild or not seen at all in higher doses. This phenomenon is due to fact that the limiting factor is speed of dissolution of API to its environment, which is basically due to poor water solubility of compounds. The speed of dissolution of API to its environment can be speed up by increasing its surface area (=reduction of particle size by micronizing or nanonization) or by increasing matrix volume in injections. At higher doses also cumulative release was poor, indicating that unreleased compound is remaining in the depot or elsewhere in the dissolution system.

When considering the applicability of the API-NFC gels as post-operative analgesic for the research animals the optimal formulations must release all active ingredient (close to 100% cumulative result) within 3-7 days, and most of the compound within first 2-4 days. Longer release might lead to overdose of analgesics and adverse effects. Ineffective pain relief following surgery may cause chronic pain syndromes. Overall, poorly controlled pain management may both adversely impact the welfare of laboratory animals and confound the interpretation of experimental results. The cumulative release was not 100% in any of the formulations despite the fact that the release decreased closed to zero within two weeks in most of the formulations. Partly this is because some of the API compound is still in the depot but partly because some of the API has been lost in the dissolution system, such as attached in the pouches or during the dissolution media change. The highest cumulative releases were between 80-90% which seems to be the maximum in the dissolution system used in this study.

Some CPF and MLX low dose range formulations fulfilled targeted dosage level for mice post-operative pain treatment. Initial burst was not too high, releasing approximately 5-10% of the API within first 6 hours and most of the API was released within 4 days. Optimal doses can be achieved by using either existing formulations with current injection volumes or with slightly bigger volumes or repeated injections. 6% Anionic NFC formed clear 3D gel and kept better its shape after injection compared to 2% anionic and 1.5% native NFC forms, which is due to lesser amount of water in the formulation. There were no major differences in the release profiles between the three forms of NFC. However, 6% Anionic NFC had strongest initial burst suggesting highest bio-availability and fastest analgesic action. For the commercial use, long-term stability needs attention. After the project it was observed that native NFC was partly frozen in the refrigerator and after thawing water and NFC were clearly separated and were not mixed easily. All these might be important phenomena for the in vivo use and thus they support the selection of 6% anionic gel for the further studies.

REFERENCES

When considering the use of PVA as reference matrix the concern was that as PVA is water soluble it will leak from dissolution pouches. PVA in water as such, was rapidly leaked from dissolution pouches. High molecular weight PVA was successfully formulated by cross-linking it with oxalic acid to present more 3D structure and appropriate for the dissolution studies. However, PVA was difficult to handle as it required laborious cross-linking procedure. In the in vitro setting it caused challenges for the measurement analytics as dissolved polymer blocked HPLC-column.

Reference matrices PLGA/DMSO gel and PVA/$H_2O$ gel showed sustained release profiles, but they lacked some vital beneficial properties compared to NFC gels when considering post-operative pain management indication. PLGA had overall too low release rates and too low cumulative release. PVA had higher and close to target dose release rates but excluding initial burst and also too low cumulative release.

PVA can be considered as biodegradable matrix compared to NFC and PLGA matrices which are biostable and non-dissolvable in water and in vivo in animals. This difference has importance when considering final indications. For the laboratory animals biostable and biodegradable matrices can both be used, but for the veterinary use, high volume and frequent injections of biostable matrix might cause contraindication for the use, because of the accumulation of matrix in subcutaneous cavity.

In the in vivo settings sustained release meloxicam has been used in the USA and some labs in Europe (Meloxicam-SR, Zoopharm Inc). Recent article summarizes poor outcome of that product. In the article a pilot study evaluating the efficacy and blood levels of Meloxicam-SR using the manufacturer's recommended dosing of 4 mg/kg per 72 h was carried out. They observed that mice exhibited signs of pain and plasma drug levels were undetectable 4 h after dosing and that Meloxicam-SR failed to deliver adequate pain control at the currently recommended dosing. When comparing NFC-API findings of this study to SR-meloxicam study carried out in the article, a better outcome in vivo for the NFC-API formulations can be obtained.

SUMMARY

The objective of this study was to develop nanofibrillar cellulose (NFC) gel as a sustained release excipient for analgesic drugs for preclinical research use. Selected analgesic drugs were Meloxicam (MLX) and Carprofen (CPF). Selected reference matrices for NFC were polyvinyl alcohol (PVA) and poly(lactic)-co-glycolic acid (PLGA). The study included several phases; Dissolution feasibility phase for PVA, Cumulative release phase and Extensive dissolution phase. The study aimed to support conclusion which form of NFC, anionic or native (chemically unmodified), is better sustained release excipient and which indication, short-term post-operative pain management (for 2-4 days) or long-term chronic pain management (for 1-4 weeks) seems more promising indication area.

Targeted in vivo doses were calculated from typical daily doses administered by injection. Formulation included three doses and two dose ranges, low and high dose, targeting mouse and rat, the most commonly used laboratory animals in preclinical research. The length of extensive dissolution phase was two weeks with frequent sampling points.

The results of the PVA feasibility study suggested, that by using oxalic acid as a cross-linker PVA forms 3D gel-structure appropriate for the dissolution studies and therefore both reference materials, PVA/$H_2O$ gel and PLGA/DMSO gel, were included in the extensive dissolution study. In the cumulative release studies was observed that 50% DMSO (dimethyl sulfoxide) and 50% NMP (N-methyl-2-pyrrolidone) increased the release of CPF. Of these, DMSO was included in the high dose CPF formulations.

Based on the extensive dissolution study, selected doses of Carprofen (CPF) and Meloxicam (MLX) showed sustained release for 3-14 days from NFC formulations. The dose response was observed in all low dose formulations, but not in high dose formulations, suggesting that the speed of dissolution of API to its environment is a limiting factor. CPF and MLX formulations to achieve target doses for mouse post-operative pain treatment were identified and studied. Optimal formulations concomitantly have high cumulative release, indicating good formulation for post-operative pain treatment in mice. Optimal doses can be achieved by using either existing formulations with current injection volumes or slightly bigger volumes. Formulations at the target level were for e.g. 6% anionic NFC with 0.5 mg CPF in 100 µl injection and 6% anionic NFC with 0.1-0.2 mg MLX in 1-2×100 µl injection. These formulations have high initial burst, which is desired for the rapid onset of analgesic treatment. High initial burst is short and releases only 5-10% of the total dose within first 6 hours.

50% DMSO increased the release of CPF in the cumulative release dissolution study. The increase was most apparent within the first day of the study after which similar release as pure NFC was obtained. Despite the higher release at early time points, the cumulative release remained still low at the extensive 14-day dissolution study. CPF and MLX formulations to achieve target doses for rat post-operative pain treatment cannot be easily achieved with current formulations. Low cumulative release values during two weeks with high dose formulation, indicate potentially good formulation for chronic pain, such as arthritis, treatment and sustained release even up to several weeks.

Based on feasibility and dissolution tests both forms of NFC, native and anionic form, can be used as excipient for analgesic compounds, however, 6% anionic form has some beneficial properties over the other NFC forms, such as better 3D gel forming properties and higher initial burst. Reference matrices PLGA/DMSO gel and PVA/$H_2O$ gel showed sustained release properties. The release profile of PVA was similar to NFCs excluding initial burst, whereas release from PLGA was very low after initial burst. NFC gels were superior compared to reference matrices when considering post-operative pain management indication. PLGA/DMSO gel had overall too low release rates and too low cumulative release. PVA/H$_2$O gel had higher and close to target dose release rates, but also too low cumulative release for short-term release products. PVA was difficult to handle as it required laborious cross-linking procedure after which API suspendability was challenging.

Based on this study, nanofibrillar cellulose gel is a promising sustained release excipient for analgesic drugs carprofen and meloxicam for preclinical research use or veterinary use. The formulation of actives with NFC was feasible by using dual asymmetric centrifugal mixing, agglomerates were broken with metal spheres in the mixing cup. All NFC's, but particularly 6% anionic NFC with CPF or MLX can be used as excipient for post-operative pain management for 2-4 days for mice and with some limitations for rats. All NFC's have the potential be used as excipient for chronic pain management for over 2 weeks for rats and larger animals and with some limitations for mice.

Objective

The objective of this study was to develop nanofibrillar cellulose gel as a sustained release excipient for analgesic drugs for preclinical research use. Study included several phases, with specific attention to the following design features:
1. To evaluate compatibility of polyvinyl alcohol (PVA) as reference matrix for NFC for in vitro dissolution use based on physico-chemical properties (Dissolution feasibility phase, PVA)
2. To study cumulative release of MLX and CPF aiming to receive close to 100% cumulative result within 7 days (Cumulative release phase)
3. To design and perform extensive dissolution study for NFC and reference matrices—API depots (Extensive dissolution phase)
4. To conclude which form of NFC, anionic or native, is better sustained release excipient and which indication, short-term post-operative pain management (for 2-4 days) or long-term chronic pain management (for 1-4 weeks) seems more promising indication area Targeted in vivo doses were calculated from typical daily doses administered by injection. Formulation included three doses and two dose ranges, low and high dose, targeting mouse and rat, the most commonly used laboratory animals in preclinical research. The length of extensive dissolution phase was two weeks with frequent sampling points.

Compounds and Matrix Materials
Carprofen (CPF), NSAID
CAS 53716-49-7, Formula C$_{15}$H$_{12}$ClNO$_2$
Molecular weight 273.71 g/mol
Manufacturer: Hyperchem, solid powder, purity 99%
Mp.=195-199° C.
Lot 00301A
Meloxicam (MLX), NSAID
CAS 71125-38-7, Formula C$_{14}$H$_{13}$N$_3$O$_4$S$_2$
Molecular weight 351.40 g/mol
Manufacturer: Hyperchem, solid powder, purity 98.0%
Mp.=254° C.
Lot 170616001
Nanofibrillar cellulose gels were obtained from UPM. Three forms of NFC were obtained for testing: 6% anionic form (lot 11944), 2% anionic form (lot 12066) and 1.5% native form (lot 11992). The cellulose was disintegrated into desired fibrillation degree and the anionic form was oxidized. Reference matrices, polyvinyl alcohol (PVA) and poly(lactic-co-glycolic acid (PLGA) were obtained from Sigma Aldrich Co. Two molecular weight hydrolyzed PVA's were obtained: Low molecular weight: MW Avg. 40.000 (31.000-50.000, cat no 363138, lot MKCG6270) and high molecular weight: MW 130.000 (cat no 563900, lot MKCB5273). One form of acid terminated PLGA was obtained: MW Avg 12.000 (7.000-17.000, Resomer® RG 502, cat no 719897, lot no BCBX6534). The test compounds and matrix components were handled and stored according to instructions obtained from the manufacturer.

Study Design

Dissolution Feasibility, PVA

Evaluation of polyvinyl alcohol (PVA) as reference matrix for NFC for in vitro dissolution use based on physico-chemical properties. In the extensive dissolution study, reference matrices were both, PVA and PLGA, as the results of the dissolution feasibility study for PVA were supportive. Following detailed tasks were performed:

Evaluation of PVA gel forms for in vivo and in vitro use based on physico-chemical properties Mixing tests with H$_2$O and PVA gel forms Mixing test with TiO$_2$ powder to ensure homogenous mixing Evaluation of dissolution properties at RT and 37° C. by using TiO$_2$ as a placebo marker, monitoring release/leakage of TiO$_2$ with PVA gels Syringeability of the PVA gels from syringe and needle Cross-linking test with physical (freeze-thaw) and chemical (oxalic acid) agents to improve sustained release properties of PVA Pilot dissolution of PVA with API (CPF)

Cumulative Release Phase

Cumulative release study aiming to increase the release rate of CPF and receive close to 100% cumulative result for NFC-formulations within 7 days. Following detailed tasks were performed:

Two solvents, DMSO (Dimethyl sulfoxide) and NMP (N-methyl-2-pyrrolidone), in addition to H$_2$O were used to enhance release of CPF 6% anionic and 1.5% native NFC were studied Study included formulation and short in vitro dissolution studies for NFC-API depots to follow cumulative release Extensive Dissolution Extensive dissolution for Carprofen (CPF) and Meloxicam (MLX) with NFC and reference matrices. Following detailed tasks were performed:

Extensive in vitro dissolution test for NFC-API and reference matrix-API depots based on earlier experiments Includes three API doses, two replicates, three different forms of NFC gel (native 1.5%, 2% anionic and 6% anionic) and reference matrices PVA (polyvinyl alcohol) and PLGA (poly(lactic-co-glycolic acid, Resomer (RES))

Two dose ranges, low dose targeting for mouse and high dose targeting for rat timepoints: 2 h, 6 h, day 1, day 2, day 4, day 7, day 10 and day 14

TABLE 1

| Targeted doses of CPF and MLX for mouse and rat. API | Carprofen | Carprofen | Meloxicam | Meloxicam |
|---|---|---|---|---|
| Abbrev | CPF | CPF | MLX | MLX |
| Intended animal species | Mouse | Rat | Mouse | Rat |
| Daily dose (mg/kg), injection | 5 | 5 | 3-5 | 1-2 |
| Weight of young animal (g) | 20-25 | 250-300 | 20-25 | 250-300 |
| Dose (mg per day) | 0.100-0.125 | 1.250-1.500 | 0.060-0.125 | 0.250-0.600 |
| Duration of drug release (d), post-operative pain | 2-4 | 2-4 | 2-4 | 2-4 |
| Dose range/depot (mg) | 0.200-0.500 | 2.500-6.000 | 0.120-0.500 | 0.500-2.400 |

Manufacturing API Depots and Dissolution Phase

Briefly, CPF and MLX were weighed after grinding and dispersed separately in the NFC or reference matrices by Dual Asymmetric Centrifugation (2500 rpm, 1 min in pp10 cup, SpeedMixer™ model 150/250). PLGA was first dissolved in DMSO (40/60) and 10% PVA in UP-H2O (90° C., 30 min). In addition, prior to API addition PVA was treated with 1% oxalic acid (110° C., 120 min). Obtained API-matrix suspensions were injected with 1 ml syringe and 21G needle at injection volume of 100-300 µl. Depots were injected into sealed cellulose pouches with 5-8 µm porosity (F58, Ankom Technologies) with metal spring inside to keep the pouch slightly open, mimicking subcutaneous space in vivo. The dissolution set-up is shown in FIGS. 1A-D.

In vitro dissolution test was performed for each API depot separately. Dissolution studies were performed in 100 ml glass vials where cellulose pouch was placed inside loose metal grid, which kept the pouch under the dissolution liquid surface concomitantly allowing free circulation of fluids. Glass vials were placed in orbital shaker (60 rpm at +37° C., dark). Dissolution solution was 0.9% NaCl. Sampling timepoints in the extensive dissolution study included study days: 2 h, 6 h, day 1, day 2, day 4, day 7, day 10 and day 14. At each timepoint all fluid was changed after sampling.

HPLC Measurements

High Performance Liquid Chromatography (HPLC) were performed by using HPLC-UV equipment (Agilent 1200 series). Stock solutions of compound standards were prepared in eluents at appropriate concentrations for each compound. All standards were stored in a refrigerator at +4° C. throughout the study. Samples for compound quantification were collected from the dissolution vial at several time points according to the prescheduled plan. Samples were collected into glass HPLC vials and were left in dark at +4° C. before analyses. 120 EC-C18 column (50 mm long, 3.0 mm ID, 4.0 µm particle size) and guard column was used in the study. The calculations for the quantitation were based on peak area ratios of the unknown samples and the standards. The peak data from the HPLC-UV analyses were collected, integrated and analyzed using OpenLAB CDS ChemStation software. The standard curves were generated using linear regression.

Selected Conditions for Measurements:

CPF (Carprofen)

Eluent: 50% acetonitrile—49% UP-H$_2$O-1% acetic acid

Flow rate 0.5 ml/min, injection volume 10 µl, UV 260 nm, retention time ~2.1 min, column temp. 30° C.

Typical standard curve and measured API-peak were used for determining the results MLX (Meloxicam)

Eluent: 70% methanol—30% UP-H$_2$O, pH 2.6, adjusted with phosphoric acid

Flow rate 0.3 ml/min, injection volume 10 µl, UV 230 nm, retention time ~2.0 min, column temp. 30° C.

Typical standard curve and measured API-peak were used for determining the results Results Dissolution Feasibility, PVA First experiments demonstrated that both forms of PVA, high and low molecular weight, do not form clear 3D gels when dissolved in water. Highest concentrations to maintain syringeability through 21G needle were 12% water solution for high molecular weight and 16% water solution for low molecular weight PVA. Both highest concentrations leaked from dissolution pouches, low molecular weight PVA within few minutes and high within few hours (FIG. 1). Cross-linking with repeated freeze-thaw cycles produced more gel-like structure, but better formation of hydrogel was observed with 1% oxalic acid treatment and 10% PVA. Higher oxalic acid treatments increased further viscosity of the gel, but decreased syringeability. Despite the 3D gel structure after cross-linking, low molecular weight PVA was leaked from the dissolution pouches within one hour, whereas high molecular weight PVA seemed to remain mainly inside pouches (FIG. 1).

Figure 2:
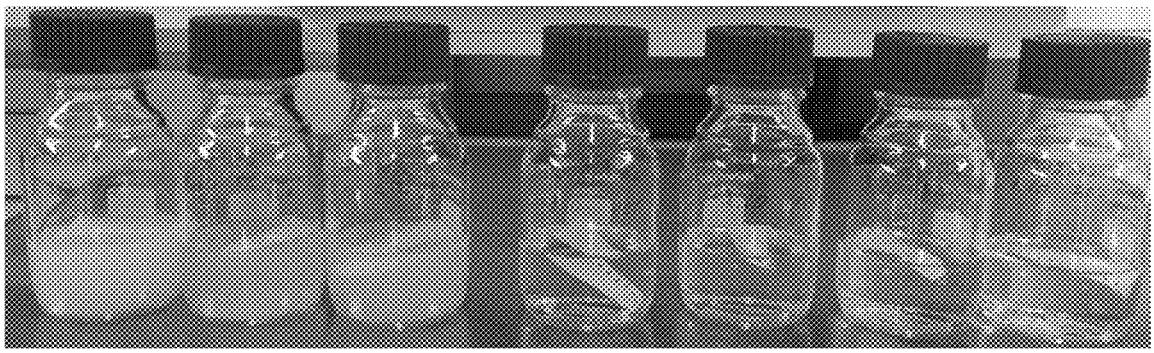
FIG. 2 shows PVA/$TiO_2$ leakage after 1 hour in dissolution study with native and cross linked PVAs. 10% high molecular weight PVA with 1% oxalic acid cross-linking kept most of the matrix inside pouches several days. Short dissolution test was performed with CPF to see if mild leakage will block HPLC columns and whether API can be analyzed. The samples from the left are 1) 10% low mw PVA, no oxalic acid, 2) 10% low mw PVA, 5% oxalic acid, 3) 10% low mw PVA, 20% oxalic acid, 4) Control, 10% low mw PVA, no oxalic acid, no $TiO_2$, 5) 10% high mw PVA, no oxalic acid, 6) 10% high mw PVA, 5% oxalic acid, 7) 10% high mw PVA, 20% oxalic acid.
Figure 3A:
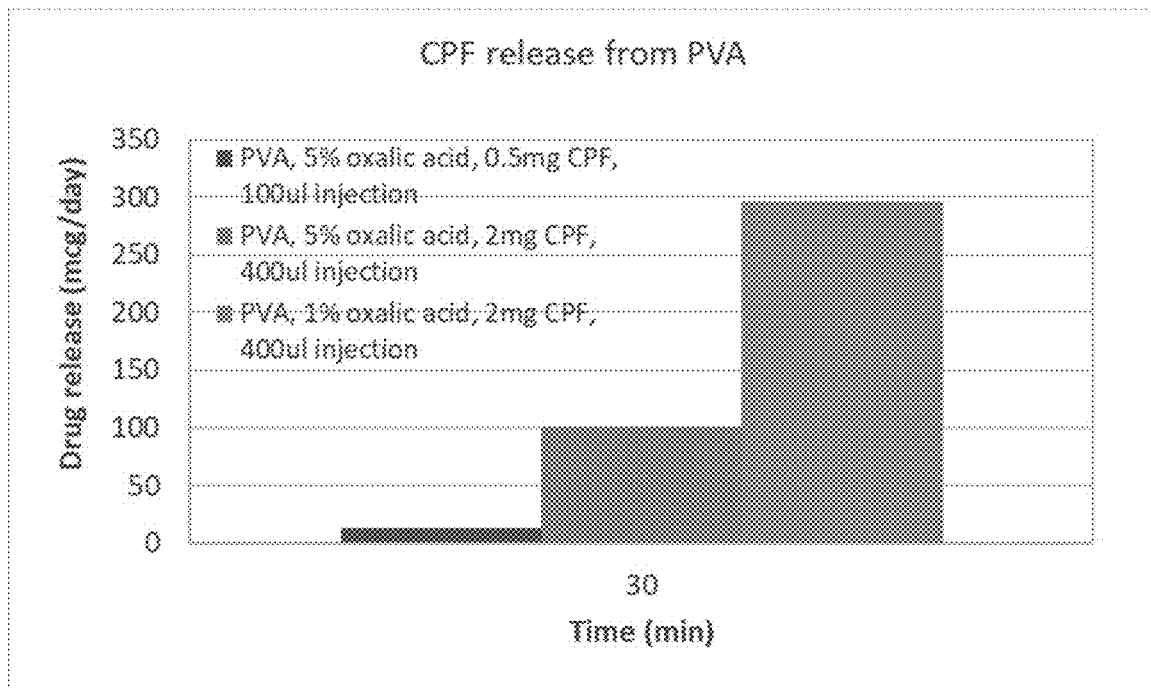
FIG. 3A shows CPF release from 10% high molecular weight PVA with 1% or 5% oxalic acid cross-linking at 30 min timepoint.
Figure 3B:
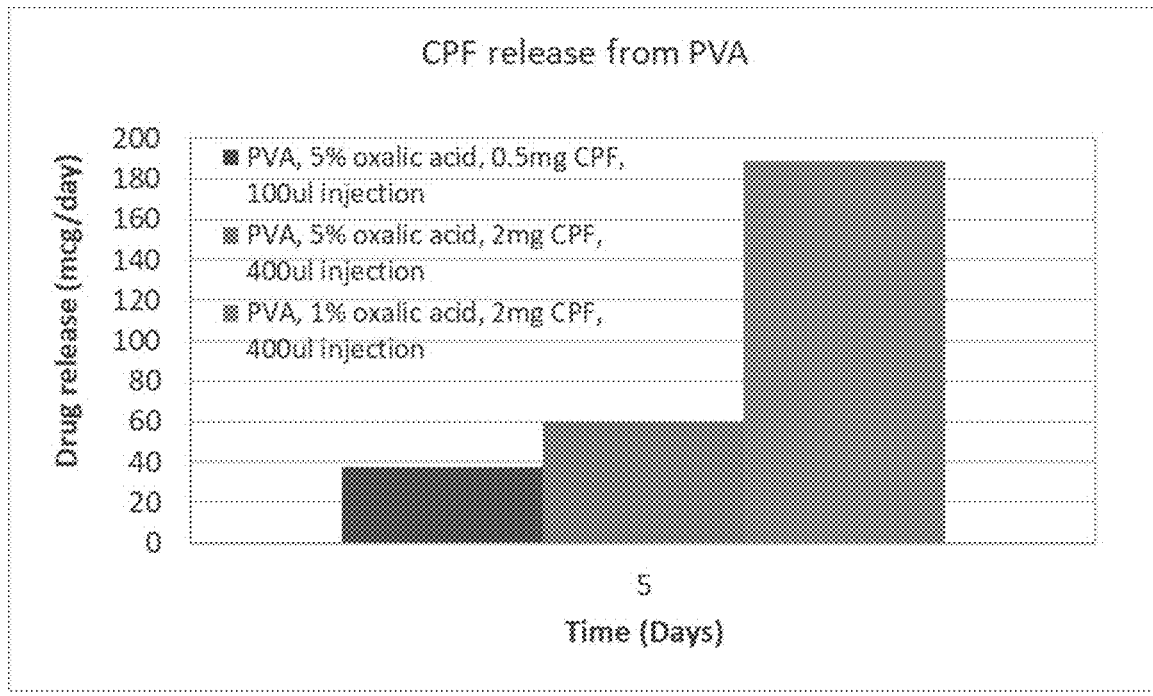
FIG. 3B CPF release from 10% high molecular weight PVA with 1% or 5% oxalic acid cross-linking at day 5.

FIG. 2 shows PVA/TiO$_2$ leakage after 1 hour in dissolution study with native and cross linked PVAs. FIG. 3 shows CPF release from 10% high molecular weight PVA with 1% or 5% oxalic acid cross-linking. A) Release at 30 min timepoint and B) release at day 5.

The results demonstrated that dose-response can be observed between two doses (0.5 mg and 2 mg) and increased cross-linking by oxalic acid (from 1% to 5%) further increases sustained release properties. However, syringeability is limited with 5% cross-linking formulations and therefore, 1% oxalic acid cross-linking was selected for further formulations.

Cumulative Release Study

Figures 7E, 7F, 7G, 7H:
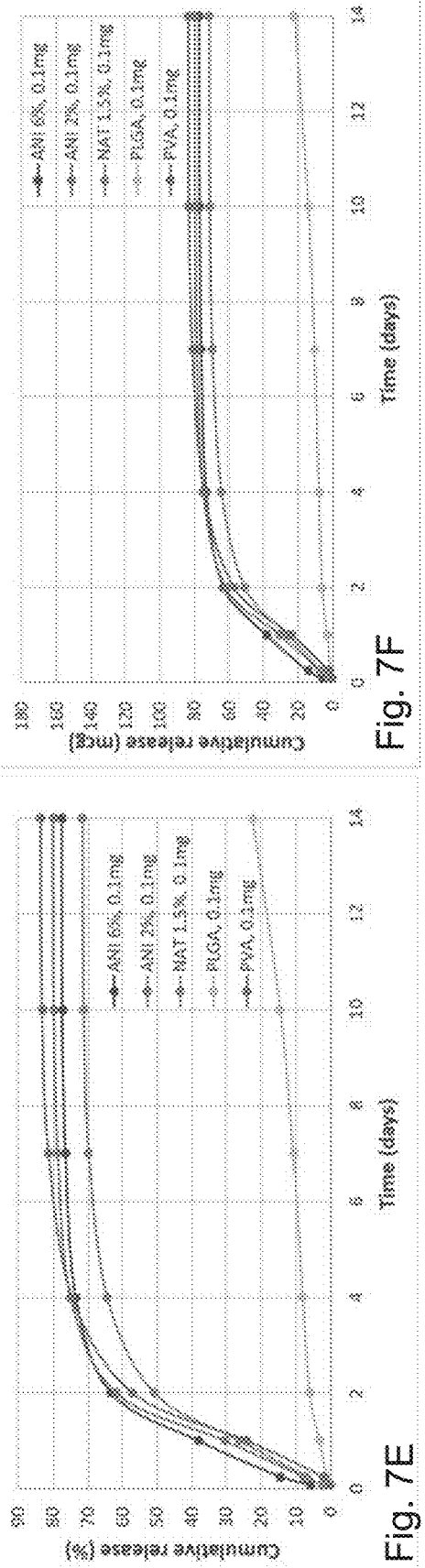
FIG. 7E shows cumulative release of meloxicam in extensive dissolution study up to 14 days with all matrices at a dose of 0.1 mg.
FIG. 7F shows cumulative release of meloxicam in extensive dissolution study up to 14 days with all matrices at a dose of 0.1 mg.
FIG. 7G shows cumulative release of meloxicam in extensive dissolution study up to 14 days with all matrices at a dose of 0.2 mg.
FIG. 7H shows cumulative release of meloxicam in extensive dissolution study up to 14 days with all matrices at a dose of 0.2 mg.
Figures 8E, 8F, 8G, 8H:
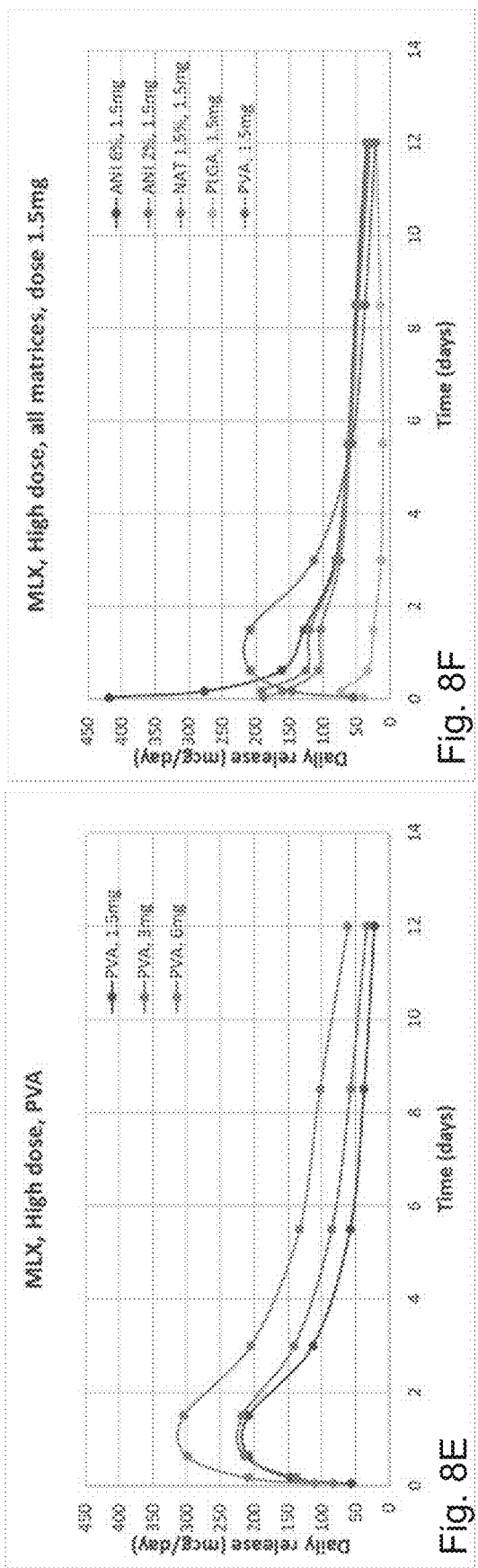
FIG. 8E shows daily release of meloxicam in extensive dissolution study up to 14 days with PVA matrix.
FIG. 8F shows daily release of meloxicam in extensive dissolution study up to 14 days with all matrices at a dose of 1.5 mg.
FIG. 8G shows daily release of meloxicam in extensive dissolution study up to 14 days with all matrices at a dose of 3 mg.
FIG. 8H shows daily release of meloxicam in extensive dissolution study up to 14 days with all matrices at a dose of 6 mg.
Figure 9A:
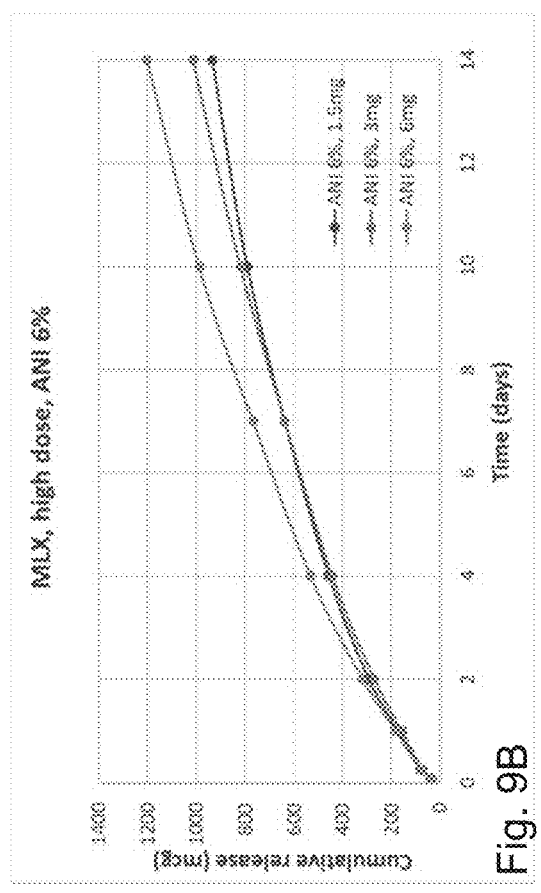
FIG. 9A shows daily release of meloxicam in extensive dissolution study up to 14 days with Anionic 6% NFC matrix.
Figure 9B:
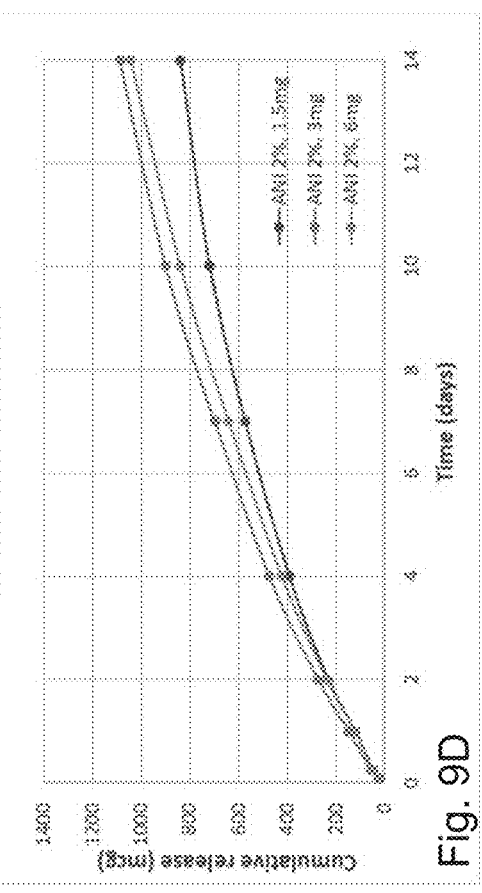
FIG. 9B shows daily release of meloxicam in extensive dissolution study up to 14 days with Anionic 6% NFC matrix.
Figure 9C:
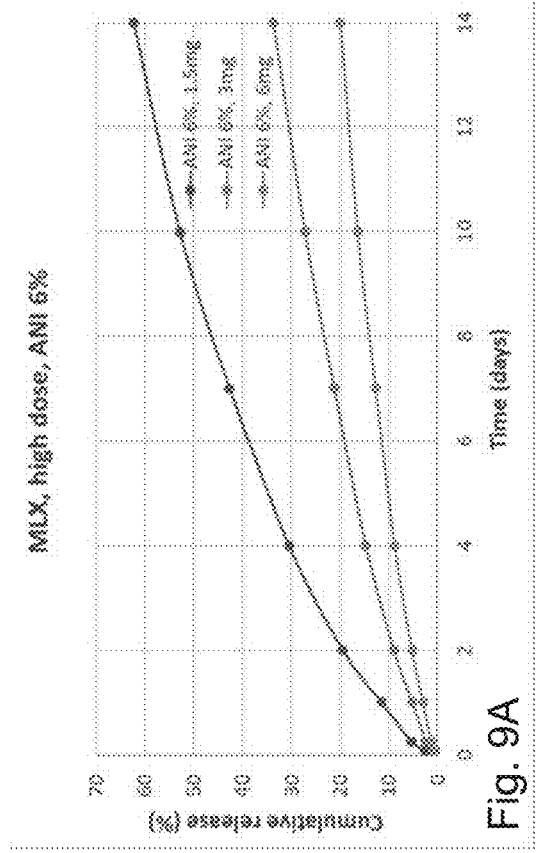
FIG. 9C shows daily release of meloxicam in extensive dissolution study up to 14 days with Anionic 2% NFC matrix.
Figure 9D:
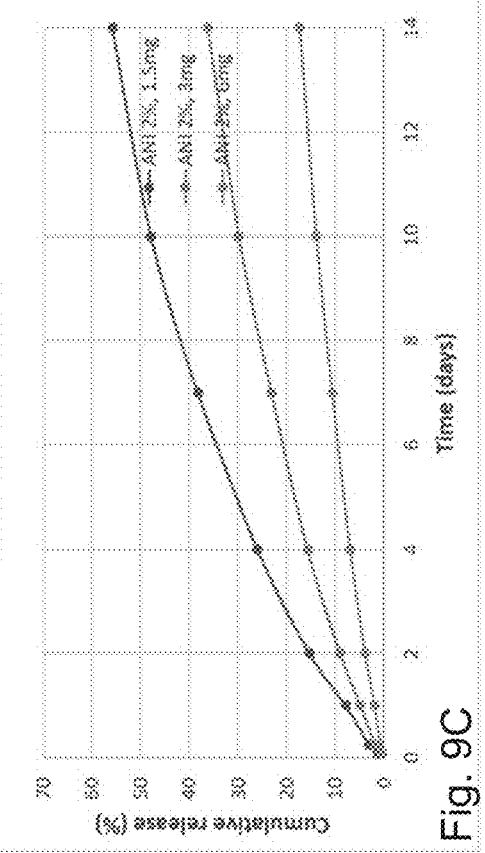
FIG. 9D shows daily release of meloxicam in extensive dissolution study up to 14 days with Anionic 2% NFC matrix.
Figure 10A:
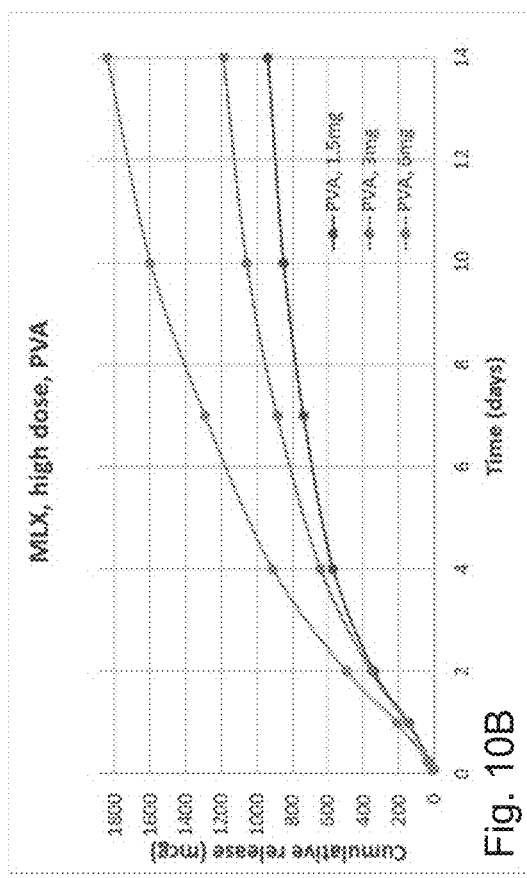
FIG. 10A shows cumulative release of meloxicam in extensive dissolution study up to 14 days with PVA matrix.
Figure 10B:
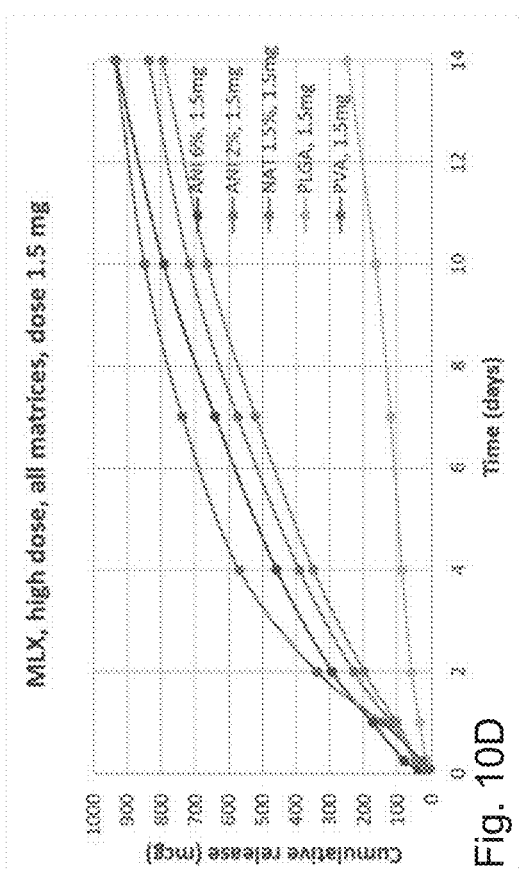
FIG. 10B shows cumulative release of meloxicam in extensive dissolution study up to 14 days with PVA matrix.
Figure 10C:
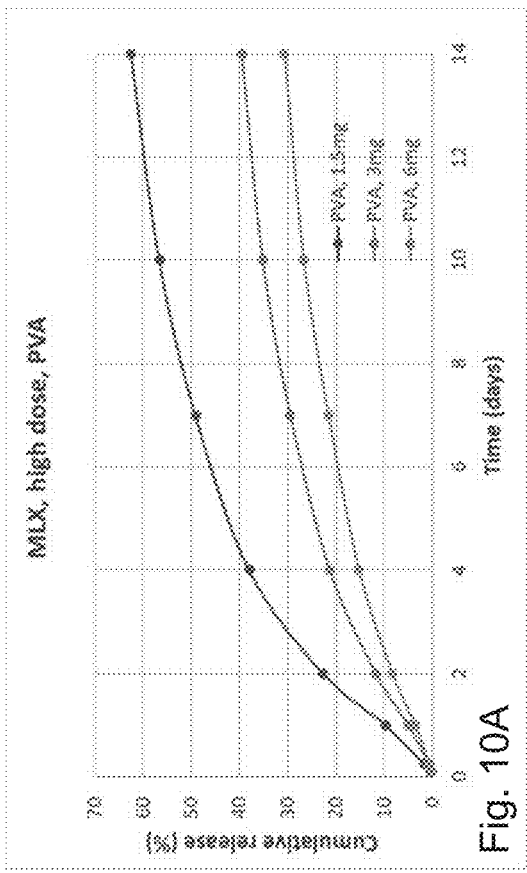
FIG. 10C shows cumulative release of meloxicam in extensive dissolution study up to 14 days with all matrices at a dose of 1.5 mg.
Figure 10D:
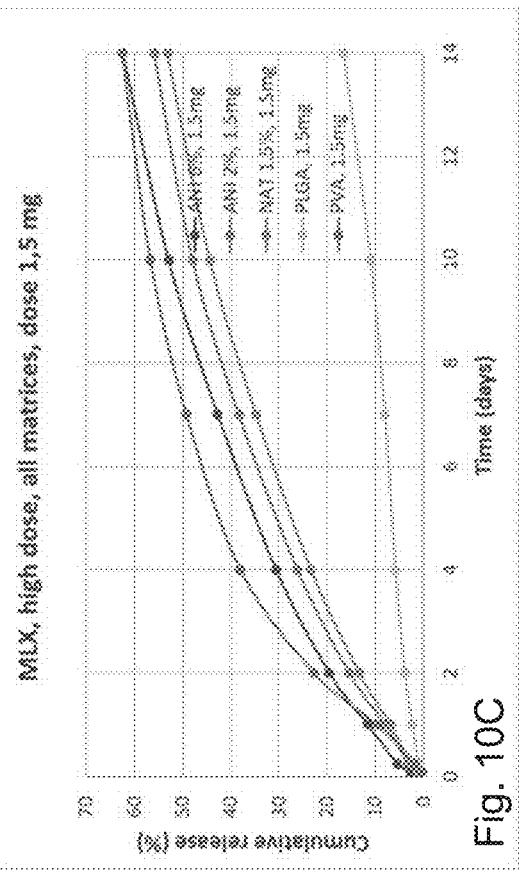
FIG. 10D shows cumulative release of meloxicam in extensive dissolution study up to 14 days with all matrices at a dose of 1.5 mg.
Figure 10E:
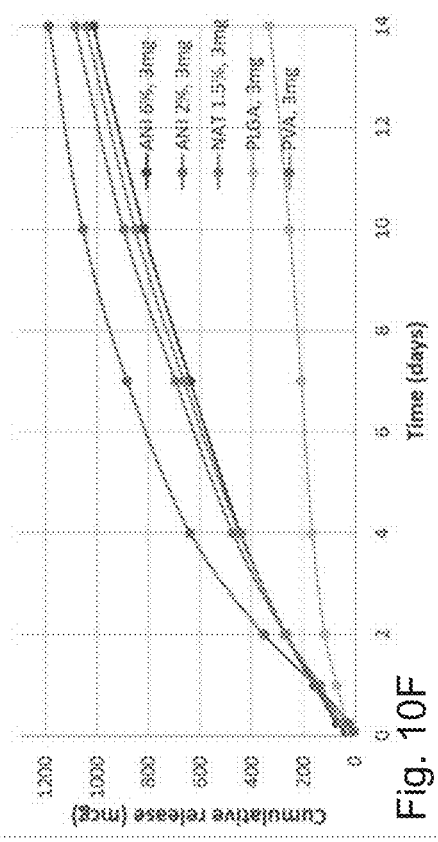
FIG. 10E shows cumulative release of meloxicam in extensive dissolution study up to 14 days with all matrices at a dose of 3 mg.
Figure 10G:
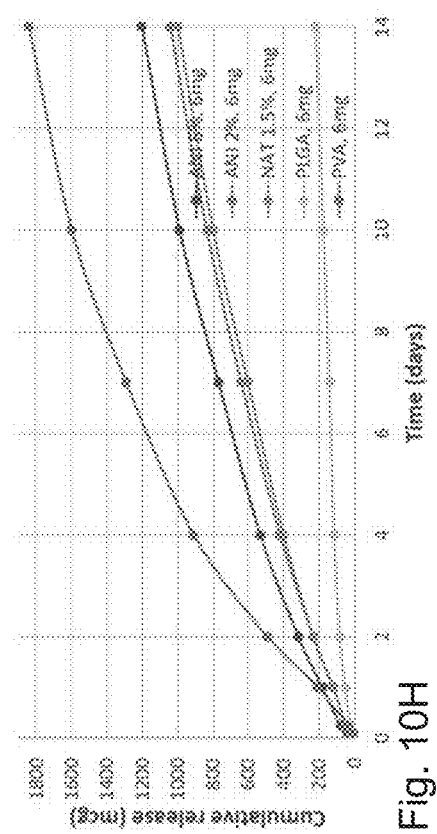
FIG. 10G shows cumulative release of meloxicam in extensive dissolution study up to 14 days with all matrices at a dose of 6 mg.
Figure 10F:
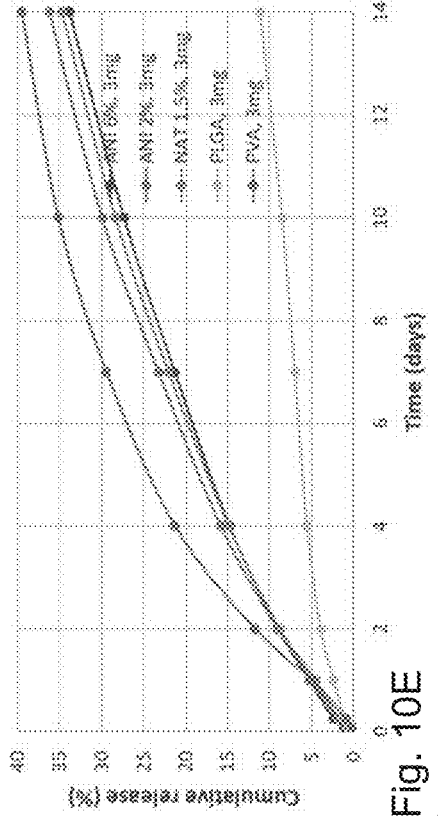
FIG. 10F shows cumulative release of meloxicam in extensive dissolution study up to 14 days with all matrices at a dose of 3 mg.
Figure 10H:
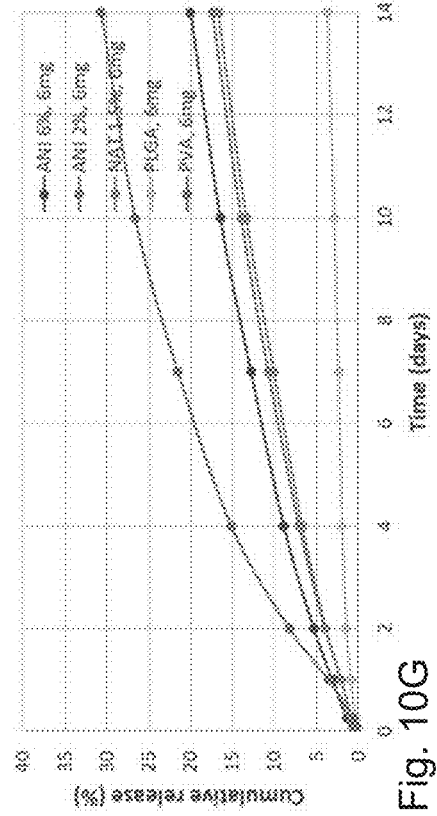
FIG. 10H shows cumulative release of meloxicam in extensive dissolution study up to 14 days with all matrices at a dose of 6 mg.
Figure 11A:
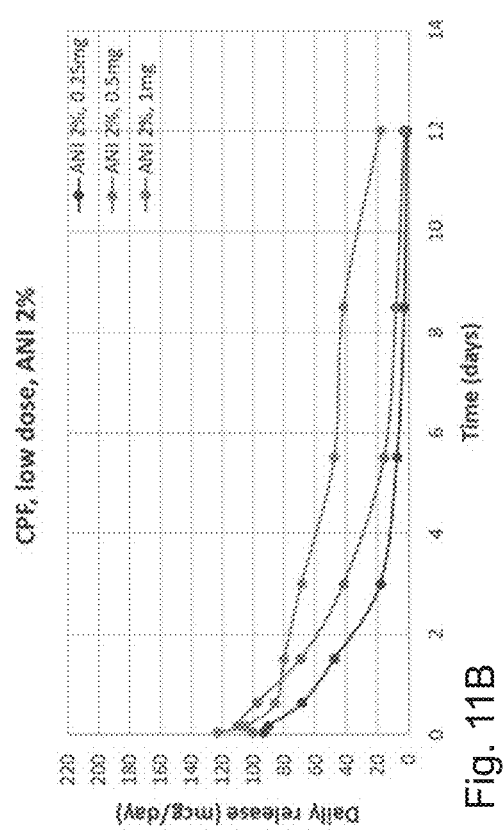
FIG. 11A shows daily release of carprofen in extensive dissolution study up to 14 days with Anionic 6% NFC matrix.
Figure 11B:
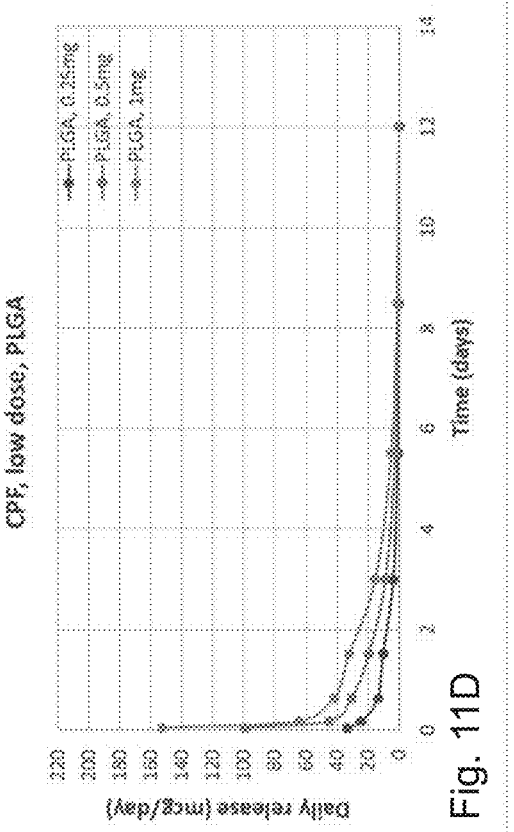
FIG. 11B shows daily release of carprofen in extensive dissolution study up to 14 days with Anionic 2% NFC matrix.
Figure 11C:
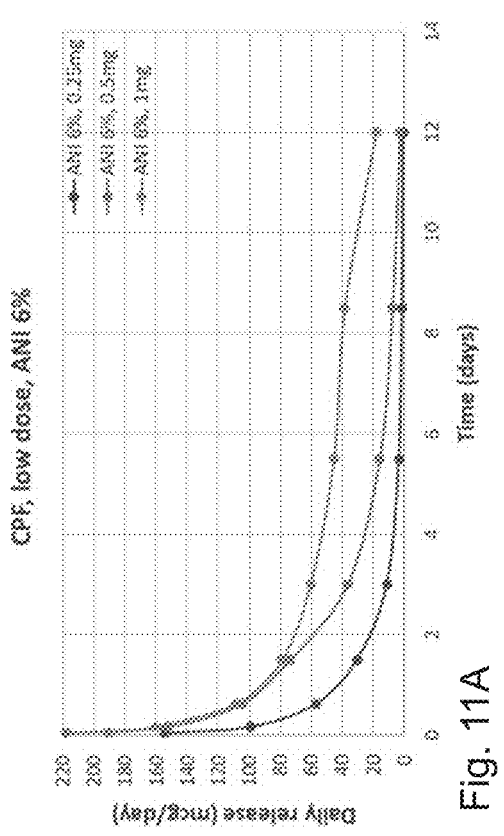
FIG. 11C shows daily release of carprofen in extensive dissolution study up to 14 days with Native 1.5% NFC matrix.
Figure 11D:
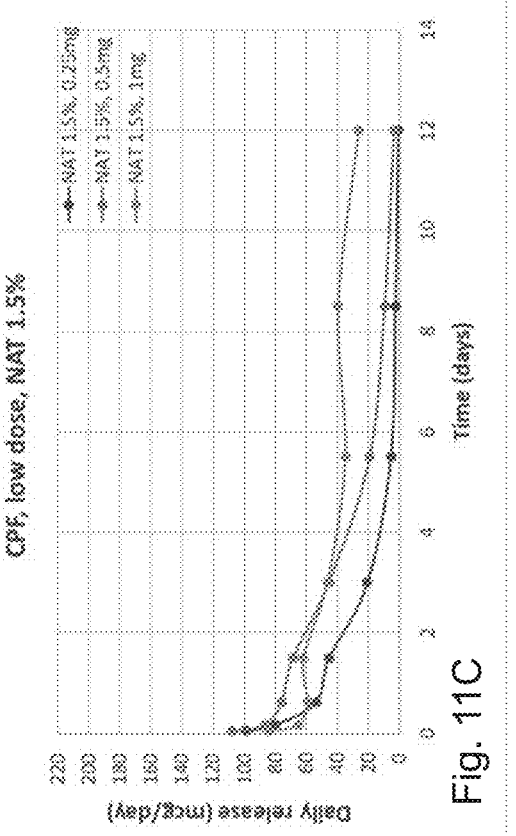
FIG. 11D shows daily release of carprofen in extensive dissolution study up to 14 days with PLGA matrix.
Figure 11E:
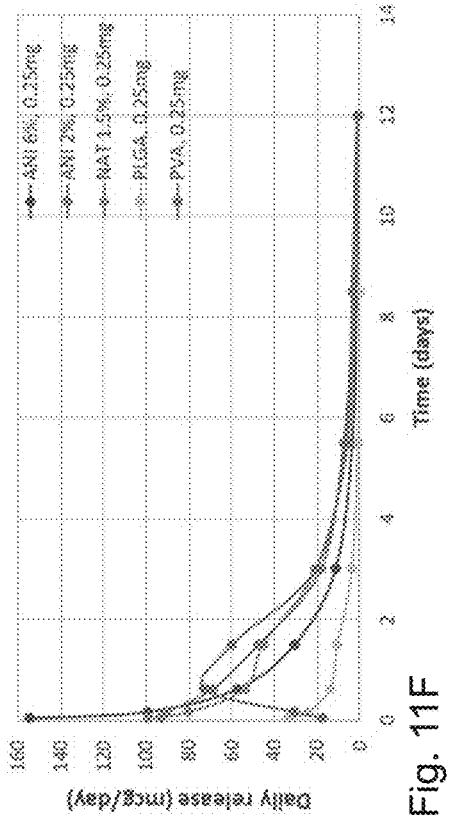
FIG. 11E shows daily release of carprofen in extensive dissolution study up to 14 days with PVA matrix.
Figure 11F:
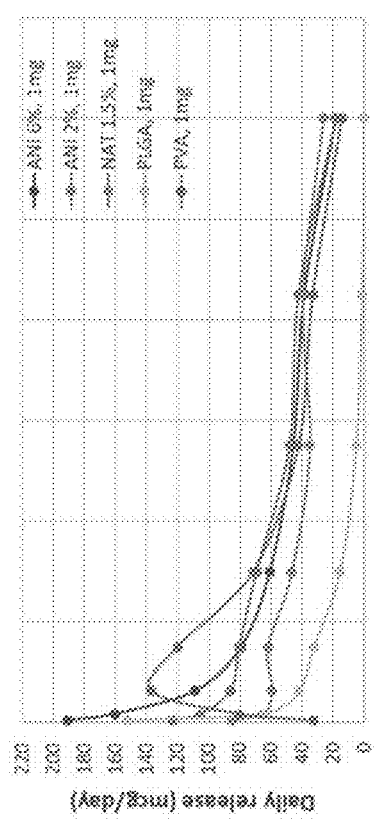
FIG. 11F shows daily release of carprofen in extensive dissolution study up to 14 days with all matrices at a dose of 0.25 mg.
Figure 11G:
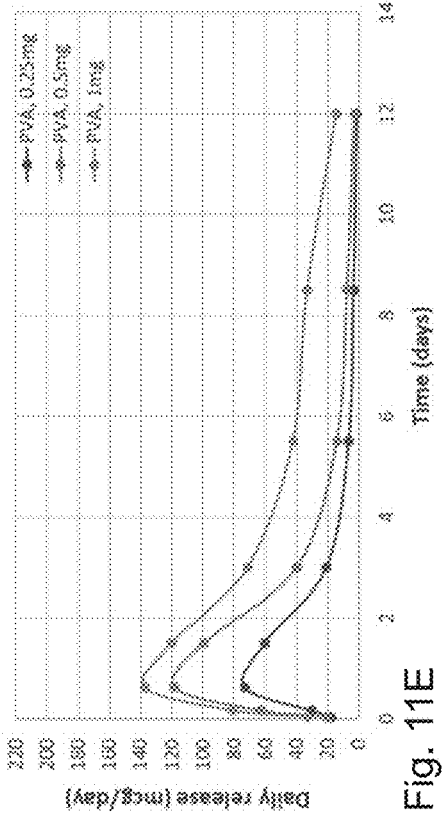
FIG. 11G shows daily release of carprofen in extensive dissolution study up to 14 days with all matrices at a dose of 0.5 mg.
Figure 11H:
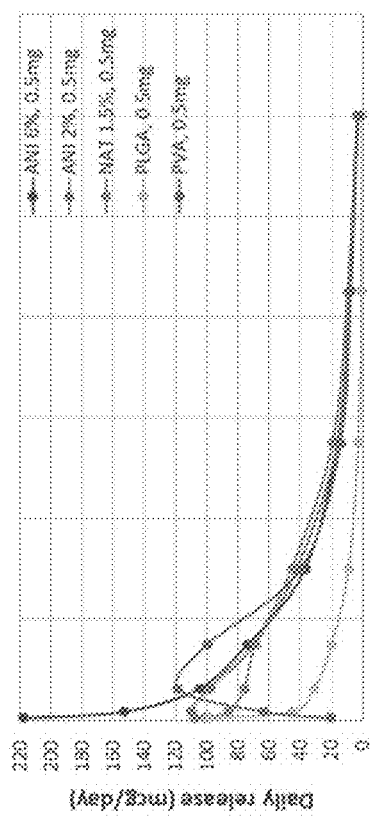
FIG. 11H shows daily release of carprofen in extensive dissolution study up to 14 days with all matrices at a dose of 1 mg.
Figure 12B:
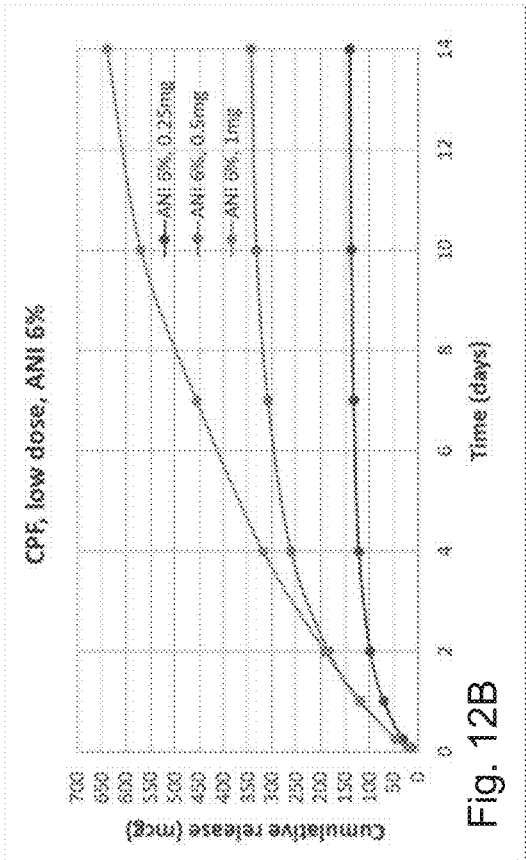
FIG. 12B shows daily release of carprofen in extensive dissolution study up to 14 days with Anionic 6% NFC matrix.
Figure 12D:
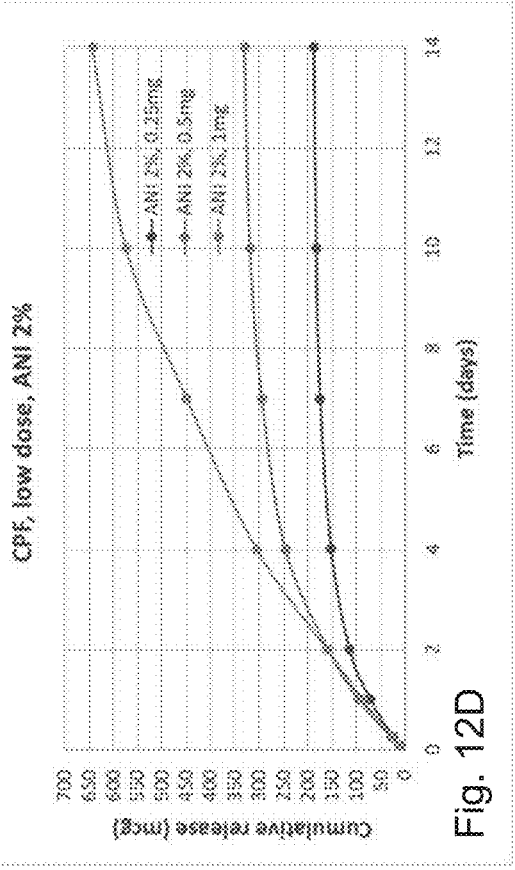
FIG. 12D shows daily release of carprofen in extensive dissolution study up to 14 days with Anionic 2% NFC matrix.
Figure 12A:
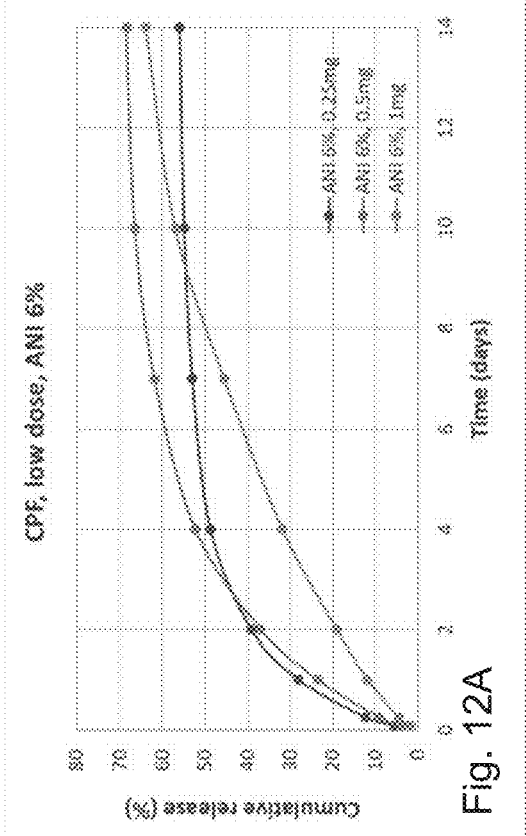
FIG. 12A shows daily release of carprofen in extensive dissolution study up to 14 days with Anionic 6% NFC matrix.
Figure 12C:
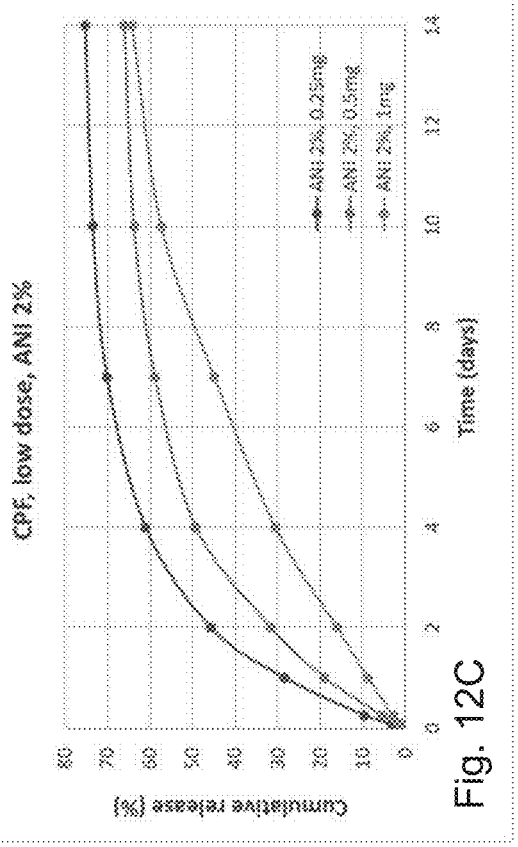
FIG. 12C shows daily release of carprofen in extensive dissolution study up to 14 days with Anionic 2% NFC matrix.
Figure 13A:
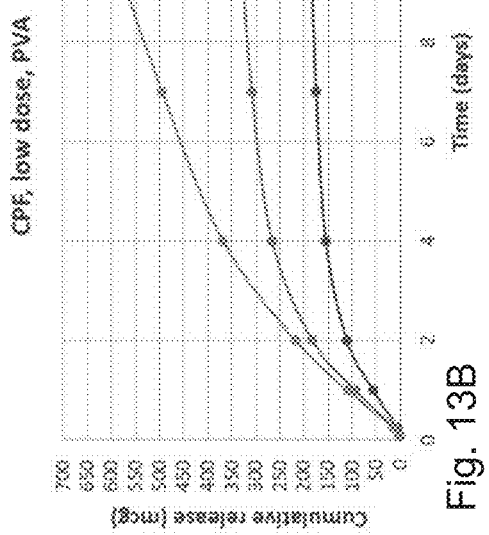
FIG. 13A shows cumulative release of carprofen in extensive dissolution study up to 14 days with PVA matrix.
Figure 13B:
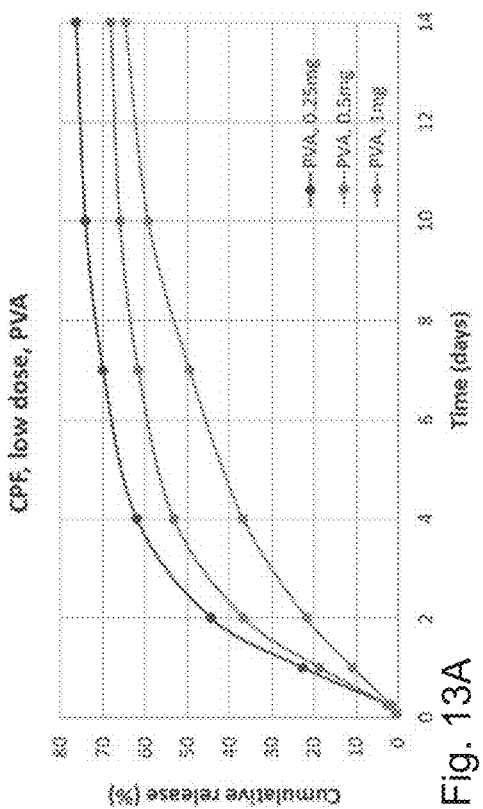
FIG. 13B shows cumulative release of carprofen in extensive dissolution study up to 14 days with PVA matrix.
Figure 13C:
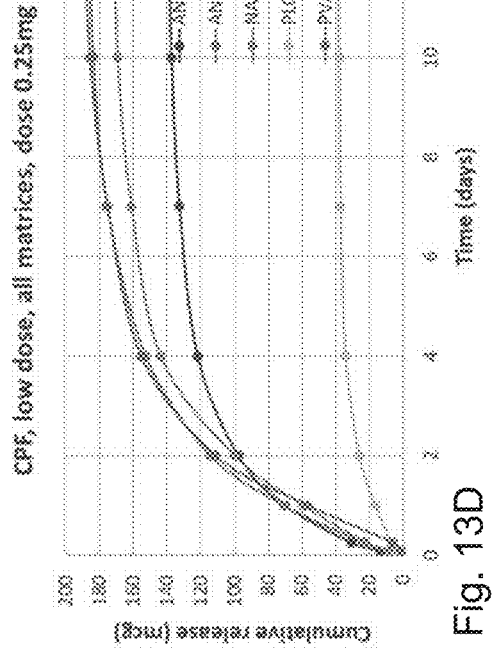
FIG. 13C shows cumulative release of carprofen in extensive dissolution study up to 14 days with all matrices at a dose of 0.25 mg.
Figure 13D:
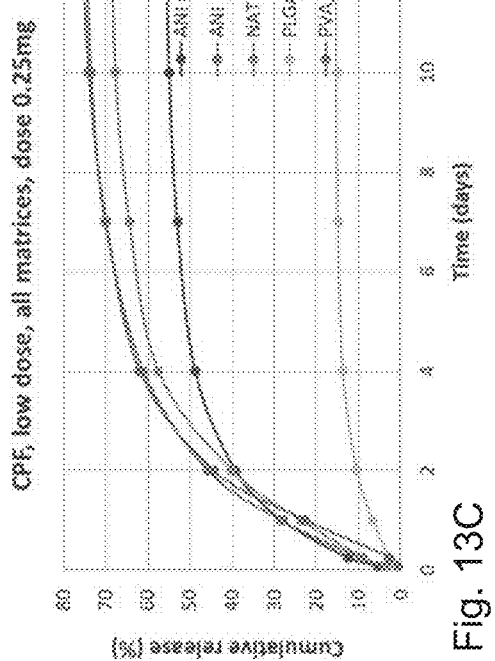
FIG. 13D shows cumulative release of carprofen in extensive dissolution study up to 14 days with all matrices at a dose of 0.25 mg.
Figure 13E:
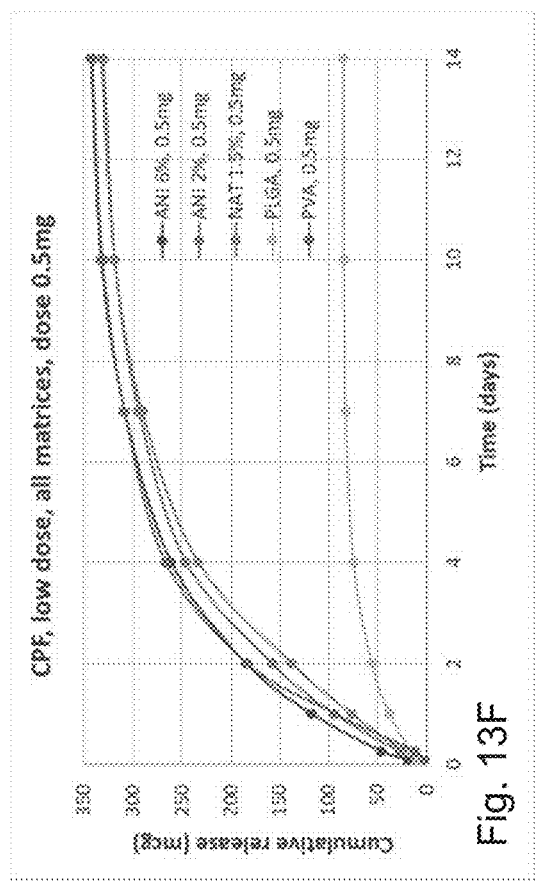
FIG. 13E shows cumulative release of carprofen in extensive dissolution study up to 14 days with all matrices at a dose of 0.5 mg.
Figure 13F:
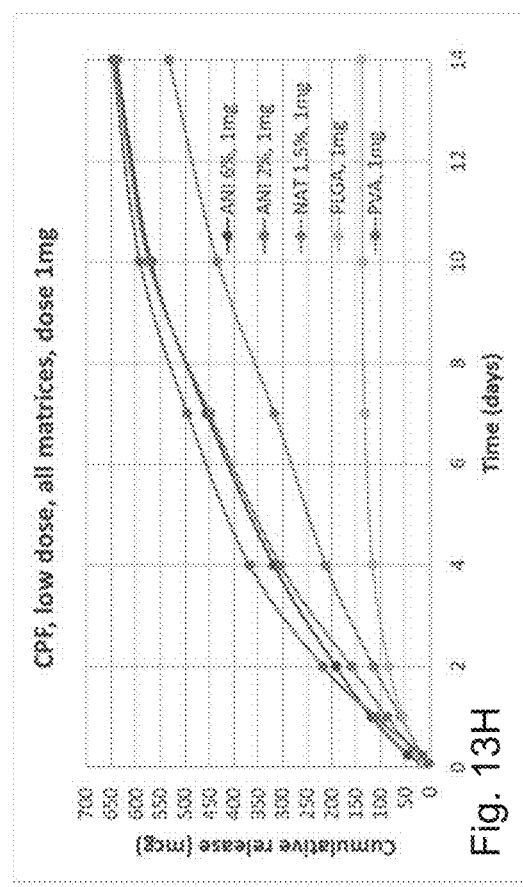
FIG. 13F shows cumulative release of carprofen in extensive dissolution study up to 14 days with all matrices at a dose of 0.5 mg.
Figure 13G:
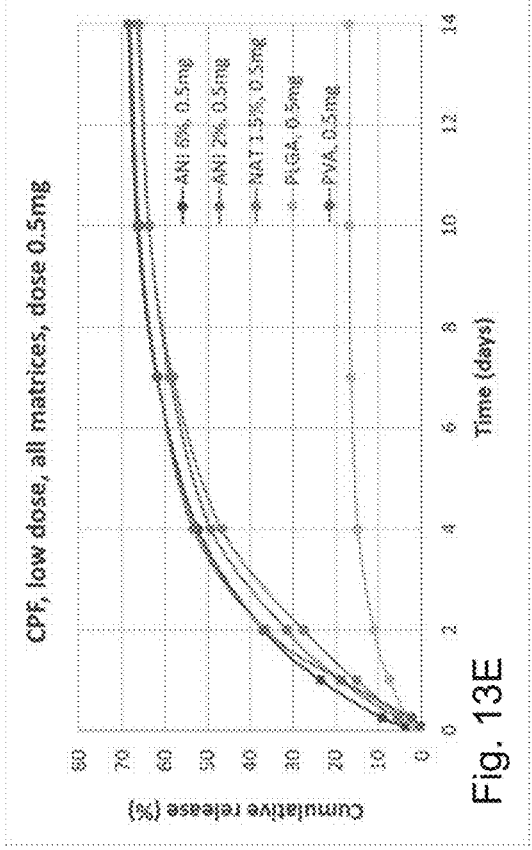
FIG. 13G shows cumulative release of carprofen in extensive dissolution study up to 14 days with all matrices at a dose of 1 mg.
Figure 13H:
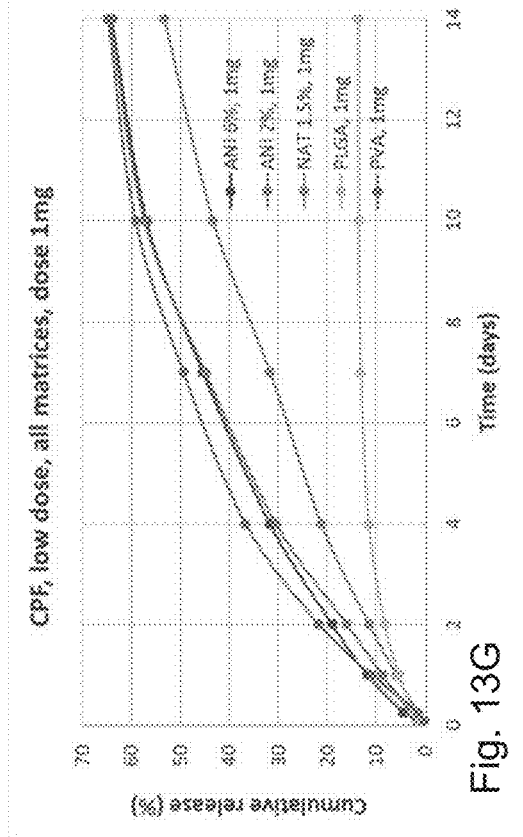
FIG. 13H shows cumulative release of carprofen in extensive dissolution study up to 14 days with all matrices at a dose of 1 mg.
Figure 14B:
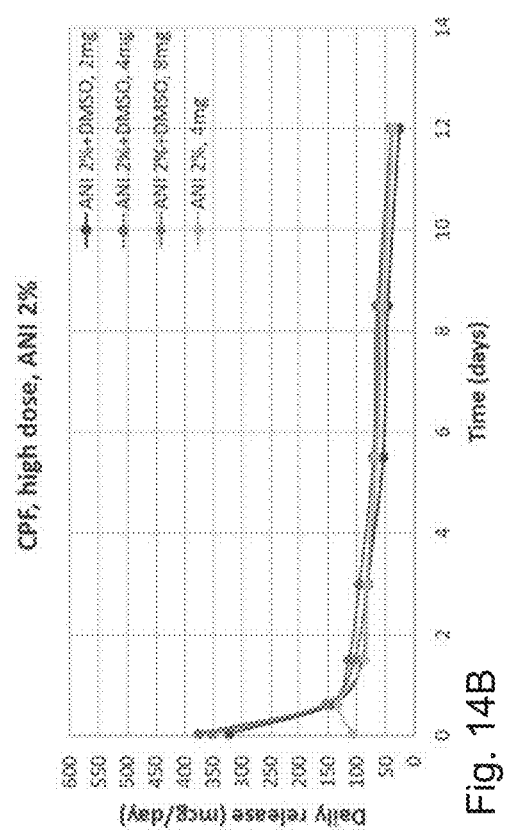
FIG. 14B shows daily release of carprofen in extensive dissolution study up to 14 days with Anionic 2% NFC matrix.
Figure 14D:
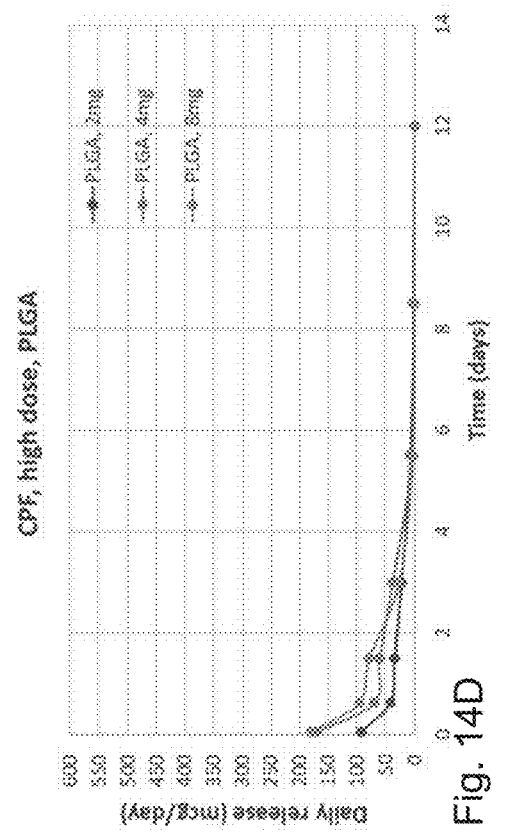
FIG. 14D shows daily release of carprofen in extensive dissolution study up to 14 days with PLGA matrix.
Figure 14A:
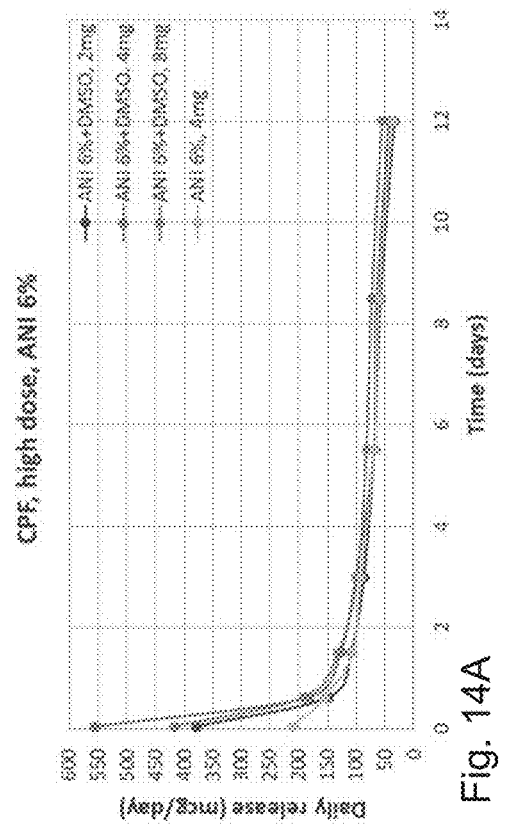
FIG. 14A shows daily release of carprofen in extensive dissolution study up to 14 days with Anionic 6% NFC matrix.
Figure 14C:
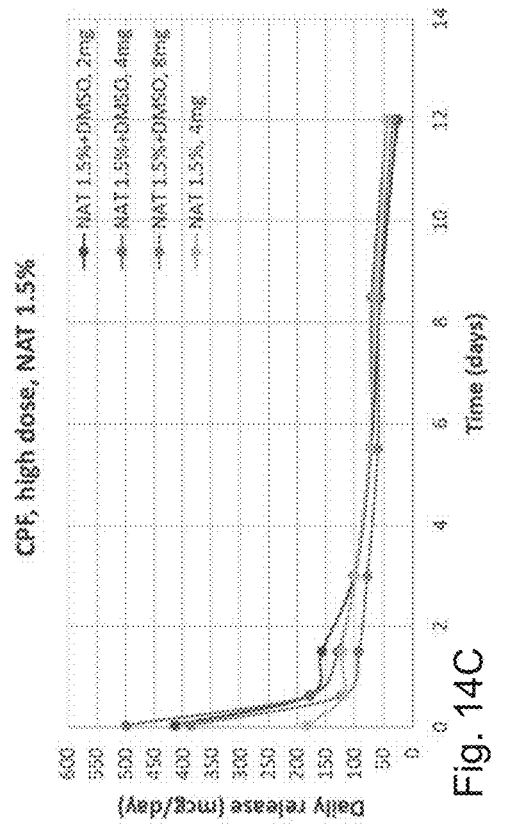
FIG. 14C shows daily release of carprofen in extensive dissolution study up to 14 days with Native 1.5% NFC matrix.
Figure 14E:
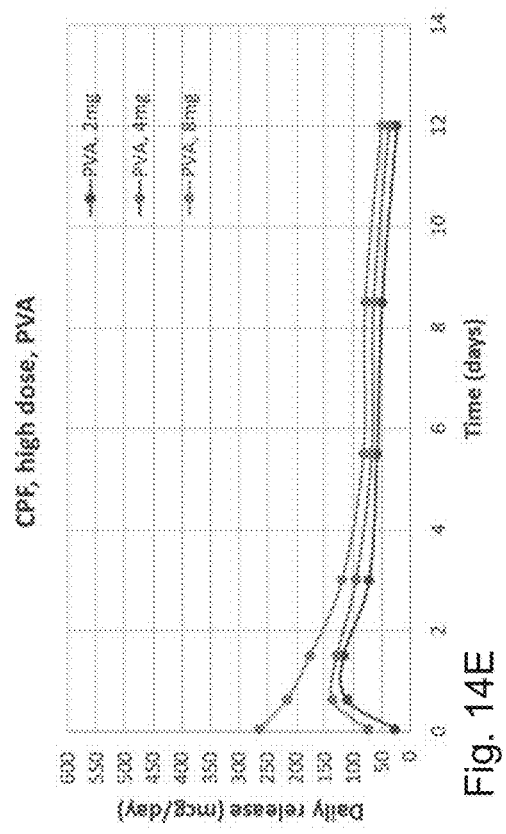
FIG. 14E shows daily release of carprofen in extensive dissolution study up to 14 days with PVA matrix.
Figure 14F:
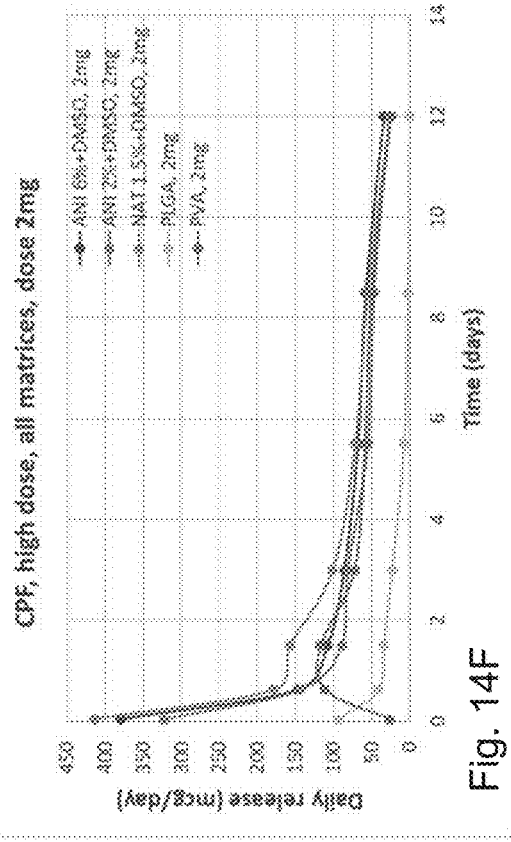
FIG. 14F shows daily release of carprofen in extensive dissolution study up to 14 days with all matrices at a dose of 2 mg.
Figure 14G:
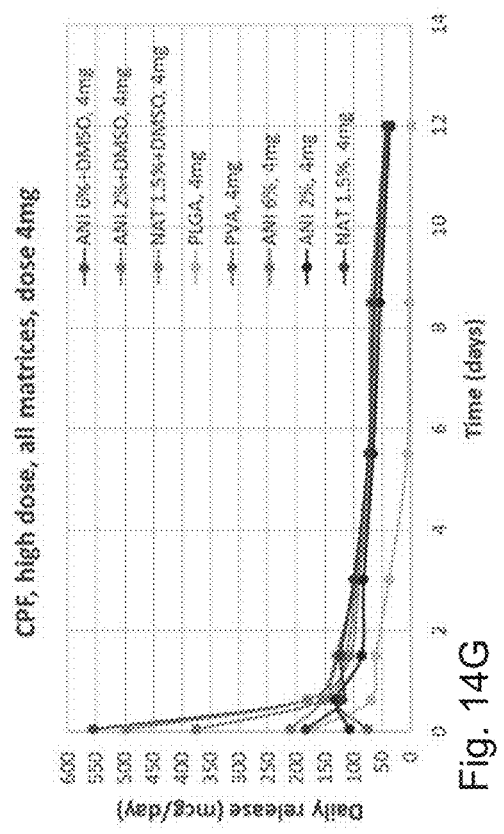
FIG. 14G shows daily release of carprofen in extensive dissolution study up to 14 days with all matrices at a dose of 4 mg.
Figure 14H:
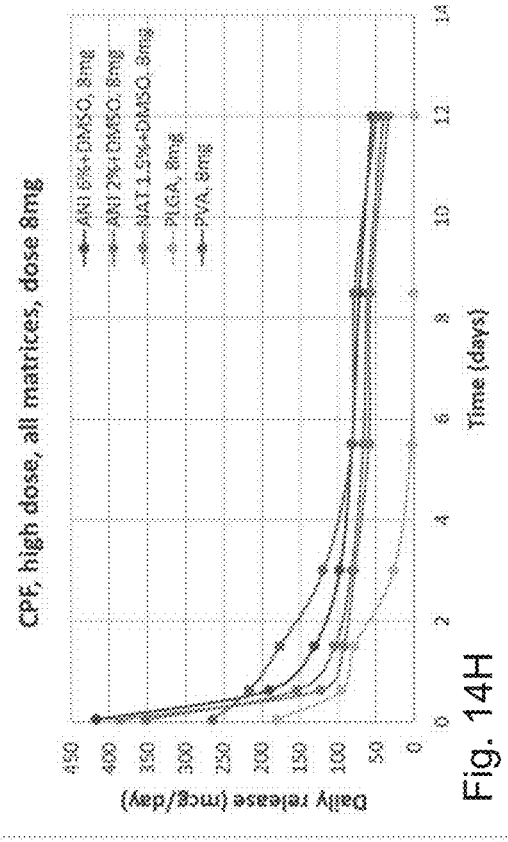
FIG. 14H shows daily release of carprofen in extensive dissolution study up to 14 days with all matrices at a dose of 8 mg.
Figure 15A:
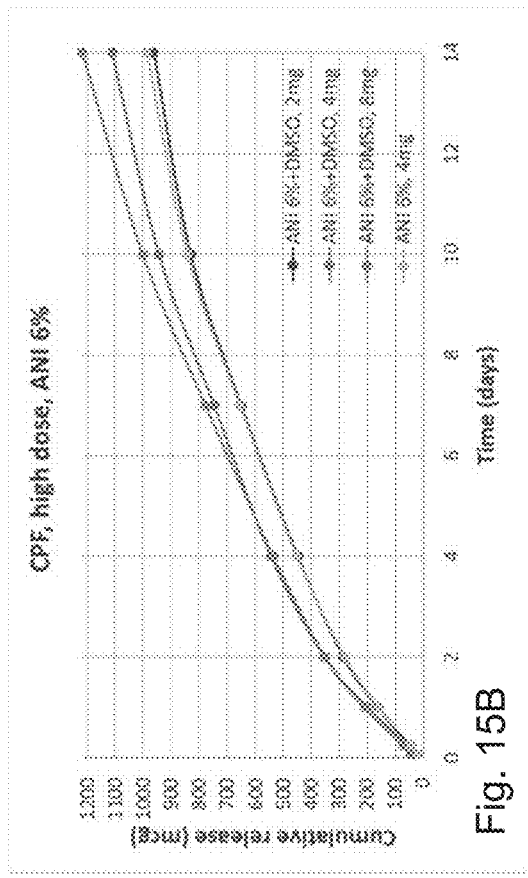
FIG. 15A shows daily release of carprofen in extensive dissolution study up to 14 days with Anionic 6% NFC matrix.
Figure 15B:
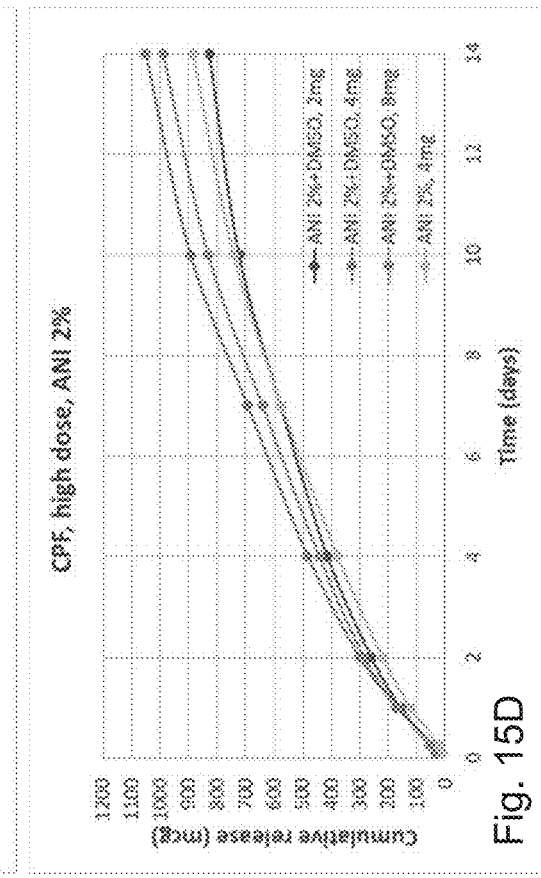
FIG. 15B shows daily release of carprofen in extensive dissolution study up to 14 days with Anionic 6% NFC matrix.
Figure 15C:
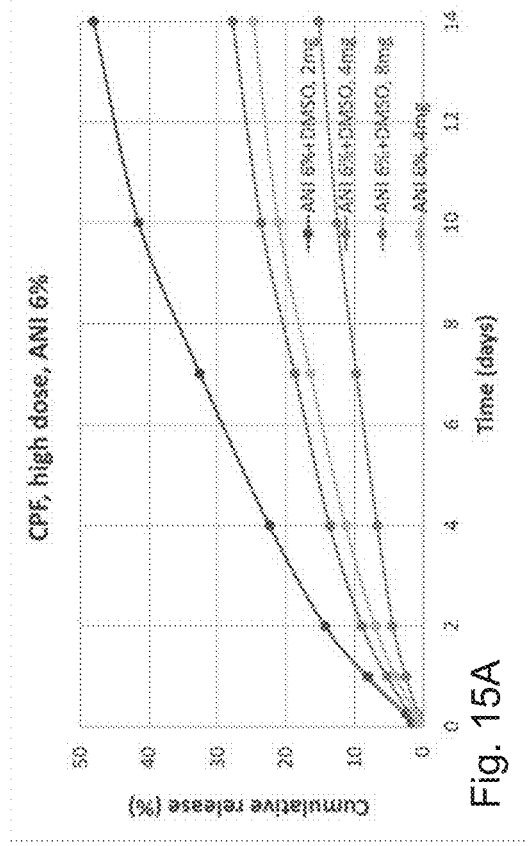
FIG. 15C shows daily release of carprofen in extensive dissolution study up to 14 days with Anionic 2% NFC matrix.
Figure 15D:
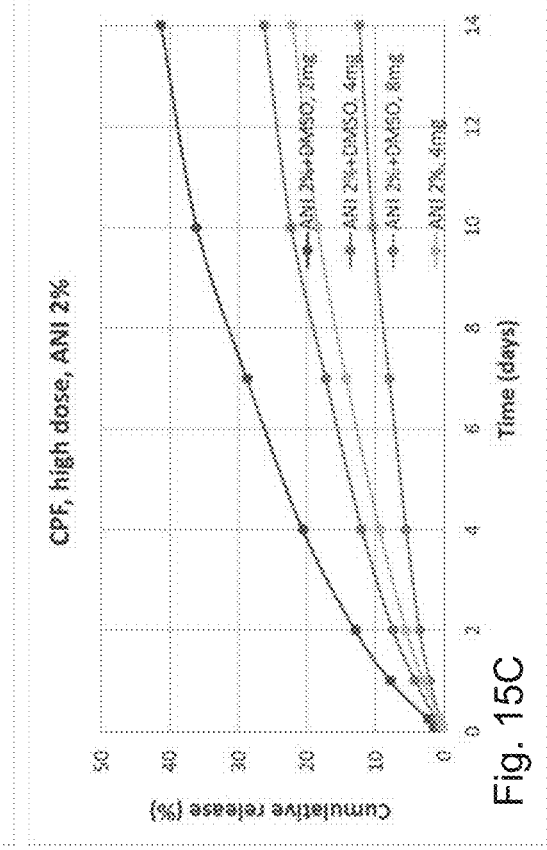
FIG. 15D shows daily release of carprofen in extensive dissolution study up to 14 days with Anionic 2% NFC matrix.
Figure 15E:
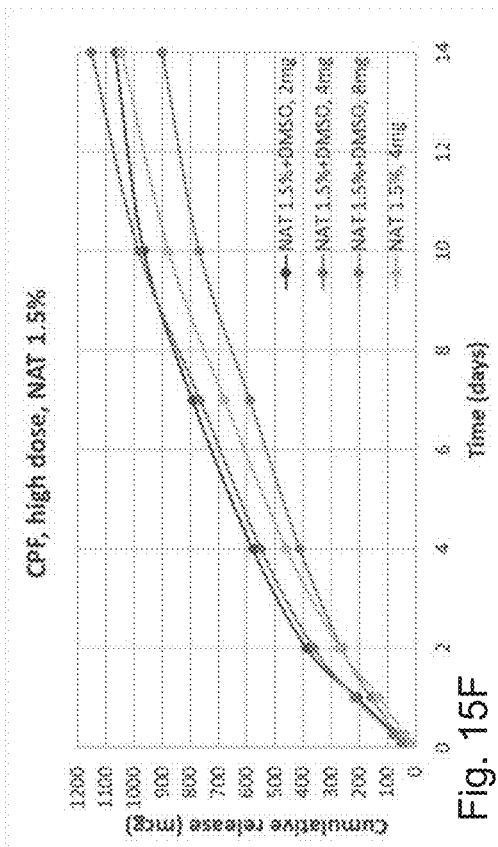
FIG. 15E shows daily release of carprofen in extensive dissolution study up to 14 days with Native 1.5% NFC matrix.
Figure 15F:
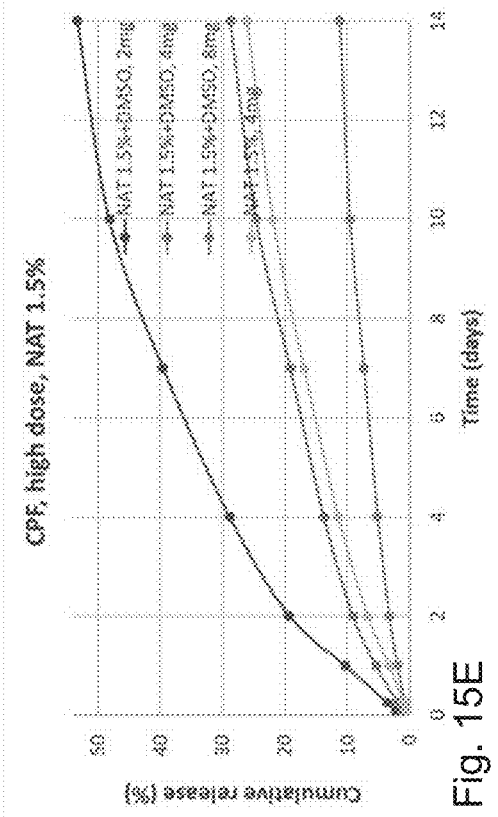
FIG. 15F shows daily release of carprofen in extensive dissolution study up to 14 days with Native 1.5% NFC matrix.
Figure 15G:
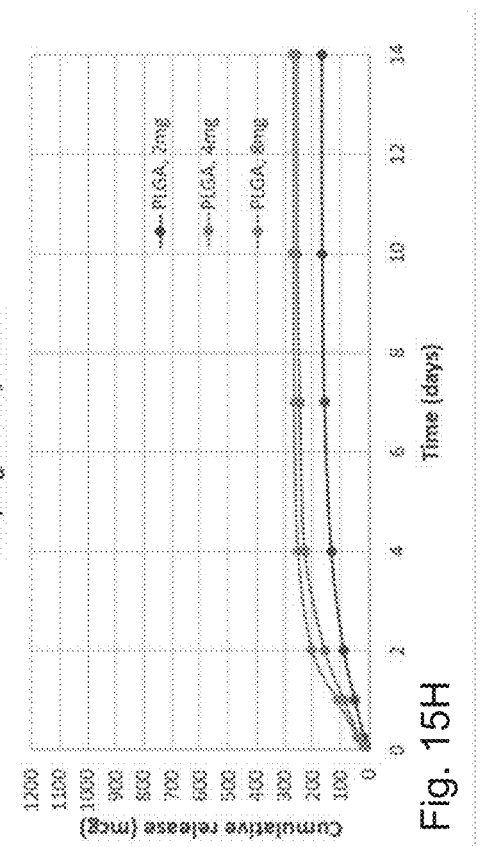
FIG. 15G shows daily release of carprofen in extensive dissolution study up to 14 days with PLGA matrix.
Figure 15H:
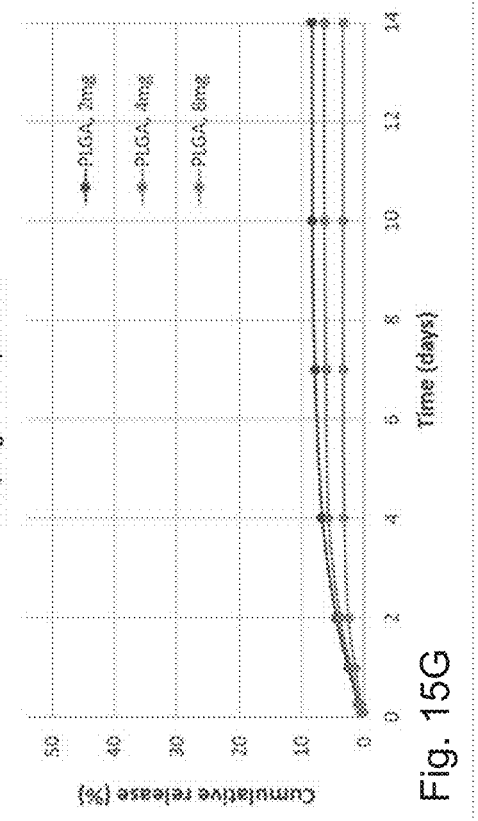
FIG. 15H shows daily release of carprofen in extensive dissolution study up to 14 days with PLGA matrix.
Figure 16A:
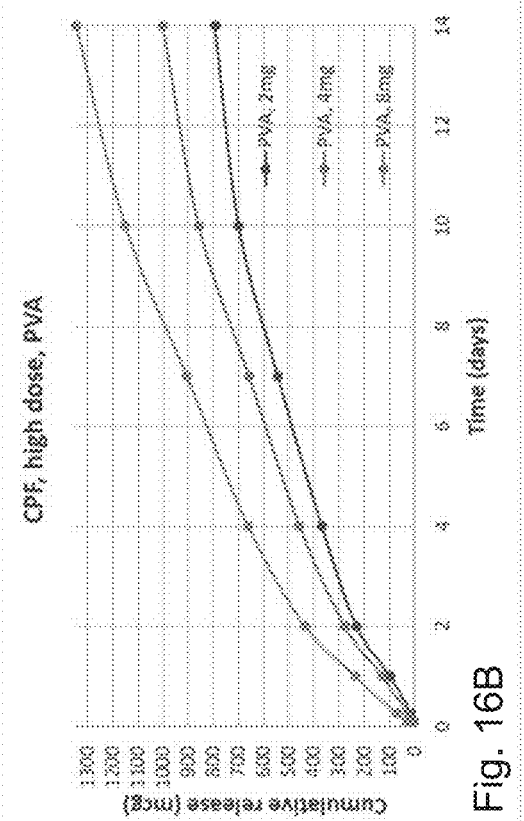
FIG. 16A shows cumulative release of carprofen in extensive dissolution study up to 14 days with PVA matrix.
Figure 16B:
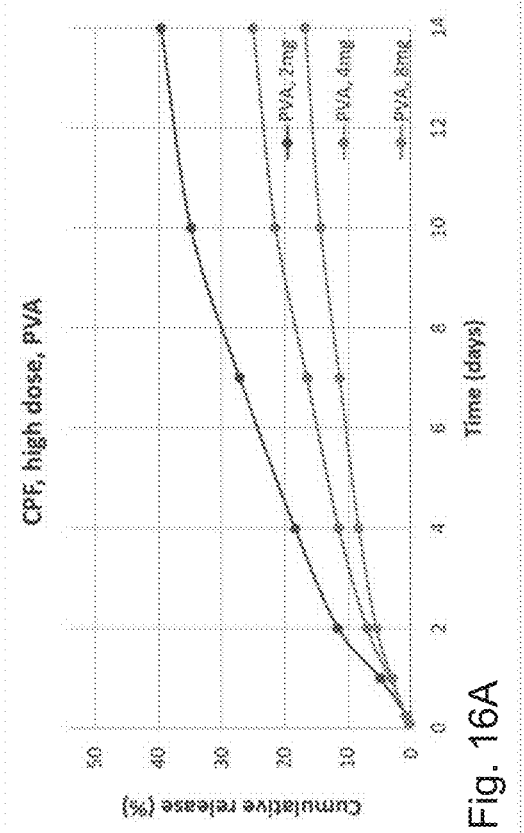
FIG. 16B shows cumulative release of carprofen in extensive dissolution study up to 14 days with PVA matrix.
Figure 16C:
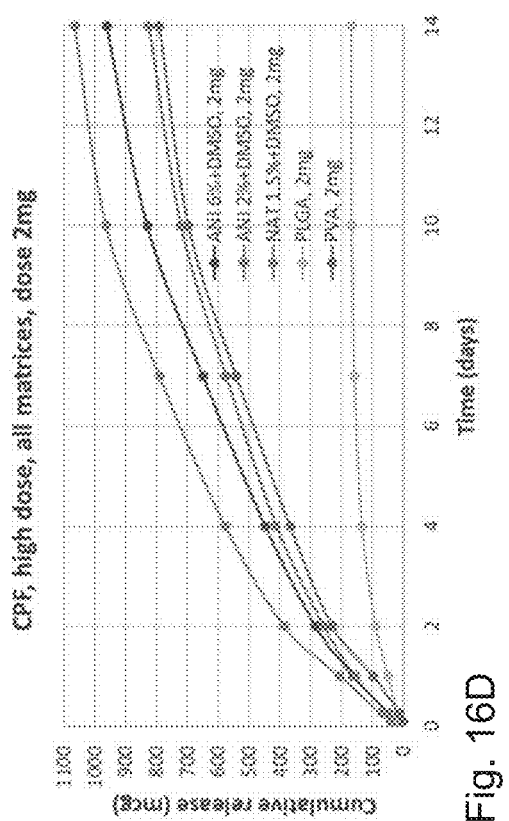
FIG. 16C shows cumulative release of carprofen in extensive dissolution study up to 14 days with all matrices at a dose of 2 mg.
Figure 16D:
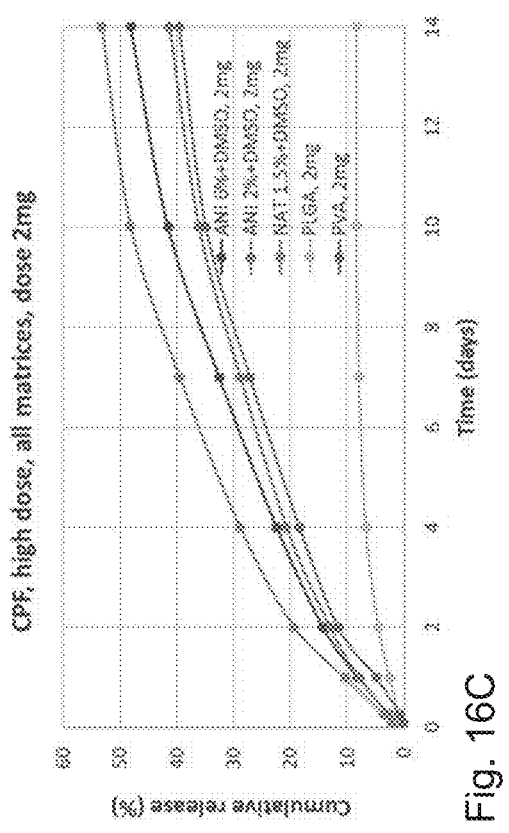
FIG. 16D shows cumulative release of carprofen in extensive dissolution study up to 14 days with all matrices at a dose of 2 mg.
Figure 16E:
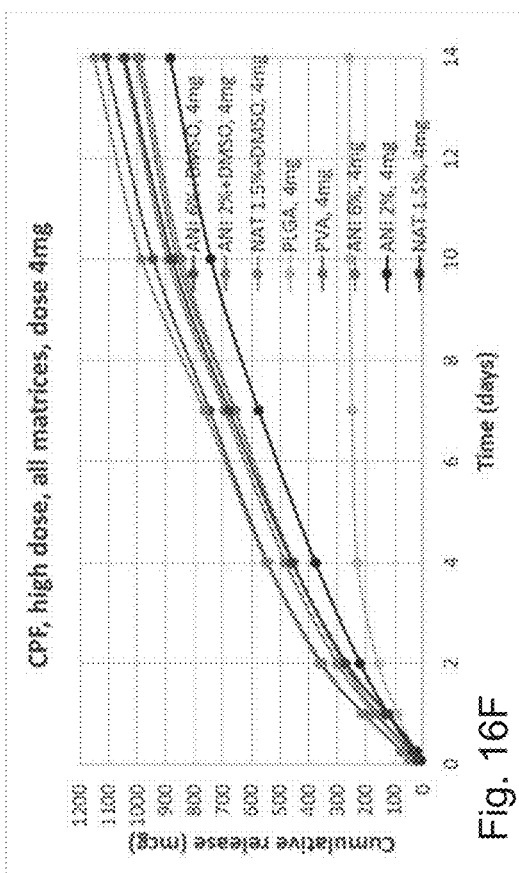
FIG. 16E shows cumulative release of carprofen in extensive dissolution study up to 14 days with all matrices at a dose of 4 mg.
Figure 16G:
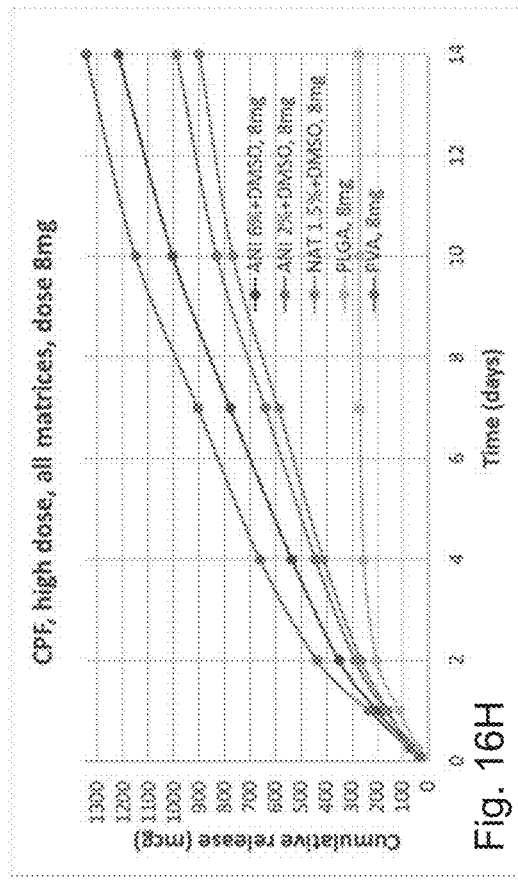
FIG. 16G shows cumulative release of carprofen in extensive dissolution study up to 14 days with all matrices at a dose of 8 mg.
Figure 16F:
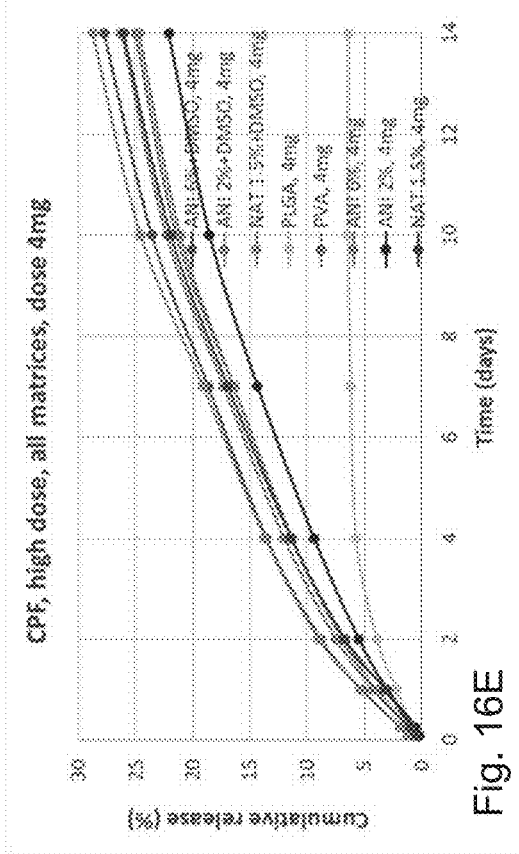
FIG. 16F shows cumulative release of carprofen in extensive dissolution study up to 14 days with all matrices at a dose of 4 mg.
Figure 16H:
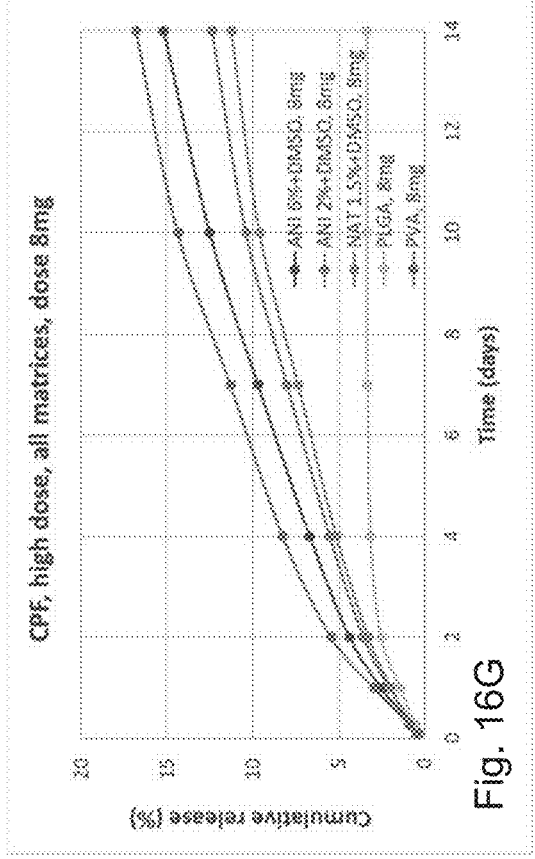
FIG. 16H shows cumulative release of carprofen in extensive dissolution study up to 14 days with all matrices at a dose of 8 mg.
Figure 17A:
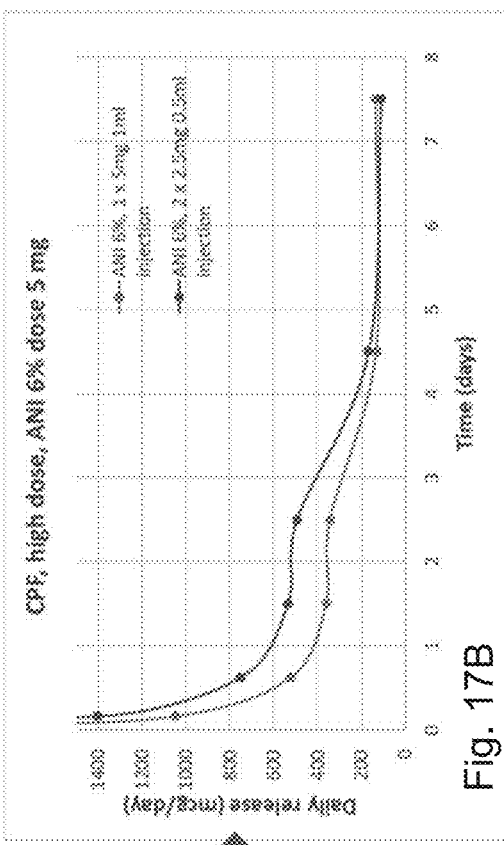
FIG. 17A shows daily release of carprofen in in extensive dissolution study up to 9 days with Anionic 6% NFC matrix and 5 mg CPF dose.
Figure 17B:
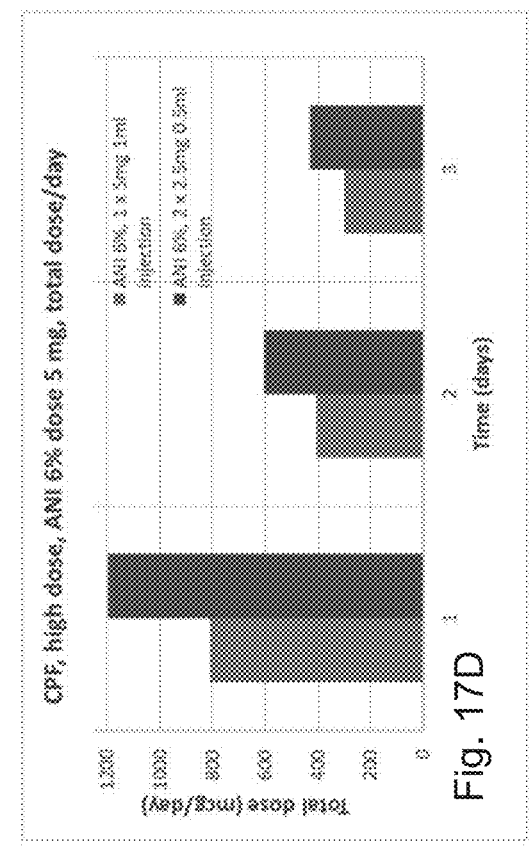
FIG. 17B shows daily release of carprofen in in extensive dissolution study up to 9 days with Anionic 6% NFC matrix and 5 mg CPF dose.
Figure 17C:
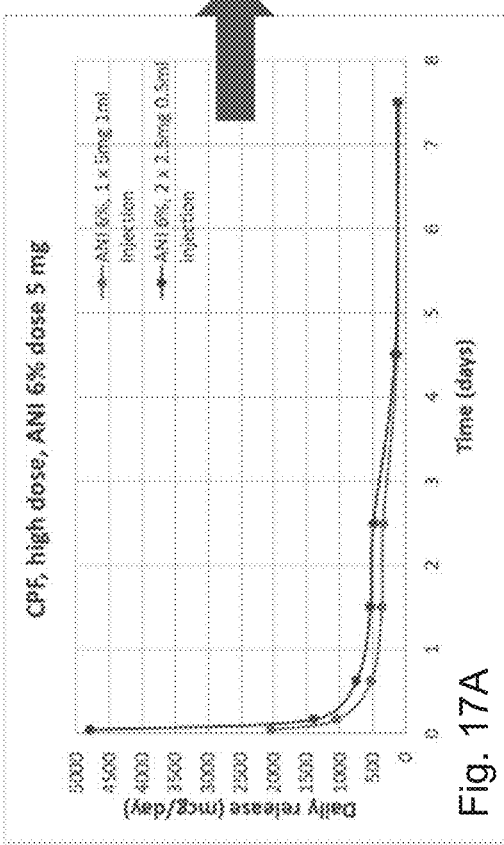
FIG. 17C shows cumulative release of carprofen in in extensive dissolution study up to 9 days with Anionic 6% NFC matrix and 5 mg CPF dose.
Figure 17D:
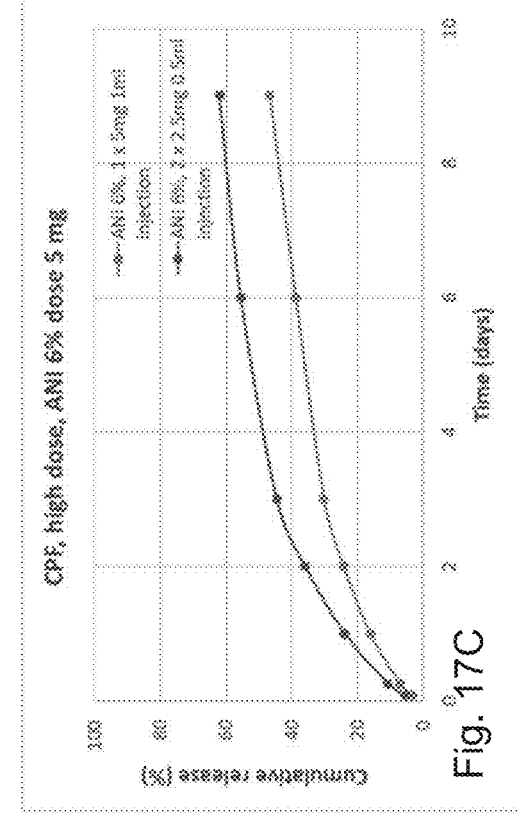
FIG. 17D shows a histogram of the total dose accumulated per day.
Figure 18A:
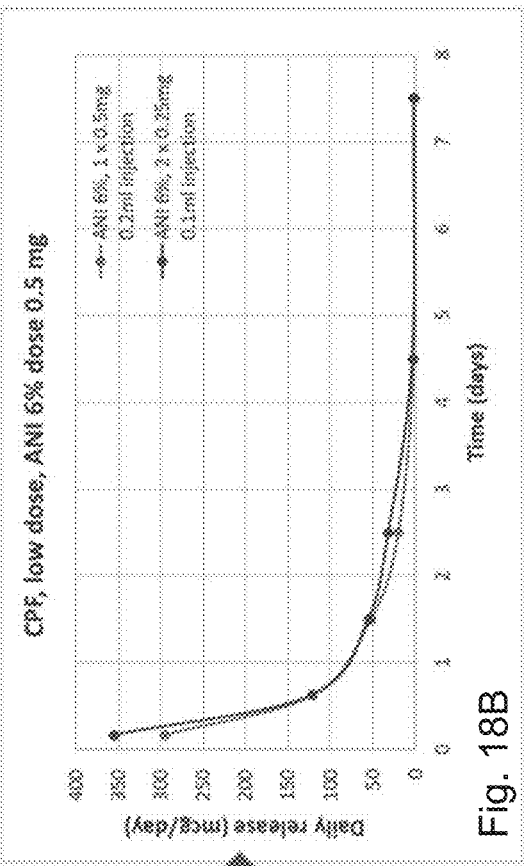
FIG. 18A shows daily release of carprofen in in extensive dissolution study up to 9 days with Anionic 6% NFC matrix and 0.5 mg CPF dose.
Figure 18B:
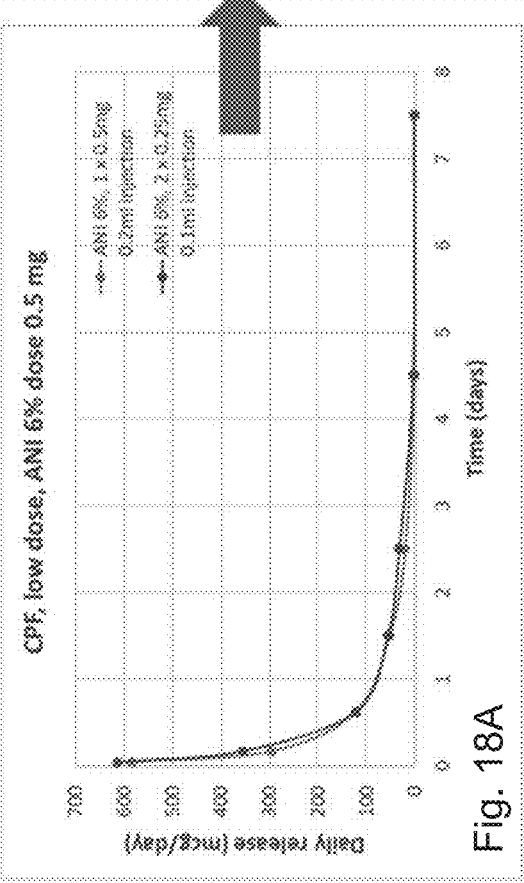
FIG. 18B shows daily release of carprofen in in extensive dissolution study up to 9 days with Anionic 6% NFC matrix and 0.5 mg CPF dose.
Figure 18C:
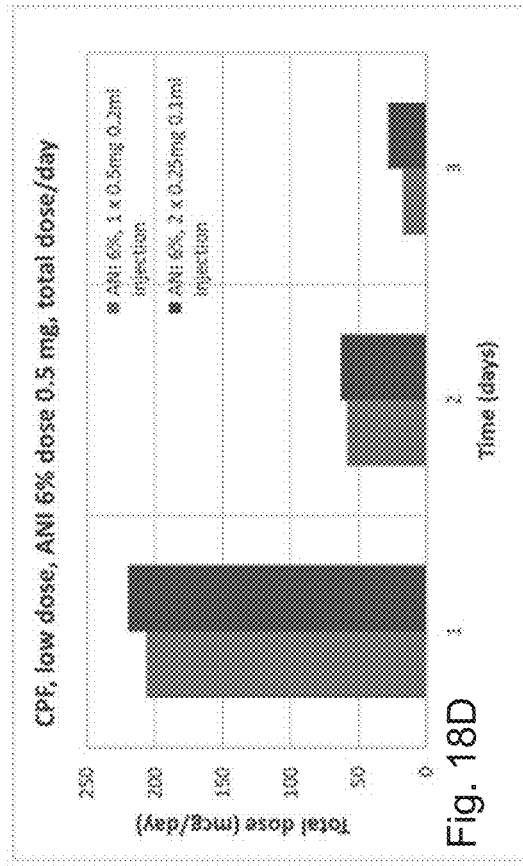
FIG. 18C shows cumulative release of carprofen in in extensive dissolution study up to 9 days with Anionic 6% NFC matrix and 0.5 mg CPF dose.
Figure 18D:
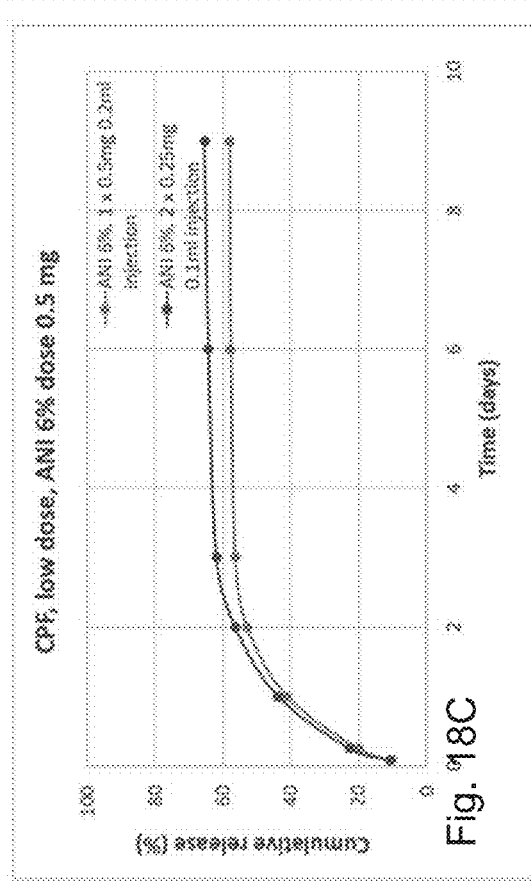
FIG. 18D shows a histogram of the total dose accumulated per day.
Figure 19A:
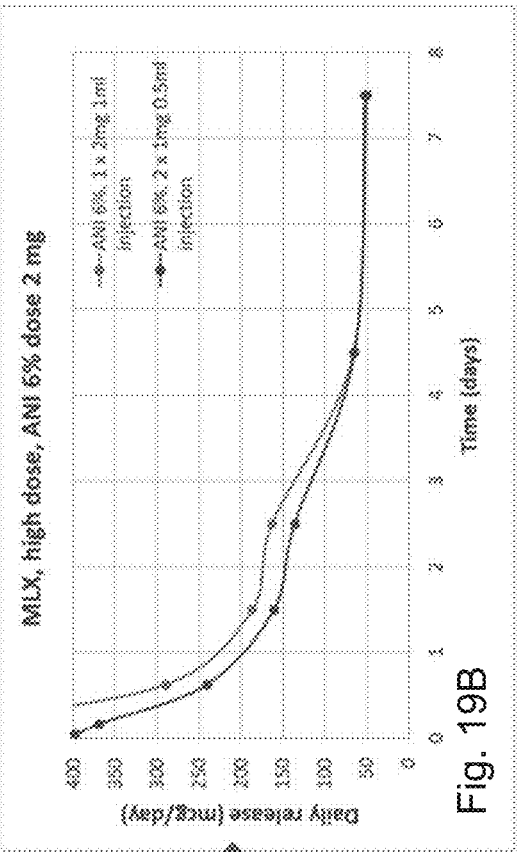
FIG. 19A shows daily release of carprofen in in extensive dissolution study up to 9 days with Anionic 6% NFC matrix and 2 mg CPF dose.
Figure 19B:
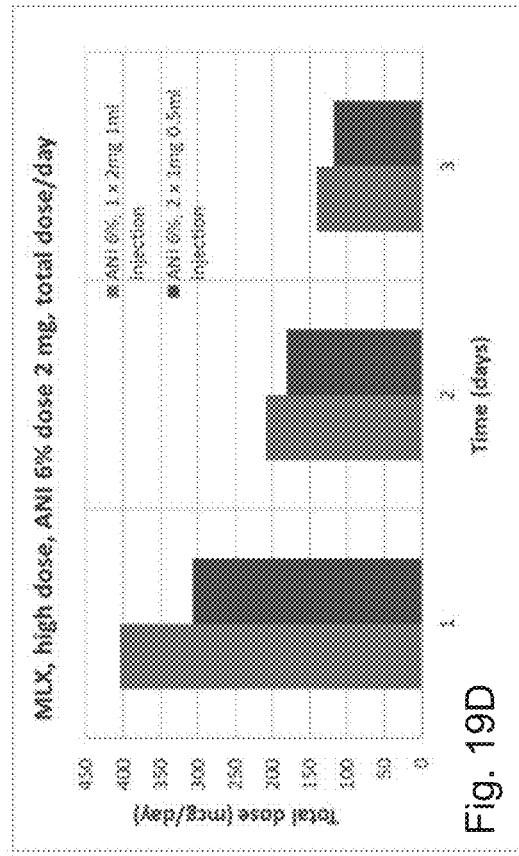
FIG. 19B shows daily release of carprofen in in extensive dissolution study up to 9 days with Anionic 6% NFC matrix and 2 mg CPF dose.
Figure 19C:
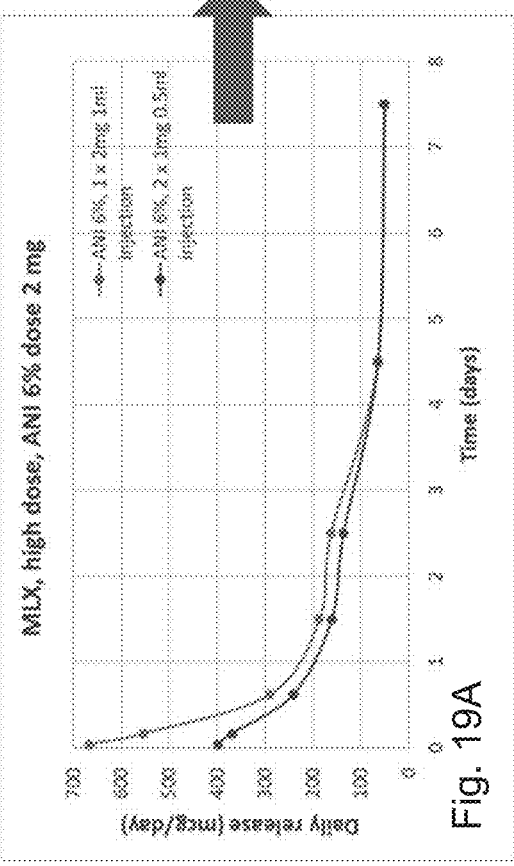
FIG. 19C shows cumulative release of carprofen in in extensive dissolution study up to 9 days with Anionic 6% NFC matrix and 2 mg CPF dose.
Figure 19D:
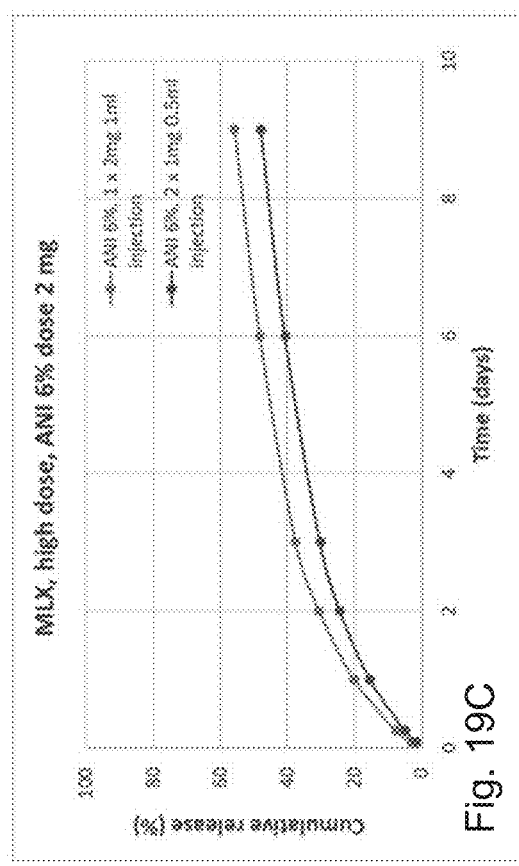
FIG. 19D shows a histogram of the total dose accumulated per day.
Figure 20A:
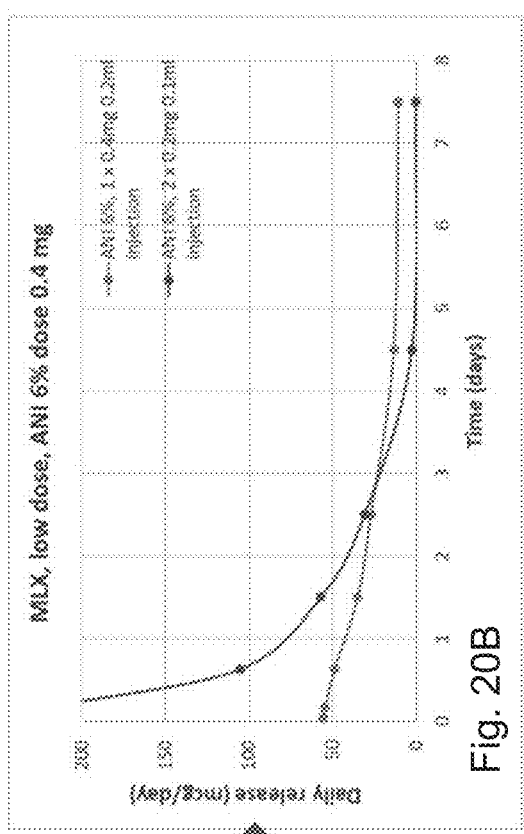
FIG. 20A shows daily release of carprofen in in extensive dissolution study up to 9 days with Anionic 6% NFC matrix and 0.4 mg CPF dose.
Figure 20B:
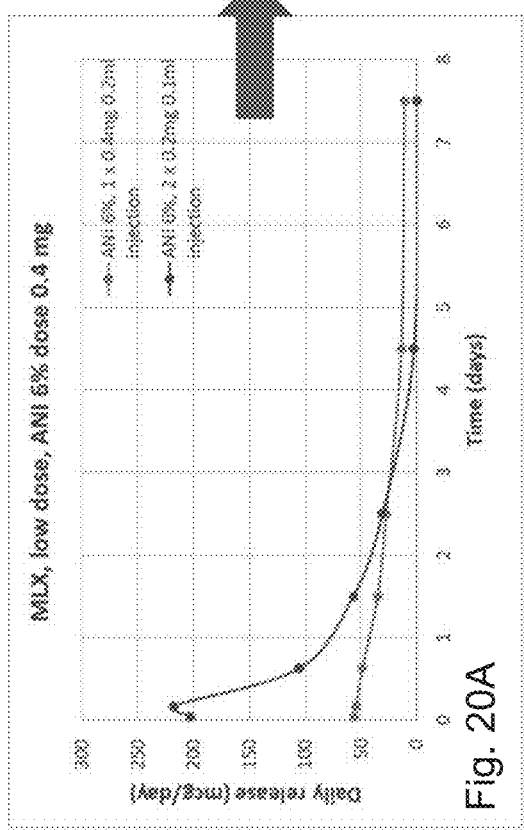
FIG. 20B shows daily release of carprofen in in extensive dissolution study up to 9 days with Anionic 6% NFC matrix and 0.4 mg CPF dose.
Figure 20D:
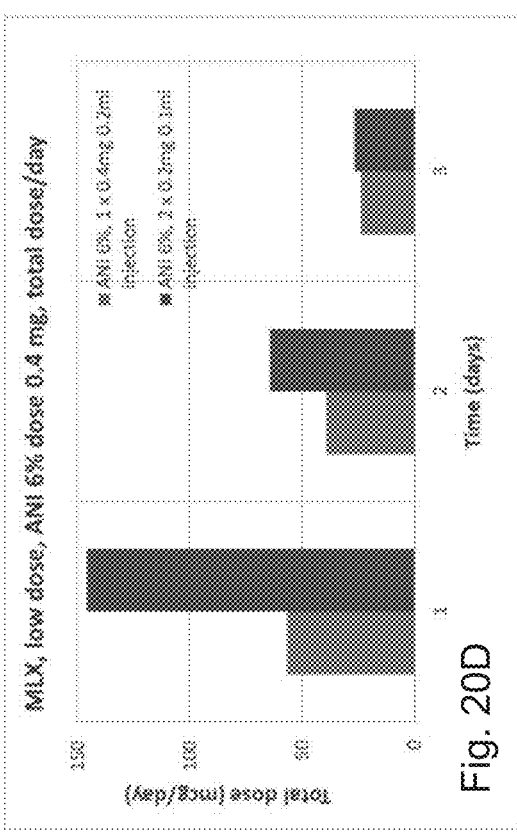
FIG. 20D shows a histogram of the total dose accumulated per day.
Figure 20C:
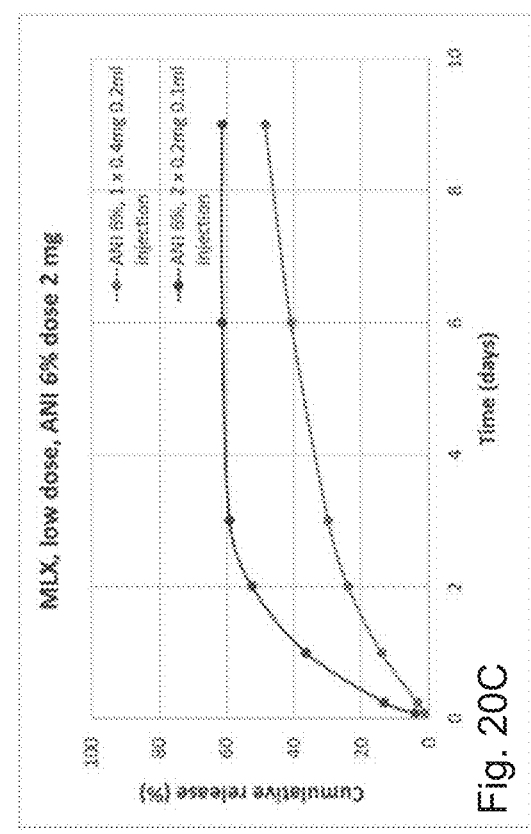
FIG. 20C shows cumulative release of carprofen in in extensive dissolution study up to 9 days with Anionic 6% NFC matrix and 0.4 mg CPF dose.

Cumulative release study aiming to increase cumulative result for NFC-formulations was performed with CPF, as it had clearly lower cumulative release results in previous experiments compared to MLX. 6% anionic and 1.5% native NFC were studied. Two solvents, DMSO (dimethyl sulfoxide) and NMP (N-methyl-2-pyrrolidone), in addition to H$_2$O were used to enhance the release of CPF. The study included formulation and short in vitro dissolution studies for NFC-API depots to follow cumulative release (FIG. 7). Depots contained 50% of solvent and 50% of NFC.

Figure 4:
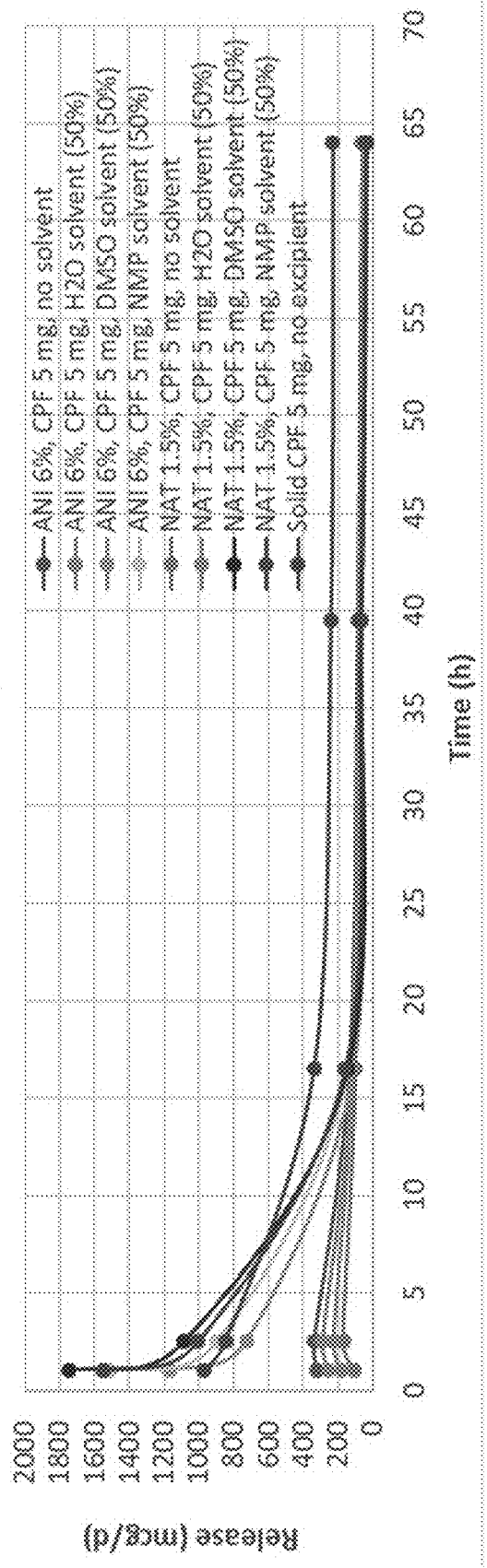
FIG. 4 shows the effect of DMSO, NMP and $H_2O$ on CPF release from NFC depots.
Figure 5B:
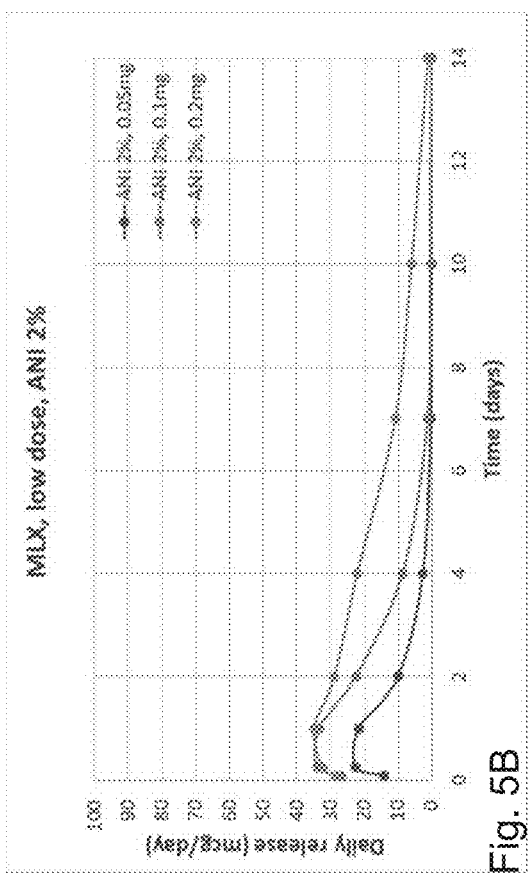
FIG. 5B shows daily release of meloxicam in extensive dissolution study up to 14 days (mcg/d, low dose range) with Anionic 2% NFC.
Figure 5D:
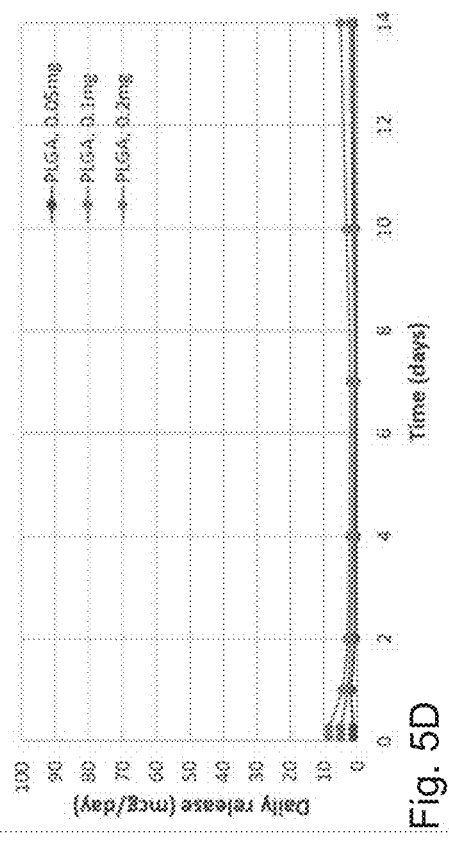
FIG. 5D shows daily release of meloxicam in extensive dissolution study up to 14 days (mcg/d, low dose range) with PLGA.
Figure 5A:
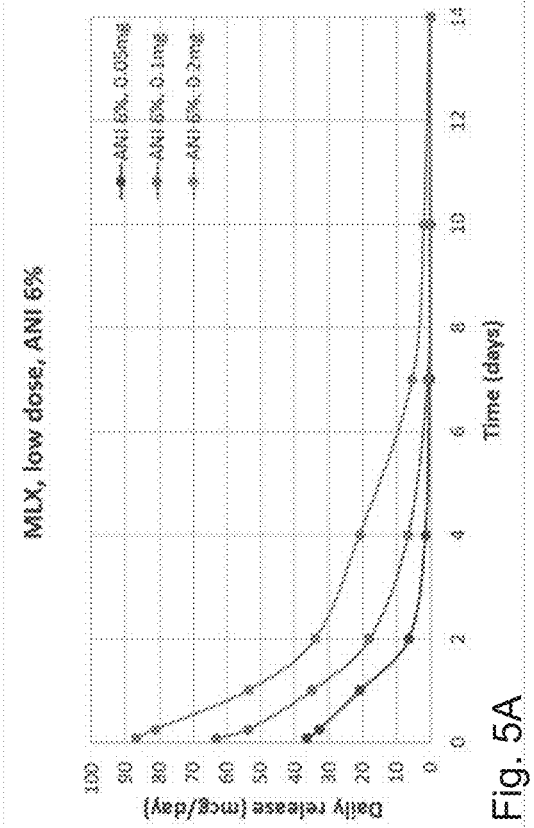
FIG. 5A shows daily release of meloxicam in extensive dissolution study up to 14 days (mcg/d, low dose range) with Anionic 6% NFC.
Figure 5C:
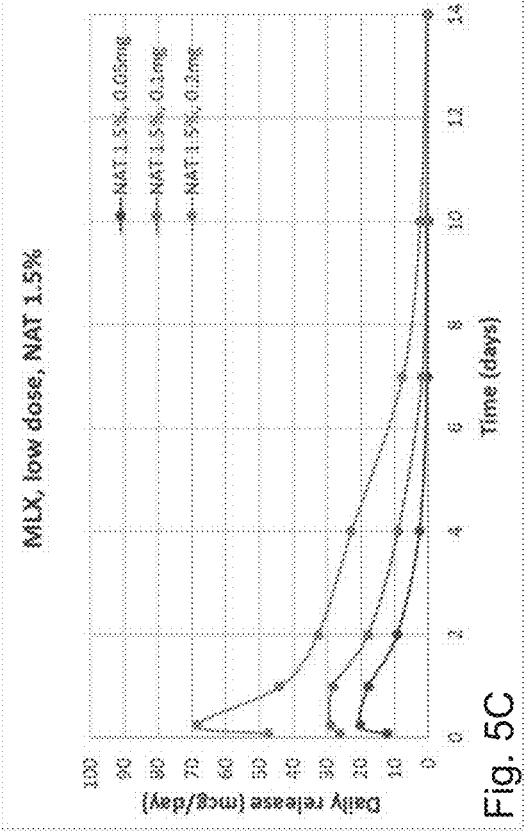
FIG. 5C shows daily release of meloxicam in extensive dissolution study up to 14 days (mcg/d, low dose range) with Native 1.5% NFC.
Figure 5E:
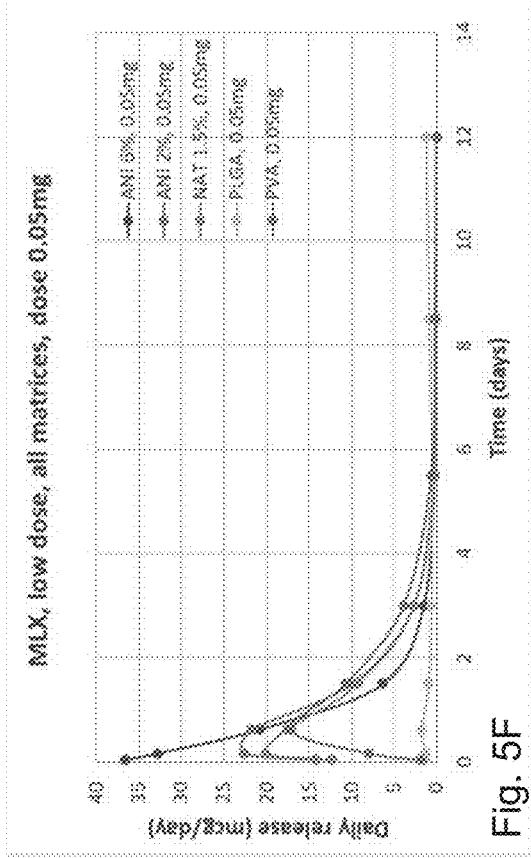
FIG. 5E shows daily release of meloxicam in extensive dissolution study up to 14 days (mcg/d, low dose range) with PVA.
Figure 5G:
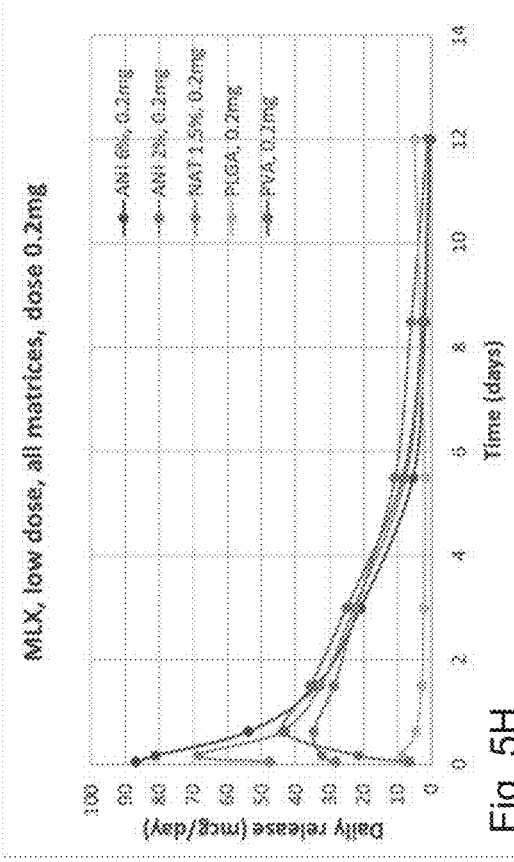
FIG. 5G shows daily release of meloxicam in extensive dissolution study up to 14 days (mcg/d, 0.1 mg dose) with all matrices.
Figure 5F:
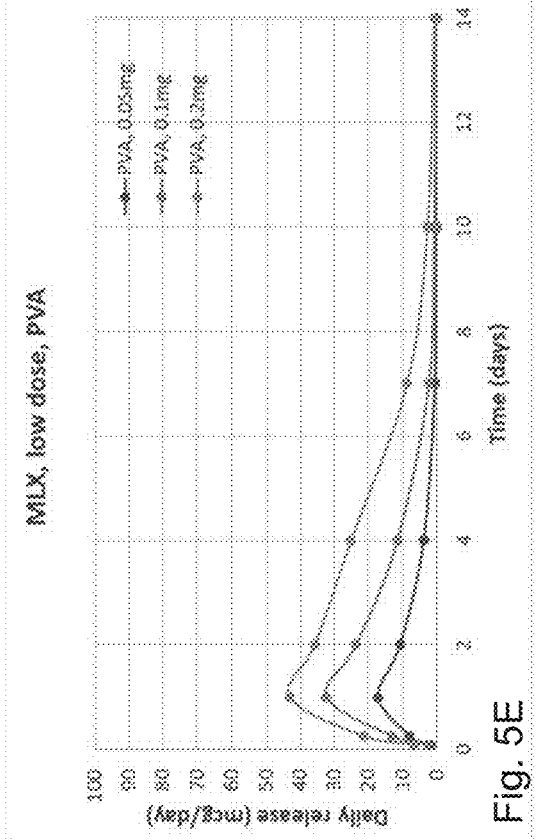
FIG. 5F shows daily release of meloxicam in extensive dissolution study up to 14 days (mcg/d, 0.05 mg dose) with all matrices.
Figure 5H:
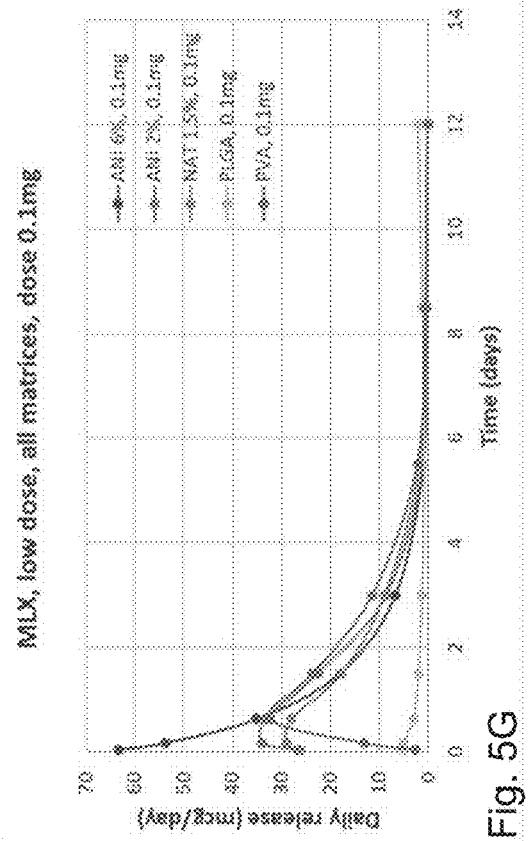
FIG. 5H shows daily release of meloxicam in extensive dissolution study up to 14 days (mcg/d, 0.2 mg dose) with all matrices
Figure 6E:
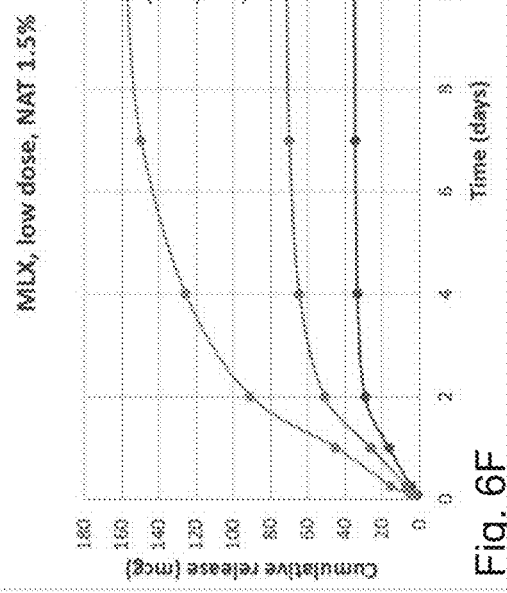
FIG. 6E shows cumulative release of meloxicam in extensive dissolution study up to 14 days with Native 1.5% NFC matrix.
Figure 6F:
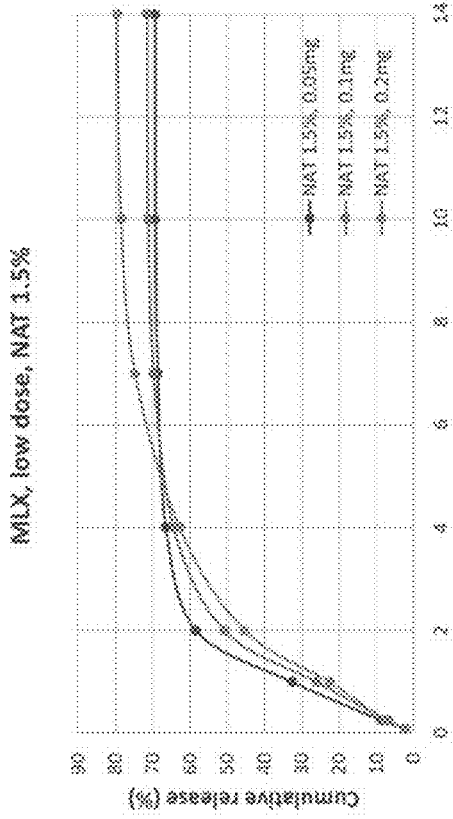
FIG. 6F shows cumulative release of meloxicam in extensive dissolution study up to 14 days with Native 1.5% NFC matrix.
Figure 6G:
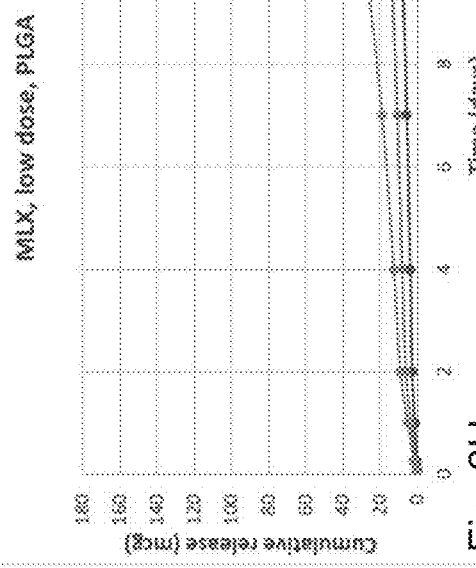
FIG. 6G shows cumulative release of meloxicam in extensive dissolution study up to 14 days with PLGA matrix.
Figure 6H:
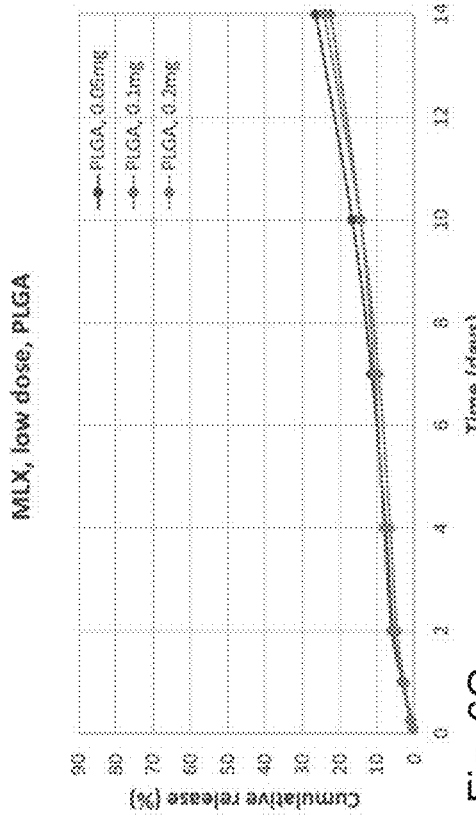
FIG. 6H shows cumulative release of meloxicam in extensive dissolution study up to 14 days with PLGA matrix.

FIG. 4 shows the effect of DMSO, NMP and $H_2O$ on CPF release from NFC depots. The results suggested that both solvents, DMSO and NMP, increased significantly daily release compared to NFC-API and NFC-$H_2O$-API formulations. Solvents increased the release of first hours even to the level of solid CPF, which was without any solvent or excipient. However, the increase was most apparent within the first hours and first day of study, which after the release reverted to the level of pure NFC formulations.

Based on these results, 50% DMSO was selected for extensive dissolution study for CPF-NFC high dose formulations, even though it seems that DMSO and NMP are relatively rapidly replaced by water and net effect to cumulative result will be mild. For the post-operative pain management, receiving high cumulative result within planned treatment period, 2-4 days, is vital, as longer release might lead to overdose of analgesics and adverse effects. On the contrary, low cumulative results indicate long-term release and possible indication in chronic pain management.

Extensive Dissolution

Extensive dissolution study was performed for all NFC and reference matrices with CPF and MLX. Study included three API doses, two replicates, three different forms of NFC gel (native 1.5%, 2% anionic and 6% anionic), two reference matrices PVA and PLGA and two dose ranges, low dose targeting for mouse and high dose targeting for rat. Sampling timepoints were 2 h, 6 h, day 1, day 2, day 4, day 7, day 10 and day 14.

Injection volumes in CPF low and high dose experiments and MLX low dose experiment were 100 µl/depot and in MLX high dose experiment 300 µl/depot. In CPF high dose experiment DMSO was used to increase the release. DMSO formulations were prepared by mixing DMSO/NFC (50/50) with speed mixing (2500 rpm, 1 min) prior addition of API which was mixed correspondingly with speed mixing (2500 rpm, 1 min, metal sphere). PLGA and PVA formulations were prepared correspondingly to feasibility and cumulative release phases.

Results are divided into four chapters; 1) MLX daily and cumulative release results, low dose range targeting for mice, 2) MLX daily and cumulative release results, high dose range targeting for rat, 3) CPF daily and cumulative release results, low dose range targeting for mice and 4) CPF daily and cumulative release results, high dose range targeting for rat.

Daily release results are presented as average of two sampling time points (for e.g. datapoint at day 12 represents result of day 14 measurement, thus, release from day 10 to day 14) whereas cumulative release results are presented based on measurement day. Each value is mean of two separate samples in dissolution (SD/SE not shown). Groups are named according to matrix (ANI 6%=6% anionic NFC, ANI 2%=2% anionic NFC, NAT 1.5%=1.5% native NFC, PLGA=PLGA Resomer® RG 502 poly(lactic-co-glycolic acid) and PVA=high molecular weight (MW 130.000) polyvinyl alcohol. The total amount of drug (mg) per injection is stated after group name.

MLX Daily Release, Low Dose Range

FIGS. 5A-H shows daily release of meloxicam in extensive dissolution study up to 14 days (mcg/d, low dose range). Anionic 6% NFC, Anionic 2% NFC, Native 1.5% NFC, PLGA and PVA matrices.

MLX Cumulative Release, Low Dose Range

FIGS. 6A-H show cumulative release of meloxicam in extensive dissolution study up to 14 days (% and mcg, low dose range). Anionic 6% NFC, Anionic 2% NFC, Native 1.5% NFC and PLGA matrices.

FIGS. 7A-H show cumulative release of meloxicam in extensive dissolution study up to 14 days (% and mcg, low dose range). PVA matrix and separately all matrices per dose in same figure.

FIGS. 8A-H show daily release of meloxicam in extensive dissolution study up to 14 days (mcg/d, high dose range). Anionic 6% NFC, Anionic 2% NFC, Native 1.5% NFC, PLGA and PVA matrices.

MLX Cumulative Release, High Dose Range

FIGS. 9A-H show cumulative release of meloxicam in extensive dissolution study up to 14 days (c)/0 and mcg, high dose range). Anionic 6% NFC, Anionic 2% NFC, Native 1.5% NFC and PLGA matrices.

FIGS. 10A-H show cumulative release of meloxicam in extensive dissolution study up to 14 days (% and mcg, high dose range). PVA matrix and separately all matrices per dose in same figure.

CPF Daily Release, Low Dose Range

FIGS. 11A-H show daily release of carprofen in extensive dissolution study up to 14 days (mcg/d, low dose range). Anionic 6% NFC, Anionic 2% NFC, Native 1.5% NFC, PLGA and PVA matrices.

CPF Cumulative Release, Low Dose Range

FIGS. 12A-G show cumulative release of carprofen in extensive dissolution study up to 14 days (% and mcg, low dose range). Anionic 6% NFC, Anionic 2% NFC, Native 1.5% NFC and PLGA matrices.

FIGS. 13A-G show cumulative release of carprofen in extensive dissolution study up to 14 days (% and mcg, low dose range). PVA matrix and separately all matrices per dose in same figure.

CPF Daily Release, High Dose Range

FIGS. 14A-H show daily release of carprofen in extensive dissolution study up to 14 days (mcg/d, high dose range). Anionic 6% NFC, Anionic 2% NFC, Native 1.5% NFC, PLGA and PVA matrices.

CPF Cumulative Release, High Dose Range

FIGS. 15A-G show cumulative release of carprofen in extensive dissolution study up to 14 days (c)/0 and mcg, high dose range). Anionic 6% NFC, Anionic 2% NFC, Native 1.5% NFC and PLGA matrices.

FIGS. 16A-G show cumulative release of carprofen in extensive dissolution study up to 14 days (% and mcg, high dose range). PVA matrix and separately all matrices per dose in same figure.

CPF, Additional Experiments, High Dose Range

FIGS. 17A-D show daily and cumulative release of carprofen in extensive dissolution study up to 9 days (mcg/day, % and mcg, high dose range). Histogram represents total dose accumulated per day. Anionic 6% NFC and 5 mg CPF dose. Two formulations: 1×1 ml injection, dose 5 mg CPF per injection and 2×0.5 ml injection, dose 2.5 mg CPF per injection. 750 µg/day<Target dose for rat<1500 µg/day for 2-4 days for post-operative pain management.

CPF, Additional Experiments, Low Dose Range

FIGS. 18A-D show daily and cumulative release of carprofen in extensive dissolution study up to 9 days (mcg/day, % and mcg, low dose range). Histogram represents total dose accumulated per day. Anionic 6% NFC and 0.5 mg CPF dose. Two formulations: 1×0.2 ml injection, dose 0.5 mg CPF per injection and 2×0.1 ml injection, dose 0.25 mg CPF per injection. 100 μg/day<Target dose for mouse<125 μg/day for 2-4 days for post-operative pain management.

MLX, Additional Experiments, High Dose Range

FIGS. 19A-D show daily and cumulative release of meloxicam in extensive dissolution study up to 9 days (mcg/day, % and mcg, high dose range). Histogram represents total dose accumulated per day. Anionic 6% NFC and 2 mg MLX dose. Two formulations: 1×1 ml injection, dose 2 mg MLX per injection and 2×0.5 ml injection, dose 1 mg MLX per injection. 250 μg/day<Target dose for rat<600 μg/day for 2-4 days for post-operative pain management.

MLX, Additional Experiments, Low Dose Range

FIGS. 20A-D show daily and cumulative release of meloxicam in extensive dissolution study up to 9 days (mcg/day, % and mcg, low dose range). Histogram represents total dose accumulated per day. Anionic 6% NFC and 0.4 mg MLX dose. Two formulations: 1×0.2 ml injection, dose 0.4 mg MLX per injection and 2×0.1 ml injection, dose 0.2 mg MLX per injection. 60 μg/day<Target dose for mouse<125 μg/day for 2-4 days for post-operative pain management.

CONCLUSIONS

The results of the PVA feasibility study suggested, that by using oxalic acid as a cross-linker PVA forms 3D gel-structure appropriate for the dissolution studies. Both reference materials, PVA/H$_2$O gel and PLGA/DMSO gel, were included in the extensive dissolution study. Based on the extensive dissolution study selected doses of Carprofen (CPF) and Meloxicam (MLX) showed sustained release for 3-14 days from NFC formulations The dose response was observed in all low dose formulations, but not high dose formulations, suggesting that the speed of dissolution of API to its environment is a limiting factor. This is mainly due to poor water solubility of CPF and MLX. The speed of dissolution of API to its environment can be speed up by increasing its surface area (=reduction of particle size by micronizing) and/or by increasing markedly matrix volume in injections. CPF and MLX formulations to achieve target doses for mouse post-operative pain treatment were identified and studied.

Optimal formulations concomitantly have high cumulative release, indicating good formulation for post-operative pain treatment in mice. Optimal doses can be achieved by using either the existing formulations with current injection volumes or slightly bigger volumes. Formulations at the target level were for e.g. 6% Anionic NFC with 0.5 mg CPF in 100 μl injection and 6% Anionic NFC with 0.1-0.2 mg MLX in 1-2×100 μl injection. These formulations have high initial burst, which is desired for the rapid onset of analgesic treatment. The high initial burst is short and releases only 5-10% of the total dose within first 6 hours.

50% DMSO (dimethyl sulfoxide) and 50% NMP (N-methyl-2-pyrrolidone) increased the release of CPF in the cumulative release dissolution study. The increase was most apparent within the first day of the study after which similar release as pure NFC was obtained. Despite the higher release at early time points, the cumulative release remained still low at the extensive 14-day dissolution study. CPF and MLX formulations to achieve target doses for rat post-operative pain treatment cannot be easily achieved with current formulations. Higher doses cannot be achieved by increasing the amount of API in NFC as limiting factor seems to be the speed of dissolution of API to its environment. Doses can be achieved by using existing mouse formulations with approximately 10-fold injection volumes (approximately 1 ml volume) or with several repeated injections. 1 ml total injection volume is still below rat maximum injection volume, however it might not be convenient to use. Low cumulative release values during two weeks with high dose formulation, indicate potentially good formulation for chronic pain, such as arthritis, treatment and sustained release even up to several weeks.

Based on feasibility and dissolution tests both forms of NFC, native and anionic form, can be used as excipient for analgesic compounds, however, 6% anionic form has some beneficial properties over other NFC forms, Such as better 3D gel structure, which helps in forming spherical depot and API suspension stability, and rapid and high release rate indicating increased bioavailability and rapid onset of efficacy in vivo.

Reference matrices PLGA/DMSO gel and PVA/H$_2$O gel showed sustained release properties. The release profile of PVA was similar to NFCs excluding initial burst, whereas release from PLGA was very low after initial burst. NFC gels were superior compared to reference matrices when considering post-operative pain management indication. PLGA/DMSO gel had overall too low release rates and too low cumulative release. PVA/H$_2$O gel had higher and close to target dose release rates, but also too low cumulative release for short-term release products. PVA was difficult to handle as it required laborious cross-linking procedure after which API suspendability was challenging.

The invention claimed is:

1. An injectable pharmaceutical formulation for subcutaneous, intradermal or intramuscular administration, comprising
    nanofibrillar cellulose hydrogel having a content of nanofibrillar cellulose in the range of 1.5 to 6.5% (w/w) and a water content of at least 82% (w/w), wherein the nanofibrillar cellulose has an average fibril diameter of 200 nm or less, and
    a pharmaceutical compound present as aggregates and/or as particles consisting of the pharmaceutical compound having an average diameter of more than 50 nm, the pharmaceutical compound having a water solubility of 0.001 to 0.1 mg/ml at 25° C.;
    the formulation having a storage modulus in the range of 350-5000 Pa and yield stress in the range of 25-300 Pa, determined by stress controlled rotational rheometer with gradually increasing shear stress in a range of 0.001-100 Pa at a frequency 10 rad/s, strain 2%, at 25° C.;
    wherein the injectable pharmaceutical formulation is a sustained release injectable pharmaceutical formulation.

2. The injectable pharmaceutical formulation of claim 1, wherein the nanofibrillar cellulose is chemically unmodified nanofibrillar cellulose.

3. The injectable pharmaceutical formulation of claim 1, wherein the nanofibrillar cellulose is anionically modified nanofibrillar cellulose.

4. The injectable pharmaceutical formulation of claim 1, wherein the content of the pharmaceutical compound is in the range of 0.1-10% (w/w).

5. The injectable pharmaceutical formulation of claim 1, wherein the pharmaceutical compound comprises an analgesic compound.

6. The injectable pharmaceutical formulation of claim 1 having a water content in the range of 82-98.9% (w/w).

7. The injectable pharmaceutical formulation of claim 1, wherein the formulation contains organic solvent.

8. The injectable pharmaceutical formulation of claim 1, wherein the sustained release injectable pharmaceutical formulation provides a sustained release of the pharmaceutical compound in 3-14 days, wherein at least 18% (w/w) of the pharmaceutical compound is released in 3-14 days.

9. The injectable pharmaceutical formulation of claim 1, wherein the sustained release injectable pharmaceutical formulation provides a sustained release of 20-40% (w/w) of the pharmaceutical compound during the first day.

10. A syringe containing the injectable pharmaceutical formulation of claim 1.

11. An implant containing the injectable pharmaceutical formulation of claim 1.

12. The injectable pharmaceutical formulation of claim 1, wherein the nanofibrillar cellulose is anionically modified nanofibrillar cellulose, wherein the formulation has a content of anionically modified nanofibrillar cellulose in the range of 4-6.5% (w/w).

13. The injectable pharmaceutical formulation of claim 1, wherein the nanofibrillar cellulose, when dispersed in water, provides a zero shear viscosity in the range of 1000-100000 Pa s and a yield stress in the range of 1-50 Pa, determined by rotational rheometer at a consistency of 0.5% (w/w) by weight in aqueous medium at 22° C.±1° C.

14. The injectable pharmaceutical formulation of claim 1, wherein the injectable pharmaceutical formulation provides an initial burst release of 5 to 10% of the pharmaceutical compound during the first six hours.

15. The injectable pharmaceutical formulation of claim 1, wherein the injectable pharmaceutical formulation exhibits an initial burst release of 5 to 20% of the pharmaceutical compound during the first six hours.

16. The injectable pharmaceutical formulation of claim 1, wherein the pharmaceutical compound has a water solubility of 0.00379 to 0.0168 mg/ml at 25° C.

17. The injectable pharmaceutical formulation of claim 1, wherein the pharmaceutical compound is meloxicam, carprofen, or buprenorphine.

18. The injectable pharmaceutical formulation of claim 1, wherein the subcutaneous, intradermal or intramuscular administration is via an injection needle.

19. A method for treating a subject in need of therapy, the method comprising
  recognizing a subject in need of therapy or treatment,
  providing the injectable pharmaceutical formulation of claim 1 or the implant of claim 11, and
  delivering or administering the injectable pharmaceutical formulation or the implant to the subject.

20. The method of claim 19 comprising injecting the pharmaceutical formulation to the subject.

21. The method of claim 19 for providing a sustained release of the pharmaceutical compound in the subject.

22. The method of claim 19, wherein the subject is a non-human animal.

23. The method of claim 19, wherein the treatment is analgesic treatment for pain management.

* * * * *